US010433557B2

United States Patent
Narva et al.

(10) Patent No.: US 10,433,557 B2
(45) Date of Patent: Oct. 8, 2019

(54) INSECTICIDAL CRY TOXINS

(71) Applicant: Dow AgroSciences LLC, Indianapolis, IN (US)

(72) Inventors: Kenneth E. Narva, Zionsville, IN (US); Huarong Li, Zionsville, IN (US); Sek Yee Tan, Carmel, IN (US); Tao Xu, Indianapolis, IN (US); Vimbai Chikwana, Indianapolis, IN (US); Kuan Yang, Indianapolis, IN (US); Marc D. Zack, Indianapolis, IN (US); Sarah E. Worden, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/478,449

(22) Filed: Apr. 4, 2017

(65) Prior Publication Data
US 2017/0290340 A1    Oct. 12, 2017

Related U.S. Application Data

(60) Provisional application No. 62/319,428, filed on Apr. 7, 2016.

(51) Int. Cl.
*C12N 15/82*     (2006.01)
*C07K 14/325*    (2006.01)
*A01N 63/02*     (2006.01)
*A01N 37/46*     (2006.01)

(52) U.S. Cl.
CPC .............. *A01N 63/02* (2013.01); *A01N 37/46* (2013.01); *C07K 14/325* (2013.01); *C12N 15/8286* (2013.01); *Y02A 40/162* (2018.01)

(58) Field of Classification Search
CPC .................................................. C12N 15/8286
See application file for complete search history.

(56) References Cited

U.S. PATENT DOCUMENTS

| 8,129,165 B2 * | 3/2012 | Lundberg ................. C07K 7/06 435/252.1 |
|---|---|---|
| 2011/0183896 A1 | 7/2011 | Adang et al. |
| 2012/0210462 A1 | 8/2012 | Bermudez et al. |
| 2012/0222173 A1 | 8/2012 | Goertz et al. |
| 2015/0203857 A1 | 7/2015 | Woosley et al. |

FOREIGN PATENT DOCUMENTS

WO    WO-2015109241 A1 *   7/2015   ............. A23L 7/198

OTHER PUBLICATIONS

Friedberg, Iddo. "Automated protein function prediction—the genomic challenge." Briefings in bioinformatics 7.3 (2006): 225-242. (Year: 2006).*
WO2017176688 International Preliminary Report on Patentability, dated Oct. 9, 2018.
WO2017176688 International Search Report, dated Aug. 17, 2017.
WO2017-025859 Written Opinion of the International Searching Authority, Aug. 17, 2017.
Li, et al. "Bacillus thuringiensis Cry34Ab1/Cry35Ab1 Interactions with Western Corn Rootworm Midgut Membrane Binding Sites," PLoS One, Apr. 1, 2013, vol. 8, No. 1, pp. 1-9.
Wangila et al. "Susceptibility of Nebraska Western Corn Rootworm, *Coleoptera chrysomelidae*) Populations to Bt Corn Events," Journal of Economic Entomology, Apr. 2, 2015, vol. 108, Iss. 2, pp. 742-751.

* cited by examiner

*Primary Examiner* — Weihua Fan

(57) ABSTRACT

Insecticidal toxins derived from *Bacillus thuringiensis*, polynucleotides encoding such toxins, use of such toxins to control Coleopteran plant pests, and transgenic plants that produce, and are protected by, these toxins are described.

13 Claims, No Drawings
Specification includes a Sequence Listing.

INSECTICIDAL CRY TOXINS

CROSS REFERENCE TO RELATED APPLICATION

This application claims the benefit of U.S. Provisional application No. 62/319,428, filed Apr. 7, 2016, entitled "INSECTICIDAL CRY TOXINS", the disclosure of which is being incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "78559-US-NP-20170328-Sequence-Listing_ST25", created on Mar. 7, 2017, and having a size of 106 kilobytes, and is filed concurrently with the specification. The sequence listing contained in this ASCII formatted document is part of the specification, and is incorporated herein by reference in its entirety.

TECHNICAL FIELD

The present invention relates generally to the field of molecular biology as applied to agricultural sciences. More particularly, certain embodiments concern methods for using DNA segments as diagnostic probes and templates for protein production, and the use of proteins, fusion protein carriers and peptides for insect control and in various immunological and diagnostic applications. Also disclosed are methods of making and using nucleic acid segments in the development of plant incorporated protectants in transgenic plant cells containing the DNA segments disclosed herein.

BACKGROUND

*Bacillus thuringiensis* is a Gram-positive bacterium that produces delta-endotoxins known as crystal proteins which are specifically toxic to certain orders and species of insects. Many different strains of *B. thuringiensis* have been shown to produce insecticidal crystal proteins. Compositions including *B. thuringiensis* strains which produce insecticidal proteins have been commercially available and used as environmentally acceptable insecticides.

The majority of insecticidal *B. thuringiensis* strains are active against insect of the order Lepidoptera, i.e., caterpillar insects. Other *B. thuringiensis* strains are active against insects of the order Diptera, i.e., flies and mosquitoes, or against both lepidopteran and dipteran insects. In recent years, a few *B. thuringiensis* strains have been reported as producing crystal proteins that are toxic to insects of the order Coleoptera, i.e., beetles, such as corn rootworms. Such currently deployed toxic proteins include Cry3Bb1, a modified Cry3A, eCry3.1Ab, and a binary toxin Cry34Ab1/Cry35Ab1 (requiring two different proteins for toxic activity). These proteins are effective for controlling *Diabrotica* species that infest corn roots, whether deployed singly, or in various combinations to decrease the likelihood of the development of resistance. Even though these proteins have been successfully deployed as insect control agents in transgenic crop plants, resistance to their effects can develop.

The classification of these crystal proteins was previously based on their target insect types. However, ongoing discovery of crystal proteins with very different amino acid sequences and insecticidal activities necessitated the development of a new classification system. The currently accepted nomenclature groups crystal proteins based on their amino acid sequences only. (Crickmore, N. et al. Microbiol. and Mol. Bio. Rev. (1998) Vol. 62: 807-813; http://www.btnomenclature.info/).

Resistance to a deployed toxin, whether chemistry or protein, is more likely to develop in a number of situations which enhance resistance development. Generally, the development of resistance is directly dependent on the length of time that a toxin is deployed into the environment. Resistance development is also more likely to increase in situations in which the dose of the toxin is insufficient to ensure mortality to the pest consuming a single bite of tissue containing the toxin. Accordingly, it is crucial to deliver a lethal dose of toxin with each bite, otherwise development of resistance to a particular toxin is more likely to occur. Repetitive use of the same toxin within a common geographic region on or in multiple species of plants which are susceptible to the same or similar pests within a common geographic region is more likely to cause rapid development of resistance to the toxin, particularly in climates in which there are multiple generations of a particular target pest within a single growing season. For all the forgoing reasons, dependence on a limited number of toxic proteins or toxic chemistries can result in the development of resistance to these pest control agents.

The western corn rootworm (WCR, *Diabrotica virgifera virgifera* LeConte) is a major corn insect pest throughout the United States Corn Belt. The options available for WCR management are limited due to the insect's propensity to adapt to both chemical pesticides and transgenic corn hybrids expressing B.t. Cry proteins, as well as cultural measures such as crop rotation with soybean. In recent years, WCR at specific geographic areas has developed significant resistance to Cry3Bb, likely due to continuously planting Cry3Bb transgenic corn. It has been shown that WCR selected with Cry3Bb is cross resistant to mCry3Aa (Gassmann et al., 2014; Gassmann et al., 2011). Although there has been no report of resistance issue with Cry34/35Ab1 maize traits, Cry34/35 trait is under increasing selection pressure due to larger planting area, e.g. the commercialization of SmartStax, and the possibility of Cry34/35Ab1 selection on top of Cry3-resistant WCR population. The corn rootworm trait market needs novel insecticidal genes with a new mode of action (MOA) for sustainable corn rootworm control (Narva et al., 2013). Other proteins disclosed in the art that are asserted to exhibit toxic effects to corn rootworms include patatin, TIC100/101 binary toxin, ET33/34 binary toxin, TIC863, ET80/76 binary toxin, ET70, Cry3Bb (U.S. Pat. No. 6,501,009), Cry1C variants, Cry3A variants, Cry3, Cry3B, Cry34/35, 5307, Axmi184, Axmi205, AxmiRl, TIC901, TIC1201, TIC407, TIC417, TIC431, TIC807, TIC853, TIC3131, eHIPs (U.S. Patent Application Publication No. 2010/0017914), and ω-Hex atoxin-Hv 1a (U.S. Patent Application Publication US2014-0366227 A1).

Despite the discovery of many selective protein toxins from *B. thuringiensis*, there remains a critical need to discover new, effective pest control agents that provide economic benefits to farmers especially against *Diabrotica virgifera virgifera* (Western Corn Rootworm (WCR)), and are environmentally acceptable. Particularly needed are agents targeted to control a wide spectrum of economically important insect pests that effectively control insect populations that are, or could become, resistant to existing insect control agents and those with equal to or increased potency compared to currently deployed insecticidal IRDIG protein toxins.

SUMMARY OF THE INVENTION

The present invention is based on the discovery of novel protein toxins having insecticidal activity against WCR. These insecticidal proteins and the genes have little homology to all the known proteins and genes of the prior art and demonstrate surprising insecticidal activity against insects including but not limited to the order Coleoptera. Based on the amino acid sequence of these native insecticidal toxins, they are not related at the primary sequence level to any known family B. thuringiensis proteins.

The present invention provides novel B. thuringiensis insecticidal IRDIG protein toxins and the genes encoding them. The invention also includes homologs, N-terminal deletions, derivatives, analogs, and mutant forms of these insecticidal toxins, plant codon optimized nucleic acid sequences encoding the claimed toxins, methods for making, using the toxins and antibodies that selectively bind these toxins.

The present invention also concerns DNA segments, which can be isolated from virtually any source, that are free from total genomic DNA and that encode the whole or a portion of the novel peptides disclosed herein. The insecticidal IRDIG protein gene encodes the insecticidal IRDIG protein having an amino acid sequence and size as referenced in Table 1.

TABLE 1

| Name | Gene SEQ ID NO | Protein SEQ ID NO | Predicted Protein Size (kDa) |
| --- | --- | --- | --- |
| IRDIG28688.1 | 1 | 2 | 21.8 |
| IRDIG28686.1 | 3 | 4 | 21.6 |
| IRDIG28684.1 | 5 | 6 | 21.5 |
| IRDIG28682.1 | 7 | 8 | 21.6 |
| IRDIG28680.1 | 9 | 10 | 12.3 |
| IRDIG28674.1 | 11 | 12 | 20.9 |
| IRDIG28672.1 | 13 | 14 | 21.1 |
| IRDIG27642.1 | 15 | 16 | 21.1 |
| IRDIG28678.2 | 17 | 18 | 21.4 |
| IRDIG28678.1 | 19 | 20 | 21.4 |
| IRDIG31125.1 | 21 | 22 | 22.0 |
| IRDIG28696.1 | 23 | 24 | 13.5 |
| IRDIG29781.1 | 25 | 26 | 14.3 |
| IRDIG29779.1 | 27 | 28 | 20.7 |
| IRDIG30844.1 | 29 | 30 | 21.8 |
| IRDIG30850.1 | 31 | 32 | 21.1 |
| IRDIG30852.1 | 33 | 34 | 21.8 |
| IRDIG30854.1 | 35 | 36 | 21.5 |
| IRDIG30856.1 | 37 | 38 | 13.5 |
| IRDIG30858.1 | 39 | 40 | 18.4 |
| IRDIG30862.1 | 41 | 42 | 10.7 |
| IRDIG30860.1 | 43 | 44 | 10.7 |
| IRDIG30848.1 | 45 | 46 | 21.4 |
| IRDIG30858.1 | 119 | 120 | 12.8 |
| IRDIG28676.1 | 121 | 122 | 23.7 |
| IRDIG28692.1 | 123 | 124 | 22.1 |
| IRDIG28694.1 | 125 | 126 | 13.6 |

In particular embodiments, the invention concerns isolated DNA segments, recombinant vectors incorporating DNA sequences that encode the claimed toxins, and functional genetic inserts found in the genomes of plants that result from transforming plants with such recombinant vectors. More preferably, the DNA segments comprise a nucleic acid sequence that encodes a protein or peptide toxin that includes within its amino acid sequence an at least ten amino acid contiguous sequence of SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, and 122.

Similarly, a DNA segment comprising an isolated or purified protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extrachromosomal DNA sequences, but also operon sequences and engineered gene segments that express, or may be adapted to express, functional proteins, polypeptides or peptides.

BRIEF DESCRIPTION OF THE SEQUENCES

SEQ ID NO:1 is a B. thuringiensis DNA sequence encoding IRDIG28688.1 toxin; 570 nt.

SEQ ID NO:2 is the B. thuringiensis IRDIG28688.1 protein sequence encoded by SEQ ID NO:1, 189 aa.

SEQ ID NO:3 is a B. thuringiensis DNA sequence encoding IRDIG28686.1; 564 nt.

SEQ ID NO:4 is a B. thuringiensis protein sequence from IRDIG28686.1; 187 aa.

SEQ ID NO:5 is a B. thuringiensis DNA sequence from IRDIG28684.1; 564 nt.

SEQ ID NO:6 is a B. thuringiensis protein sequence from IRDIG28684.1; 187 aa.

SEQ ID NO:7 is a B. thuringiensis DNA sequence from IRDIG28682.1; 564 nt.

SEQ ID NO:8 is a B. thuringiensis protein sequence from IRDIG28682.1; 187 aa.

SEQ ID NO:9 is a B. thuringiensis DNA sequence from IRDIG28680.1; 333 nt.

SEQ ID NO:10 is a B. thuringiensis protein sequence from IRDIG28680.1; 110 aa.

SEQ ID NO:11 is a B. thuringiensis DNA sequence from IRDIG28674.1; 555 nt.

SEQ ID NO:12 is a B. thuringiensis protein sequence from IRDIG28674.1; 184 aa.

SEQ ID NO:13 is a B. thuringiensis DNA sequence from IRDIG28672.1; 555 nt.

SEQ ID NO:14 is a B. thuringiensis protein sequence from IRDIG28672.1; 184 aa.

SEQ ID NO:15 is a B. thuringiensis DNA sequence from IRDIG27642; 555 nt.

SEQ ID NO:16 is a B. thuringiensis protein sequence from IRDIG27642; 184 aa.

SEQ ID NO:17 is a B. thuringiensis DNA sequence from IRDIG28678.2; 558 nt.

SEQ ID NO:18 is a B. thuringiensis protein sequence from IRDIG28678.2; 185 aa.

SEQ ID NO:19 is a B. thuringiensis DNA sequence from IRDIG28678.1; 558 nt.

SEQ ID NO:20 is a B. thuringiensis protein sequence from IRDIG28678.1; 185 aa.

SEQ ID NO:21 is a B. thuringiensis DNA sequence from IRDIG31125.1; 576 nt.

SEQ ID NO:22 is a B. thuringiensis protein sequence from IRDIG31125.1; 191 aa

SEQ ID NO:23 is a B. thuringiensis DNA sequence from IRDIG28696.1; 366 nt.

SEQ ID NO:24 is a B. thuringiensis protein sequence from IRDIG28696.1; 121 aa.

SEQ ID NO:25 is a B. thuringiensis DNA sequence from IRDIG29781.1; 387 nt.

SEQ ID NO:26 is a *B. thuringiensis* protein sequence from IRDIG29781.1; 128 aa.

SEQ ID NO:27 is a *B. thuringiensis* DNA sequence from IRDIG29779.1; 537 nt.

SEQ ID NO:28 is a *B. thuringiensis* protein sequence from IRDIG29779.1; 178 aa.

SEQ ID NO:29 is a *B. thuringiensis* DNA sequence from IRDIG 30844.1; 570 nt.

SEQ ID NO:30 is a *B. thuringiensis* protein sequence from IRDIG30844.1; 189 aa.

SEQ ID NO:31 is a *B. thuringiensis* DNA sequence from IRDIG30850.1; 639 nt.

SEQ ID NO:32 is a *B. thuringiensis* protein sequence from IRDIG30850.1; 212 aa.

SEQ ID NO:33 is a *B. thuringiensis* DNA sequence from IRDIG30852.1; 570 nt.

SEQ ID NO:34 is a *B. thuringiensis* protein sequence from IRDIG30852.1; 189 aa.

SEQ ID NO:35 is a *B. thuringiensis* DNA sequence from IRDIG30854.1; 564 nt.

SEQ ID NO:36 is a *B. thuringiensis* protein sequence from IRDIG30854.1; 187 aa.

SEQ ID NO:37 is a *B. thuringiensis* DNA sequence from IRDIG30856.1; 366 nt.

SEQ ID NO:38 is a *B. thuringiensis* protein sequence from IRDIG30856.1; 121 aa.

SEQ ID NO:39 is a *B. thuringiensis* DNA sequence from IRDIG30858.1; 492 nt.

SEQ ID NO:40 is a *B. thuringiensis* protein sequence from IRDIG30858.1; 163 aa.

SEQ ID NO:41 is a *B. thuringiensis* DNA sequence from IRDIG30862.1; 285 nt.

SEQ ID NO:42 is a *B. thuringiensis* protein sequence from IRDIG30862.1; 94 aa.

SEQ ID NO:43 is a *B. thuringiensis* DNA sequence from IRDIG30860.1; 285 nt.

SEQ ID NO:44 is a *B. thuringiensis* protein sequence from IRDIG30860.1; 94 aa.

SEQ ID NO:45 is a *B. thuringiensis* DNA sequence from IRDIG30848.1; 561 nt.

SEQ ID NO:46 is a *B. thuringiensis* protein sequence from IRDIG30848.1; 186 aa.

SEQ ID NOs:47-68 primers used to amplify portions of insecticidal IRDIG proteins listed above.

SEQ ID NO:69 IRDIG27642.2 is a codon-optimized DNA sequence encoding IRDIG27642 toxin using the ZmHGC strategy; 555 nt SEQ ID NO:70 IRDIG27642.3 is a codon-optimized DNA sequence encoding IRDIG27642 toxin using the Zm Highest GC strategy; 555 nt SEQ ID NO:71 is a *B. thuringiensis* protein sequence from IRDIG27642.2 and IRDIG27642.3; 184 aa.

SEQ ID NO:72 IRDIG27642.4 TraP8 fused to IRDIG27642 Zm Highest GC; 753

SEQ ID NO:73 is a *B. thuringiensis* protein sequence from IRDIG27642.4 and IRDIG27642.6; 250 aa.

SEQ ID NO:74 IRDIG27642.5 TraP4 fused to IRDIG27642 ZmHGC; 768

SEQ ID NO:75 is a *B. thuringiensis* protein sequence from IRDIG27642.5; 255 aa

SEQ ID NO:76 IRDIG27642.6 TraP8 fused to IRDIG27642 ZmHGC; 753

SEQ ID NO:77 IRDIG27642-F1BamHI is the forward primer sequence for PCR and for expression after the PCR product was cloned into BamI/KpnI cut pDAB101622 in Bt 4Q7

SEQ ID NO:78 IRDIG27642-R1KpnI is the reverse primer sequence for PCR and for expression after the PCR product was cloned into BamI/KpnI cut pDAB101622 in Bt 4Q7

SEQ ID NO:79 IRDIG27642-00733-F2SpeI is the forward primer sequence for PCR and for expression after the PCR product was cloned into SpeI/XhoI cut pDOW1169 in Pf SEQ ID NO:80 IRDIG27642-00733-R2XhoI is the reverse primer for PCR and for expression after the PCR product was cloned into SpeI/XhoI cut pDOW1169 in Pf SEQ ID NO:81 is a truncated *B. thuringiensis* DNA sequence from IRDIG27642.1

SEQ ID NO:82 is a truncated *B. thuringiensis* protein sequence from IRDIG27642.1

SEQ ID NO:83 is a *B. thuringiensis* DNA sequence from IRDIG28672.1

SEQ ID NO:84 is a truncated *B. thuringiensis* protein sequence from IRDIG28672.1

SEQ ID NO:85 is a *B. thuringiensis* DNA sequence from IRDIG28674.1

SEQ ID NO:86 is a truncated *B. thuringiensis* protein sequence from IRDIG28674.1

SEQ ID NO:87 is a *B. thuringiensis* DNA sequence from IRDIG28678.1

SEQ ID NO:88 is a truncated *B. thuringiensis* protein sequence from IRDIG28678.1

SEQ ID NO:89 is a *B. thuringiensis* DNA sequence from IRDIG31125.1

SEQ ID NO:90 is a truncated *B. thuringiensis* protein sequence from IRDIG31125.1

SEQ ID NO:91 is a *B. thuringiensis* DNA sequence from IRDIG28680.1

SEQ ID NO:92 is a truncated *B. thuringiensis* protein sequence from IRDIG28680.1

SEQ ID NO:93 is a *B. thuringiensis* DNA sequence from IRDIG28682.1

SEQ ID NO:94 is a truncated *B. thuringiensis* protein sequence from IRDIG28682.1

SEQ ID NO:95 is a *B. thuringiensis* DNA sequence from IRDIG28684.1

SEQ ID NO:96 is a truncated *B. thuringiensis* protein sequence from IRDIG28684.1

SEQ ID NO:97 is a *B. thuringiensis* DNA sequence from IRDIG28686.1

SEQ ID NO:98 is a truncated *B. thuringiensis* protein sequence from IRDIG28686.1

SEQ ID NO:99 is a *B. thuringiensis* DNA sequence from IRDIG28688.1

SEQ ID NO:100 is a truncated *B. thuringiensis* protein sequence from IRDIG28688.1

SEQ ID NO:101 is a *B. thuringiensis* DNA sequence from IRDIG28696.1

SEQ ID NO:102 is a truncated *B. thuringiensis* protein sequence from IRDIG28696.1

SEQ ID NO:103 is a *B. thuringiensis* DNA sequence from IRDIG29779.1

SEQ ID NO:104 is a truncated *B. thuringiensis* protein sequence from IRDIG29779.1

SEQ ID NO:105 is a *B. thuringiensis* DNA sequence from IRDIG29781.1

SEQ ID NO:106 is a truncated *B. thuringiensis* protein sequence from IRDIG29781.1

SEQ ID NO:107 is a *B. thuringiensis* DNA sequence from IRDIG30844.1

SEQ ID NO:108 is a truncated *B. thuringiensis* protein sequence from IRDIG30844.1

SEQ ID NO:109 is a *B. thuringiensis* DNA sequence from IRDIG30848.1

SEQ ID NO:110 is a truncated *B. thuringiensis* protein sequence from IRDIG30848.1

SEQ ID NO:111 is a *B. thuringiensis* DNA sequence from IRDIG30850.1

SEQ ID NO:112 is a truncated *B. thuringiensis* protein sequence from IRDIG30850.1

SEQ ID NO:113 is a *B. thuringiensis* DNA sequence from IRDIG30852.1

SEQ ID NO:114 is a truncated *B. thuringiensis* protein sequence from IRDIG30852.1

SEQ ID NO:115 is a *B. thuringiensis* DNA sequence from IRDIG30854.1

SEQ ID NO:116 is a truncated *B. thuringiensis* protein sequence from IRDIG30854.1

SEQ ID NO:117 is a *B. thuringiensis* DNA sequence from IRDIG30856.1

SEQ ID NO:118 is a truncated *B. thuringiensis* protein sequence from IRDIG30856.1

SEQ ID NO:119 is a *B. thuringiensis* DNA sequence from IRDIG30858.1

SEQ ID NO:120 is a truncated *B. thuringiensis* protein sequence from IRDIG30858.1

SEQ ID NO:121 is a *B. thuringiensis* DNA sequence from IRDIG28676.1; 624 nt.

SEQ ID NO:122 is a *B. thuringiensis* protein sequence from IRDIG28676.1; 207 aa.

SEQ ID NO:123 is a *B. thuringiensis* DNA sequence from IRDIG28692.1; 579 nt.

SEQ ID NO:124 is a *B. thuringiensis* protein sequence from IRDIG28692.1; 192 aa SEQ ID NO:125 is a *B. thuringiensis* DNA sequence from IRDIG28694.1; 366 nt.

SEQ ID NO:126 is a *B. thuringiensis* protein sequence from IRDIG28694.1; 121 aa.

SEQ ID NOs:127-132 primers used to amplify portions of insecticidal IRDIG proteins.

DETAILED DESCRIPTION OF THE INVENTION

The following words and phrases have the meanings set forth below. Unless specifically indicated, the terms "a", "an", and "the" signify "at least one" as used herein.

An "insecticidal IRDIG protein" is defined as SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126 protein toxins have at least 70% sequence identity with any of the foregoing including derivatives, analogs, and mutant forms. A more preferred group of insecticidal IRDIG proteins consists of SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126, protein toxins have at least 80% sequence identity with any of the foregoing sequences. Another preferred group of insecticidal IRDIG proteins consists of SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126, protein toxins have at least 90% sequence identity with any of the foregoing sequences. Another preferred group of insecticidal IRDIG proteins consists of SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126, protein toxins have at least 95% sequence identity with any of the foregoing sequences. Another preferred group of insecticidal IRDIG proteins consists of SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126, protein toxins have at least 99% sequence identity with any of the foregoing sequences. The most preferred group of insecticidal IRDIG proteins toxins consists of SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126.

A "formulated insecticidal IRDIG protein" means purified or isolated insecticidal IRDIG protein that has been expressed or placed into a synthetic composition suitable for agricultural application, including but not limited to transgenic plants, sprayable liquid formulations, powdered solid formulations, or granular formulations.

"DNA segment" refers to a DNA molecule that has been isolated free of total genomic DNA of a particular species. Therefore, a DNA segment encoding a protein or peptide refers to a DNA segment that contains protein coding sequences yet is isolated away from, or purified free from, total genomic DNA of the species from which the DNA segment is obtained, which in the instant case is the genome of the Gram-positive bacterial genus, *Bacillus*, and in particular, the species known as *B. thuringiensis*. Included within the term "DNA segment", are DNA segments and smaller fragments of such segments, and also recombinant vectors, including, for example, plasmids, cosmids, phagemids, phage, viruses, and the like.

"Isolated substantially away from other coding sequences" means that the gene of interest, in this case, a gene encoding a bacterial insecticidal IRDIG protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

"A sequence essentially as set forth in SEQ ID NO:2" means that the sequence substantially corresponds to a portion of the sequence of SEQ ID NO:2 and has relatively few amino acids that are not identical to, or a biologically functional equivalent of, the amino acids of any of these sequences. The term "biologically functional equivalent" is well understood in the art. Accordingly, sequences that have between about 70% and about 80%, or more preferably between about 81% and about 90%, or even more preferably between about 91% and about 99% amino acid sequence identity or functional equivalence to the amino acids of SEQ ID NO:2 will be sequences that are "essentially as set forth in SEQ ID NO:2."

"Expression" means the combination of intracellular processes, including transcription and translation undergone by a coding DNA molecule such as a structural gene to produce a polypeptide.

"Genetic material" means all genes, nucleic acid, DNA and RNA. The term "dsRNA" refers to double-stranded RNA. For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

"Promoter" means a recognition site on a DNA sequence or group of DNA sequences that provide an expression control element for a structural gene and to which RNA polymerase specifically binds and initiates RNA synthesis (transcription) of that gene.

"Nucleic acid construct" is an artificially created genetic sequence comprising a structural gene such as an IRDIG gene sequence and heterologous regulatory elements such as promoter, terminators, enhancers, or other genetic elements designed to cause the transcription or translation of the structural gene in an appropriate host.

"Regeneration" means the process of growing a plant from a plant cell (e.g., plant protoplast or explant).

"Structural gene" means a gene that is expressed to produce a polypeptide.

"Transformation" means process of introducing an exogenous DNA sequence (e.g., a vector, a recombinant DNA molecule) into a cell or protoplast in which that exogenous DNA is incorporated into a chromosome or is capable of autonomous replication.

"Transformed cell" means a cell whose DNA has been altered by the introduction of an exogenous DNA molecule into that cell.

"Transgenic cell" means any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

"Transgenic plant" means a plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

"Vector" means a DNA molecule capable of replication in a host cell and/or to which another DNA segment can be operatively linked so as to bring about replication of the attached segment. A plasmid is an exemplary vector.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding regions, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the whole or a portion of the peptide sequence disclosed in SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126, or that are identical to or complementary to DNA sequences which encode the peptide disclosed in SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126, and particularly the DNA segment disclosed in SEQ ID NOs:1, 3, 5, 7, 9, 11, 13, 15, 17, 19, 21, 23, 25, 27, 29, 31, 33, 35, 37, 39, 41, 43, 45, 69, 70, 72, 74, 76, 81, 83, 85, 87, 89, 91, 93, 95, 97, 99, 101, 103, 105, 107, 109, 111, 113, 115, 117, 119, 121, 123, and 125. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; and up to and including sequences of about 10,000 nucleotides and the like.

It will also be understood that this invention is not limited to the particular nucleic acid sequences which encode peptides of the present invention, or which encode the amino acid sequence of SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, and 126, including the DNA sequence which is particularly disclosed in SEQ ID NOs:1, 3, 5, 7, 9, 11, 13, 15, 17, 19, 21, 23, 25, 27, 29, 31, 33, 35, 37, 39, 41, 43, 45, 69, 70, 72, 74, 76, 81, 83, 85, 87, 89, 91, 93, 95, 97, 99, 101, 103, 105, 107, 109, 111, 113, 115, 117, 119, 121, 123, and 125. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

In addition to their use in directing the expression of insecticidal IRDIG proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NOs:1, 3, 5, 7, 9, 11, 13, 15, 17, 19, 21, 23, 25, 27, 29, 31, 33, 35, 37, 39, 41, 43, 45, 69, 70, 72, 74, 76, 81, 83, 85, 87, 89, 91, 93, 95, 97, 99, 101, 103, 105, 107, 109, 111, 113, 115, 117, 119, 121, 123, and 125, will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences) will also be of use in certain embodiments.

The ability of such nucleic acid probes to specifically hybridize to protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10-14, 15-20, 30, 50, or even of 100-200 nucleotides or so, identical or complementary to the DNA sequence of SEQ ID NOs:1, 3, 5, 7, 9, 11, 13, 15, 17, 19, 21, 23, 25, 27, 29, 31, 33, 35, 37, 39, 41, 43, 45, 69, 70, 72, 74, 76, 81, 83, 85, 87, 89, 91, 93, 95, 97, 99, 101, 103, 105, 107, 109, 111, 113, 115, 117, 119, 121, 123, and 125, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours. Such selective conditions tolerate little, if any, mismatch between the probe and the template or target strand, and would be particularly suitable for isolating protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation:

$$T_m(°\,C.)=81.5°\,C.+16.6(\log M)+0.41(\%\,GC)-0.61(\%\,\text{formamide})-500/L;$$

where M is the molarity of monovalent cations, % GC is the percentage of guanosine and cytosine nucleotides in the DNA, % formamide is the percentage of formamide in the hybridization solution (w/v), and L is the length of the hybrid in base pairs.

Alternatively, the $T_m$ is described by the following formula (Beltz et al., 1983).

$$T_m(°\,C.)=81.5°\,C.+16.6(\log [Na+])+0.41(\%\,GC)-0.61(\%\,\text{formamide})-600/L$$

where [Na+] is the molarity of sodium ions, % GC is the percentage of guanosine and cytosine nucleotides in the DNA, % formamide is the percentage of formamide in the hybridization solution (w:v), and L is the length of the hybrid in base pairs.

Using the equations, hybridization and wash compositions, and desired $T_m$, those of ordinary skill will understand that variations in the stringency of hybridization and wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993). Also see Sambrook et al. (1989).

Of course, for some applications, for example, where one desires to prepare mutants employing a mutant primer strand hybridized to an underlying template or where one seeks to isolate protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

The invention also discloses and claims a composition comprising an insecticidal IRDIG protein. The composition may comprises bacterial host cells which express an insecticidal IRDIG protein, in the soluble fraction, inclusion bodies or crystals containing the insecticidal IRDIG protein, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing insecticidal IRDIG proteins are well-known to those of skill in the art of bacterial protein isolation and purification. In certain embodiments, the proteins may be purified, concentrated, admixed with other reagents, or processed to a desired final form. Preferably, the composition will comprise from about 1% to about 90% by weight of the protein, and more preferably from about 5%, to about 50% by weight.

In a preferred embodiment, the protein compositions of the invention may be prepared by a process which comprises the steps of culturing a *Bacillus thuringiensis* cell which expresses an insecticidal IRDIG protein under conditions effective to produce such a protein, and then obtaining the protein from the cell. The obtaining of such a protein may further include purifying, concentrating, processing, or mixing the protein with one or more reagents. Preferably, the insecticidal IRDIG protein toxin is obtained in an amount of from between about 1% to about 90% by weight and more preferably from about 5% to about 50% by weight.

The invention also relates to a method of preparing an insecticidal IRDIG protein composition. Such a method generally involves the steps of culturing a *Bacillus thuringiensis* cell which expresses an insecticidal IRDIG protein toxin under conditions effective to produce the protein, and then obtaining the protein so produced. In a preferred embodiment the *Bacillus thuringiensis* cell is any *Bacillus thuringiensis* cell which contains an insecticidal IRDIG protein gene segment. Alternatively, the recombinant plasmid vectors of the invention may be used to transform other suitable bacterial or eukaryotic cells to produce the protein of the invention. Prokaryotic host cells including Gram-negative cells such as *E. coli, Pseudomonas fluorescens* and related Enterobacteraceae, or Gram-positive cells such as *Bacillus* spp. (including *B. megaterium, B. subtilis*, and *B. thuringiensis*) and the like are all contemplated to be useful in the preparation of the insecticidal IRDIG proteins of the invention. Particularly preferred are the commonly used *E. coli* and *Pseudomonas fluorescens* expression strains.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of peptides or epitopic core regions, such as may be used to generate anti-protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NOs:2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, 122, 124, or 126.

In yet another aspect, the present invention provides methods for producing a transgenic cell, and in particular a plant cell which expresses a nucleic acid segment encoding the novel insecticidal IRDIG proteins of the present invention. The process of producing transgenic cells is well-known in the art. In general, the method comprises transforming a suitable host cell with a DNA segment which contains a promoter operatively linked to a coding region that encodes an insecticidal IRDIG protein toxin. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant protein expressed in a particular transgenic cell, the invention also provides for the expression of protein antisense mRNA. The use of antisense mRNA as a means of controlling or decreasing the amount of a given protein of interest in a cell is well-known in the art.

In a preferred embodiment, the invention encompasses a plant cell which has been transformed with a nucleic acid segment of the invention, and which expresses a gene or gene segment encoding one or more of the novel polypeptide compositions disclosed herein. As used herein, the term “transgenic plant cell” is intended to refer to a plant cell that has incorporated DNA sequences, including but not limited to genes which are perhaps not normally present, DNA sequences not normally transcribed into RNA or translated into a protein (“expressed”), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of an insecticidal IRDIG protein toxin-expressing transgene. In some instances, more than one transgene may be incorporated into the genome of the transformed host plant cell. Such is the case when more than one protein-encoding DNA segment is incorporated into the genome of such a plant. In certain situations, it may be desirable to have one, two, three, four, or even more *B. thuringiensis* crystal proteins or other insecticidal IRDIG proteins or nucleic acids incorporated and stably expressed in the transformed transgenic plant. In preferred embodiments, the introduction of the transgene into the genome of the plant cell results in a stable integration wherein the offspring of such plants also contain a copy of the transgene in their genome. The inheritability of this genetic element by the progeny of the plant into which the gene was originally introduced is a preferred aspect of this invention.

A gene encoding an insecticidal IRDIG protein of the invention may be stably introduced into the genome of a plant cell using well-known methods which is then regenerated into a whole fertile plant. Such plants are highly desirable to growers to protect against crop damage caused by Coleoptera, especially WCR, feeding.

Means for transforming a plant cell and the preparation of a transgenic cell line are well-known in the art (as exemplified in U.S. Pat. Nos. 5,550,318; 5,508,468; 5,482,852; 5,384,253; 5,276,269; and 5,225,341, all specifically incorporated herein by reference), and are briefly discussed herein. Vectors, plasmids, cosmids, YACs (yeast artificial chromosomes), and DNA segments for use in transforming such cells will, of course, generally comprise either the operons, genes, or gene-derived sequences of the present invention, either native, or synthetically-derived, and particularly those encoding the disclosed proteins. These DNA or nucleic acid constructs can further include structures such as promoters, enhancers, polylinkers, or even gene sequences which have positively- or negatively-regulating activity upon the particular genes of interest as desired. The DNA segment or gene may encode either a native or modified protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding an insecticidal IRDIG protein which is toxic to insects. Particularly preferred plants include corn, wheat, soybeans, cotton, turf grasses, ornamental plants, fruit trees, shrubs, vegetables, grains, legumes, and the like, or any plant into which introduction of a insecticidal IRDIG protein transgene is desired.

In a related aspect, the present invention also encompasses a seed produced by the transformed plant, a progeny from such seed, and a seed produced by the progeny of the original transgenic plant, produced in accordance with the above process. Such progeny and seeds will have a protein encoding transgene stably incorporated into its genome, and such progeny plants will inherit the traits afforded by the introduction of a stable transgene in Mendelian fashion. All such transgenic plants having incorporated into their genome transgenic DNA segments encoding an insecticidal IRDIG protein toxin are aspects of this invention.

In particular embodiments, the inventors contemplate the use of antibodies, either monoclonal or polyclonal which bind to the proteins disclosed herein. Means for preparing and characterizing antibodies are well known in the art.

The present invention also provides compositions, methods and kits for screening samples suspected of containing an insecticidal IRDIG protein toxin or a gene encoding such a toxin. Such screening may be performed on samples such as transformed host cells, transgenic plants, progeny or seed thereof, or laboratory samples suspected of containing or producing such a polypeptide or nucleic acid segment. A kit can contain a novel nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent that may be provided.

In still further embodiments, the present invention concerns immunodetection methods and associated kits. It is proposed that the proteins or peptides of the present invention may be employed to detect antibodies having reactivity therewith, or, alternatively, antibodies prepared in accordance with the present invention, may be employed to detect proteins or protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a protein or peptide or a protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of proteins or related peptides and/or antibodies in a sample. Samples may include cells, cell supernatants, cell suspensions, cell extracts, enzyme fractions, protein extracts, or other cell-free compositions suspected of containing proteins or peptides. Generally speaking, kits in accordance with the present invention will include a suitable protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquoted. The kits of the present invention will also typically include a means for containing the antibody, antigen, and reagent containers in close confinement for commercial sale. Such containers may include injection or blow-molded plastic containers into which the desired vials are retained.

ELISAs and Immunoprecipitation

ELISAs may be used in conjunction with the invention. In an ELISA assay, proteins or peptides incorporating protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/TWEEN® surface active agent (ICI Americas, Inc., Wilmington, Del.). These added agents also tend to assist in the reduction of nonspecific background. The layered antisera is then allowed to incubate for from about 2 to about 4 hours, at temperatures preferably on the order of about 25° C. to about 27° C. Following incubation, the antisera-contacted surface is washed so as to remove non-immunocomplexed material. A preferred washing procedure includes washing with a solution such as PBS/TWEEN® surface active agent, or borate buffer.

Following formation of specific immunocomplexes between the test sample and the bound antigen, and subsequent washing, the occurrence and even amount of immunocomplex formation may be determined by subjecting to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS/TWEEN®) surface active agent.

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-protein antibodies of the present invention are particularly useful for the isolation of other protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Non-ionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immuno-precipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

The present invention is also directed to protein or peptide compositions, free from total cells and other peptides, which comprise a purified protein or peptide which incorporates an epitope that is immunologically cross-reactive with one or more anti-protein antibodies. In particular, the invention concerns epitopic core sequences derived from insecticidal IRDIG proteins or peptides.

As used herein, the term "incorporating an epitope(s) that is immunologically cross-reactive with one or more anti-protein antibodies" is intended to refer to a peptide or protein antigen which includes a primary, secondary, or tertiary structure similar to an epitope located within a protein or polypeptide. The level of similarity will generally be to such a degree that monoclonal or polyclonal antibodies directed against the protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Cry immunodominant epitopes, or their functional equivalents, is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified or extended epitopic/immunogenic core sequences which result in a "universal" epitopic peptide directed to proteins, and in particular insecticidal and insecticidal-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins. Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

The inventors contemplate that the protein compositions disclosed herein will find particular utility as insecticides for topical or systemic application to field crops, grasses, fruits and vegetables, and ornamental plants. In a preferred embodiment, the bioinsecticide composition comprises an oil flowable suspension of bacterial cells which expresses a novel protein disclosed herein. Preferably the cells are *B. thuringiensis*, however, any such bacterial host cell expressing the novel nucleic acid segments disclosed herein and producing a protein is contemplated to be useful, including but not limited to *B. megaterium, B. subtilis, E. coli,* or *Pseudomonas* spp.

In another important embodiment, the bioinsecticide composition comprises a water dispersible granule. This granule comprises bacterial cells which expresses a novel protein disclosed herein. Preferred bacterial cells are *B. thuringiensis* cells, however, bacteria such as *B. megaterium, B. subtilis, E. coli,* or *Pseudomonas* spp. cells transformed with a DNA segment disclosed herein and expressing the protein are also contemplated to be useful.

In a third important embodiment, the bioinsecticide composition comprises a wettable powder, dust, pellet, or collodial concentrate. This powder comprises bacterial cells which expresses a novel protein disclosed herein. Preferred bacterial cells are *B. thuringiensis* cells, however, bacteria such as *B. megaterium, B. subtilis, E. coli,* or *Pseudomonas* spp. cells transformed with a DNA segment disclosed herein and expressing the protein are also contemplated to be useful. Such dry forms of the insecticidal compositions may be formulated to dissolve immediately upon wetting, or alternatively, dissolve in a controlled-release, sustained release, or other time-dependent manner.

In a fourth important embodiment, the bioinsecticide composition comprises an aqueous suspension of bacterial cells such as those described above which express the protein. Such aqueous suspensions may be provided as a concentrated stock solution which is diluted prior to application, or alternatively, as a diluted solution ready-to-apply.

For these methods involving application of bacterial cells, the cellular host containing the protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel insecticidal IRDIG proteins or insecticidal IRDIG protein-derived toxins may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the protein and apply solutions, suspensions, or collodial preparations of such crystals and/or spores as the active bioinsecticidal composition.

Regardless of the method of application, the amount of the active component(s) are applied at an insecticidally-effective amount, which will vary depending on such factors as, for example, the specific insects to be controlled, the specific plant or crop to be treated, the environmental conditions, and the method, rate, and quantity of application of the insecticidally-active composition.

The insecticide compositions described may be made by formulating the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target insect, typically onto the foliage and in the rhizosphere (the soil surrounding plant roots) of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or soil application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

Modification and changes may be made in the primary structure of the toxins of the present invention to produce derivatives, analogs and mutants and DNA segments which encode them and still obtain a functional insecticidal molecule that encodes a protein or peptide with desirable characteristics. In particular embodiments of the invention, mutated proteins are contemplated to be useful for increasing the insecticidal activity of the protein, and consequently increasing the insecticidal activity or expression of the recombinant transgene in a plant cell. The amino acid changes may be achieved by changing the codons of the nucleic sequence, according to the codons given in Table 2.

TABLE 2

| Amino Acids | Abbre-viation | Abbre-viation | Codons |
|---|---|---|---|
| Alanine | Ala | A | GCA GCC GCG GCU |

TABLE 2-continued

| Amino Acids | Abbre-viation | Abbre-viation | Codons |
|---|---|---|---|
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected protein gene sequence, e.g., a sequence such as that shown in SEQ ID NOs:1, 3, 5, 7, 9, 11, 13, 15, 17, 19, 21, 23, 25, 27, 29, 31, 33, 35, 37, 39, 41, 43, 45, 69, 70, 72, 74, 76, 81, 83, 85, 87, 89, 91, 93, 95, 97, 99, 101, 103, 105, 107, 109, 111, 113, 115, 117, 119, and 121. The ability of such nucleic acid probes to specifically hybridize to a protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a protein gene from *B. thuringiensis* using PCR™ technology. Segments of related protein genes from other species may also be amplified by PCR™ using such primers.

The present invention contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region.

As used herein, the term "operatively linked" means that a promoter is connected to a coding region in such a way that the transcription of that coding region is controlled and regulated by that promoter. Means for operatively linking a promoter to a coding region are well known in the art.

In a preferred embodiment, the recombinant expression of DNAs encoding the proteins of the present invention is preferable in a *Bacillus* host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus* crystal proteins include any of the known crystal protein gene promoters, including the insecticidal IRDIG protein gene promoter, and promoters specific for *B. thuringiensis* sigma factors, such as $\sigma^E$ and $\sigma^K$. Alternatively, mutagenized or recombinant crystal protein-encoding gene promoters may be engineered by the hand of man and used to promote expression of the novel gene segments disclosed herein.

In an alternate embodiment, the recombinant expression of DNAs encoding the proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive, and temporally regulated, spatially regulated, and spatio-temporally regulated.

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the seeds (e.g., zein, oleosin, lectin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Exemplary tissue-specific promoters are corn sucrose synthetase 1, corn alcohol dehydrogenase 1, corn light harvesting complex, corn heat shock protein, pea small subunit RuBP Carboxylase, Ti plasmid mannopine synthase, Ti plasmid nopaline synthase, petunia chalcone isomerase, bean glycine rich protein 1, CaMV 35s transcript and Potato patatin. Preferred promoters are the cauliflower mosaic virus (CaMV 35S) promoter and the S-E9 small subunit RuBP carboxylase promoter.

Under certain circumstances it may be desirable to use an inducible promoter. An inducible promoter is responsible for expression of genes in response to a specific signal, such as: physical stimulus (e.g., heat shock genes); light (e.g., RUBP carboxylase); hormone (e.g., glucocorticoid); antibiotic (e.g., tetracycline); metabolites; and stress (e.g., drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

An expression vector containing a coding region that encodes a polypeptide of interest is engineered to be under control of the lectin promoter and that vector is introduced into plants using, for example, a protoplast transformation method. The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens*. However, several other plant integrating vector systems are known to function in plants including pCaM-VCN transfer control vector. Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptll) and nopaline synthase 3' non-translated region.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably an insecticidal IRDIG protein toxin-encoding gene.

A bacterium, a yeast cell, plant cell, or a plant transformed with an expression vector of the present invention is also contemplated. A transgenic bacterium, yeast cell, plant cell, or plant derived from such a transformed or transgenic cell is also contemplated. Means for transforming bacteria and yeast cells are well known in the art. Typically, means of transformation are similar to those well-known means used to transform other bacteria or yeast such as *E. coli* or *Saccharomyces cerevisiae*.

Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts, by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods; (2) physical methods such as microinjection, electroporation and the gene gun; (3) viral vectors; and (4) receptor-mediated mechanisms.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced insecticidal activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments.

Application of these systems to different plant strains depends upon the ability to regenerate that particular plant strain from protoplasts. Illustrative methods for the regeneration of cereals from protoplasts are described (WO 1997/013843 A1).

To transform plant strains that cannot be successfully regenerated from protoplasts, other ways to introduce DNA into intact cells or tissues can be utilized. For example, regeneration of cereals from immature embryos or explants can be effected. In addition, "particle gun" or high-velocity microprojectile technology can be utilized.

Using that latter technology, DNA is carried through the cell wall and into the cytoplasm on the surface of small metal particles. The metal particles penetrate through several layers of cells and thus allow the transformation of cells within tissue explants.

By transforming a suitable host cell, such as a plant cell, with a recombinant insecticidal IRDIG protein encoding gene-containing segment, the expression of the encoded protein (i.e., a bacterial protein or polypeptide having insecticidal activity against coleopterans) can result in the formation of insect-resistant plants.

By way of example, one may utilize an expression vector containing a coding region for a *B. thuringiensis* protein and an appropriate selectable marker to transform a suspension of embryonic plant cells, such as wheat or corn cells using a method such as particle bombardment to deliver the DNA coated on microprojectiles into the recipient cells. Transgenic plants are then regenerated from transformed embryonic calli that express the insecticidal IRDIG proteins.

The formation of transgenic plants may also be accomplished using other methods of cell transformation which are known in the art such as *Agrobacterium*-mediated DNA transfer. Alternatively, DNA can be introduced into plants by direct DNA transfer into pollen, by injection of the DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art. This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art. In this procedure, transformants are cultured in the presence of a selection agent and in a medium that induces the regeneration of shoots in the plant strain being transformed as described.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., an insecticidal gene) that encodes the polypeptide of interest. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against insects, preferably in the field, under a range of environmental conditions. The inventors contemplate that the present invention will find particular utility in the creation of transgenic plants of commercial interest including corn and various turf grasses, wheat, corn, rice, barley, oats, a variety of ornamental plants and vegetables, as well as a number of nut- and fruit-bearing trees and plants.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

All percentages are by weight and all solvent mixture proportions are by volume unless otherwise noted. All temperatures are in degrees Celsius.

Example 1

Isolation of the Genes Encoding Insecticidal IRDIG Proteins

Nucleic acids encoding the insecticidal IRDIG proteins were isolated from various B.t. strains. Forward and reverse primers for Polymerase Chain Reaction (PCR) were designed and used to amplify nucleotide sequences encoding the full-length insecticidal IRDIG proteins (Table 3). The amplified fragments were subcloned into a protein expression vector backbone. BLAST searches of these gene sequences against NCBI, Pfam and GenomeQuest databases did not return any significant hits. These sequence search results indicate that these genes are novel among all known protein sequences.

Standard cloning methods were used in the construction of *Pseudomonas fluorescens* (Pf) expression plasmids engineered to produce full-length insecticidal IRDIG protein toxins encoded by native and plant-optimized coding regions (described below). Restriction endonucleases were obtained from New England BioLabs (NEB; Ipswich, Mass.) and T4 DNA Ligase (NEB; Ipswich, Mass.) was used for DNA ligation. DNA fragments were purified using a QIAquick® Gel Extraction Kit (Qiagen, Venio, Limburg) after agarose Tris-acetate gel electrophoresis. Plasmid preparations were performed using the NucleoSpin® Plasmid Kit (Macherey-Nagel Inc, Bethlehem, Pa.) following the instructions of the suppliers for low-copy plasmid purification or the Qiagen Plasmid Plus Midi Kit® (Qiagen, Hilden, Germany).

All insecticidal IRDIG proteins were analyzed phylogenetically and non-redundant representative proteins were selected for WCR activity validation. The open reading frame (ORF) sequences of unique representative insecticidal IRDIG proteins were identified. These ORFs were amplified through PCR using the genomic DNAs isolated from the wild-type B.t. strains containing the target insecticidal IRDIG proteins as a template and using the primers listed in Table 3.

TABLE 3

Primers used for PCR to amplify the open reading frames of insecticidal IRDIG proteins for cloning and expression in either Bt or Pf

| IRDIG # | Primer ID | Sequence | SEQ ID NO |
|---|---|---|---|
| 28674 | 28674F | GTGTACTAGTATGGATAATCATTTTTTAGATTTAATCTCAAAAG | 47 |
| | 28674R | TCTCCTCGAGTTAAGCTCTACCATCATAATGTAAATCATATTTTTGAC | 48 |
| 28672 | 28672F | GTGTACTAGTATGAATAACCAGTTATTAGATTTACTGTCAAAAACTC | 49 |
| | 28672R | TCTCCTCGAGTTAAGCTCTGCCATCATAATGTAAATCATATTTTTGAC | 50 |
| 28680 | 28680F | GTGTACTAGTATGGCAACAGTTAGCGGAAAAATAATAATAAATAC | 51 |

TABLE 3-continued

Primers used for PCR to amplify the open reading frames of insecticidal IRDIG proteins for cloning and expression in either Bt or Pf

| IRDIG # | Primer ID | Sequence | SEQ ID NO |
|---|---|---|---|
| | 28680R | TCTCCTCGAGTTAATTACTACTGTCATATTTTAAAATATATTTTTGTCCAAGC | 52 |
| 28682 | 28682F | GTGTACTAGTATGAATAATACATTATTGGAATTACTTTCAAAAATAAAAAAAGAATTCTTTGG | 53 |
| | 28682R | TCTCCTCGAGTTAAGCTCTACCTTTGTATTGTAATGTATATCTTTCTC | 54 |
| 28684 | 28684F | GTGTACTAGTATGAATAATACATTATTGGAATTACTTTCAAAAATAAAAAAAGAATTCTTTGG | 55 |
| | 28684R | TCTCCTCGAGTTAAGCTCTACCTTTGTATTGTAATGTATATCTTTCTCC | 56 |
| 28686 | 28686F | GTGTACTAGTATGAATAACACATTATTGGAATTACTTTCAAAAATAAAAAAAGAATTCTTTGG | 57 |
| | 28686R | TCTCCTCGAGTTAAGCCCTACCTTTGTATTGTAATGTATATCTTTCTCC | 58 |
| 28688 | 28688F | GTGTACTAGTATGTATATGAATAATACATTATTGGAATTACTTTCAAAAATAAAAAAAGAATTCTTTGG | 59 |
| | 28688R | TCTCCTCGAGTTAAGCTCTACCTTTGTATTGTAATGTATATCTTTCTCC | 60 |
| 28696 | 28696F | GTGTACTAGTATGAAGAAAAGATTTTCTGCCGTATCG | 61 |
| | 28696R | TCTCCTCGAGTTAACGCGGGCTTAATGTATAGGTTT | 62 |
| 29779 | 29779FSpeI | GTGTACTAGTATGGATAATAATTTATTATATTTAATTTCAAAAATCCAAACC | 63 |
| | 29779RXhoI | TCTCCTCGAGTTATTGTTTAGTTAAAGTATAATTTTCTTTAGATACCTTAAC | 64 |
| 29781 | 29781FXbaI | GTGTTCTAGAATGAAAGAAGGAGTGTTTAAATTGAAAAAAGG | 65 |
| | 29781RXhoI | TCTCCTCGAGTTAGCGTGGAGCTAATGTATAGGTTTCAC | 66 |
| 28678 | 28678FXbaI | GTGTTCTAGAATGGATAATCATTTATTAGAGTTACTTTTAAAAGTTCAAAAC | 67 |
| | 28678RPstI | GTCACTGCAGTTAAGCTCTACCATCATATTTTAAAGTATATCTTTCTCC | 68 |

Example 2

Design of a Plant Codon-Optimized Insecticidal Toxin Gene

One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO1997013402, U.S. Pat. Nos. 6,166,302, and 5,380,831.

A DNA sequence having a maize codon bias was designed and synthesized to produce an insecticidal IRDIG protein in transgenic monocot plants. A codon usage table for maize (*Zea mays* L.) was calculated from hundreds of protein coding sequences obtained from sequences deposited in GenBank (www.ncbi.nlm.nih.gov). A rescaled maize codon set was calculated after omitting any synonymous codon used less than about 10% of total codon uses for that amino acid.

Further refinements of the sequences were made to eliminate undesirable restriction enzyme recognition sites, potential plant intron splice sites, long runs of A/T or C/G residues, and other motifs that might interfere with mRNA stability, transcription, or translation of the coding region in plant cells. Other changes were made to introduce desired restriction enzyme recognition sites, and to eliminate long internal Open Reading Frames (frames other than +1). These changes were all made within the constraints of retaining the maize-biased rescaled codon composition. The maize-optimized DNA sequences encoding insecticidal toxins are disclosed as SEQ ID NOs:69, 70, 72, 74, and 76.

The foregoing provides several embodiments of the isolated polynucleotide(s) according to the invention, including polynucleotides that are codon-optimized for expression of insecticidal toxin polypeptides of the invention.

Example 3

Construction of Expression Plasmid Encoding Insecticidal IRDIG Protein Toxins in Bacterial Hosts Standard cloning methods were used in the construction of *Pseudomonas fluorescens* (Pf) expression plasmids engineered to produce the insecticidal IRDIG protein toxins encoded by either the native or the maize-optimized coding sequences. Restriction endonucleases were obtained from New England BioLabs (NEB; Ipswich, Mass.) and T4 DNA Ligase (Invitrogen) was used for DNA ligation. Plasmid preparations were performed using the NucleoSpin® Plasmid Kit (Macherey-Nagel Inc, Bethlehem, Pa.) following the instructions of the supplier. DNA fragments were purified using the QIAQUICK Gel Extraction kit (Qiagen) after agarose Tris-acetate gel electrophoresis. The linearized vector was treated with Antarctic Phosphatase (NEB) to enhance formation of recombinant molecules.

The resulting PCR products lacking the native regulatory element sequences were cloned into pDAB122775 for expression in B.t. host 4Q7 and into pDOW1169 for expression in a Pfhost, respectively. The cloning sites used for both B.t. and Pf systems were XbaI/XhoI or SpeI/XhoI. B.t. expression vector pDAB122775 includes a Cry1Ac crystal protein gene promoter (expressed during B.t. cell sporulation), ribosomal binding site (RBS) and the Cry1Ac terminator, while in pDOW1169 these target gene expressions were driven by Ptac promoter and IPTG induction. pDOW1169 is a low copy plasmid with the RSF1010 origin of replication, a pyrF gene, and a ribosome binding site preceding the restriction enzyme recognition sites into which DNA fragments containing protein coding regions may be introduced (U.S. Pat. No. 7,618,799). If not expressed in either B.t. or Pf, they were cloned into an *E. coli* expression vector such as pET280(Kan) at SpeI/XhoI. Constructs were generated using standard molecular cloning procedures that are well known in the art.

The expression plasmids (pDAB121093, 127479, 127480, 127481, 127482, 127484, 127485, 127486, 127487, 127488, 127489, 127490, 127491) were transformed by electroporation into DC454 (a near wild-type *P. fluorescens* strain having mutations ΔpyrF and lsc::lacIQI), or derivatives thereof, recovered in SOC-Soy hydrolysate medium, and plated on selective medium (M9 glucose agar lacking uracil, Sambrook et al., supra).

Protein expression experiments for these insecticidal IRDIG proteins were performed first in 4Q7 B.t. host and then in DPf10 Pfhost. Briefly, recombinant B.t. cultures were grown in 50 ml of Dow AgroSciences Proprietary medium broth that promotes B.t. bacterial sporulation, in a 250-ml baffled flask at 28° C./180-200 rpm for 24-32 hours. The mixture of the crystals and endospores was harvested by centrifugation at 6,000 g at 4° C. for 15 min and followed by washing in 10 ml of 1M NaCl, 0.1% Triton X-100 solution and then in 35 ml of ionized water. The final pellet was suspended in 2 ml deionized water for WCR feeding assays. The B.t. 4Q7 transformed with empty vector pDAB122775 was included as a negative control.

The transformation and selection methods are generally described available in US Patent Application No. 20060008877, U.S. Pat. No. 7,681,799, and US Patent Application No. 20080058262, incorporated herein by reference. Recombinant colonies were identified by restriction digestion of miniprep plasmid DNA.

Example 4

Preparation of Insecticidal IRDIG Protein Samples

Production of insecticidal IRDIG proteins for characterization and insect bioassay was accomplished by shake-flask-grown *P. fluorescens* strain harboring expression construct strains DPf46314, 48284, 48285, 48286, 48287, 48289, 48290, 48291, 48292, 48293, 48294, 48295, 48296. Stored glycerol stocks of the strain were used to inoculate defined production medium with 9.5% glycerol (Teknova Catalog No. 3D7426, Hollister, Calif.). Expression of the insecticidal gene was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in US Patent Application No. 20060008877. The post- and pre-induction samples were analyzed for target protein expression in both cellular soluble and insoluble fractions following BugBuster® lysis and extraction procedures. To estimate expression levels, densitometry analysis was performed using a GE Image Scanner III (GE Healthcare). Protein bands were detected and quantified using ImageQuant TL software (GE Healthcare) and BSA as a standard. The insecticidal IRDIG protein accumulated in the insoluble fraction of lysed cells as inclusion bodies (IB). The cells were flash frozen in liquid nitrogen and stored at −80 C.

Inclusion Body (IB) Preparation for Insecticidal IRDIG Proteins.

Pf derived cell pastes expressing full length insecticidal IRDIG proteins were transferred from −80° C. storage to room temperature. Approximately 10 g of each was taken out and resuspended in cold lysis buffer (40 mL of 50 mM Tris, 200 mM NaCl, 10% glycerol, 0.5% Triton X-100, 20 mM EDTA, 1 mM DTT, pH 7.5) at 20% w/v. The resuspended pellet was incubated at room temperature while rocking with 0.4 mg/ml lysozyme for 20 minutes. This was followed by adding 0.1 mg/mL DNase with 0.1 M $MgCl_2$ and further incubation at 30° C. in a water bath for 20 minutes. The sample was sonicated using a Branson sonifier for 1 minute, duty cycle-60, output control 4 followed by centrifugation at 16,000 rpm for 30 minutes in a JA-17 rotor. The pellets were resuspended 2 additional times in 20% w/v cold lysis buffer with metal beads. The final two washes were carried out using the lysis buffer in the absence of triton-x-100, the supernatants were colorless and the IB pellets became firm and off-white in color. The inclusion bodies were resuspended in sterile-filtered distilled water containing 10 mM EDTA, pH 8.0, aliquoted into 1.5 mL and frozen at −80° C. until needed.

Inclusion Body Solubilization.

Inclusion bodies were thawed at room temperature in a water bath. The inclusion bodies were brought up to 10 mL in 0.1 M CAPS pH 11 followed by sonication for 1 min at output control 4, duty cycle 40%. The solubilized protein was centrifuged for 20 min at 16,000 rpm in a JA17 rotor. The samples were concentrated by 15 mL Amicon 3K MWCO to give a final volume of about 2 mL and buffer exchanged once by adding 18 mL 10 mM CAPS, pH 11 and concentrating them down to 2 mL. This was followed by desalting on PD10 columns that had been previously equilibrated using 10 mM CAPS pH 11.

Insecticidal IRDIG protein purified from the IB preparations was analyzed by SDS-PAGE. Molecular weight was determined from amino acid sequence. Quantification of target bands was done by comparing densitometric values for the bands against Bovine Serum Albumin (BSA) samples run on the same gel to generate a standard curve.

The foregoing provides isolated polynucleotides, including nucleic acid constructs, and isolated insecticidal polypeptides according to the invention.

Example 5

Insecticidal Activity of Proteins

Insecticidal IRDIG proteins were tested and found to have insecticidal activity on larvae of the coleopteran insect, the western corn rootworm (*Diabrotica virgifera virgifera* LeConte).

Test insects were first instar (<24 hr after eclosion) western corn rootworm (WCR), *Diabrotica virgifera virgifera*. Non-diapausing *Diabrotica virgifera virgifera* eggs (Crop Characteristics, Inc., Farmington, Minn.) were incubated for 10 days at 28° C. and 60% RH. Black head eggs were surface sterilized with 10% formalin following the method by Pleau et al. (2002). Lepidopteran test insects comprised fall armyworm (FAW), *Spodoptera frugiperda* (J. E. Smith), corn earworm (CEW), *Heliothis zea* (Boddie), European corn borer (ECB), *Ostrinia nubilalis* (Hübner), and soybean looper (SBL), *Chrysodeixis includens*.

Proteins were bioassayed using a 48-well WCR bioassay format. In this assay, non-diapausing WCR eggs (Crop Characteristics Inc., Farmington, Minn.) were incubated at 28° C. in soil for 10 days. These eggs were washed from the soil with water, surface sterilized with 10% formaldehyde and triple rinsed with sterile water. These eggs were hatched and fed with a Dow AgroSciences proprietary WCR diet. An overlay diet bioassay was conducted in 48-well titer plates with each well containing 0.75 ml of the artificial WCR diet. Each test aliquot was pipetted at 40 uL/well onto diet surface (0.95 $cm^2$) of 8 wells and dried under room temperature in a laminar flow. The treated diet surface of each well was infested with two *D. virgifera* neonates (24-48 hr old) and test insects were enclosed in the bioassay arena with Breathe Easy® gas permeable sealing membrane for micro titer plates (USA Scientific, Orlando, Fla.). Negative controls were 20 mM sodium citrate buffer, pH 3.5; 10 mM CAPS buffer, pH 11; the positive control was 100 ug/$cm^2$ Cry34/35Ab1 in sodium citrate buffer.

Bioassay trays were held under controlled environmental conditions (28° C., 60% relative humidity, 16:8 h light/dark) for 5 days. The total number of insects exposed to each protein sample, the number of dead insects, and the weight of surviving insects were recorded in all insect bioassays. Larvae which weighed 0.1 mg were considered moribund insects and were included in the percent practical mortality computation. Growth inhibition was calculated as follows:

$$GI=[1-(TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control). Bioassays were conducted under randomized complete block design and replicated at least 4 times, with 16 *D. virgifera virgifera* larvae per replicate. Data were analyzed with ANOVA and mean separation using Tukey HSD (Pr>0.05). When dose response analyses were performed, the growth inhibition concentration-response curves were determined using a non-linear logistic 3-parameter model, and the effective concentrations required to cause 50% growth inhibition ($GI_{50}$) was estimated. These analyses were performed using JMP Pro, version 9.0.3, software (SAS Institute Inc., Cary, N.C.). Probit analyses of the pooled practical mortality data were conducted using POLO-PC (LeOra Software) to estimate the 50% lethal concentration ($LC_{50}$) of the concentration-response curves.

Insecticidal IRDIG proteins were significantly efficacious compared to negative controls. Efficacy of IRDIG28686, 28684 and 28682 at the tested concentrations were comparable to the positive control Cry34/35Ab1 (Table 5).

Table 5 shows the mean percent practical mortality and mean percent growth inhibition of WCR when exposed to various concentrations of insecticidal IRDIG proteins.

TABLE 5

| | | | % Practical mortality | | | % Growth inhibition | | |
|---|---|---|---|---|---|---|---|---|
| Sample name | Rep | Conc. (µg/cm2) | Mean | Std Error | Mean Tukey HSD (p > 0.05) | Mean | Std Error | Mean Tukey HSD (p > 0.05) |
| Cry34/35Ab1 | 18 | 100 | 82.83 | 4.05 | A | 98.69 | 3.55 | A |
| IRDIG28684 | 6 | 23 | 35.75 | 7.02 | BC | 79.15 | 6.15 | AB |
| IRDIG28686 | 6 | 42 | 50.27 | 7.02 | B | 79.12 | 6.15 | AB |

TABLE 5-continued

|  |  |  | % Practical mortality | | | % Growth inhibition | | |
|---|---|---|---|---|---|---|---|---|
| Sample name | Rep | Conc. (µg/cm2) | Mean | Std Error | Tukey HSD (p > 0.05) | Mean | Std Error | Tukey HSD (p > 0.05) |
| IRDIG28682 | 4 | 42 | 26.78 | 8.60 | BCD | 69.45 | 7.53 | ABC |
| IRDIG28688 | 6 | 42 | 49.67 | 7.02 | B | 69.27 | 6.15 | B |
| IRDIG28674 | 4 | 25 | 11.78 | 8.60 | BCD | 61.38 | 7.53 | BCD |
| IRDIG28680 | 4 | 42 | 21.11 | 8.60 | BCD | 56.51 | 7.53 | BCD |
| IRDIG28672 | 4 | 22 | 3.13 | 8.60 | CD | 34.20 | 7.53 | CDE |
| IRDIG27642 | 8 | 42 | 9.54 | 6.08 | CD | 30.59 | 5.32 | DE |
| 10 mM CAPS pH 11 | 18 | 0 | 3.57 | 4.05 | D | 0.00 | 3.55 | F |
| 20 mM NaCitrate pH 3.5 | 18 | 0 | 5.64 | 4.05 | D | 0.00 | 3.55 | F |

[a]Means followed by the same letter within each column are not significantly different according to Tukey HSD (p > 0.05).

Table 6 shows the mean percent practical mortality and mean percent growth inhibition of WCR when exposed to 100 µg/cm² concentrations of insecticidal IRDIG proteins IRDIG27642 and IRDIG28686 were tested in a range of concentrations ranging from 2.6 to 168 µg/cm² and the WCR activity provided sufficient data for dose response analyses

TABLE 6

|  |  |  | % Practical mortality | | | % Growth inhibition | | |
|---|---|---|---|---|---|---|---|---|
| Sample | Rep | Conc (µg/cm2) | Mean | Std Error | Tukey HSD (p > 0.05)[a] | Mean | Std Error | Tukey HSD (p > 0.05)[a] |
| Cry34/35Ab1 | 4 | 100 | 100.0 | 4.6 | A | 100.0 | 3.6 | A |
| IRDIG28682 | 4 | 100 | 81.3 | 6.5 | AB | 94.4 | 5.1 | A |
| IRDIG28686 | 4 | 100 | 81.0 | 6.5 | AB | 93.7 | 5.1 | A |
| IRDIG28684 | 4 | 100 | 70.3 | 6.5 | B | 88.2 | 5.1 | AB |
| IRDIG28688 | 4 | 100 | 75.2 | 6.5 | AB | 84.4 | 5.1 | ABC |
| IRDIG27642 | 4 | 100 | 38.0 | 6.5 | C | 68.4 | 5.1 | BCD |
| IRDIG28674 | 4 | 100 | 32.1 | 6.5 | CD | 66.3 | 5.1 | BCDE |
| IRDIG28672 | 4 | 100 | 28.9 | 6.5 | CD | 63.0 | 5.1 | CDE |
| IRDIG28692 | 4 | 100 | 28.4 | 6.5 | CD | 62.5 | 5.1 | CDE |
| IRDIG28694 | 4 | 100 | 23.6 | 6.5 | CD | 45.5 | 5.1 | DE |
| IRDIG28676 | 4 | 100 | 18.8 | 6.5 | CD | 41.9 | 5.1 | E |
| Na-citrate 20 mM pH 3.5 | 4 | 0 | 3.3 | 6.5 | D | 0.0 | 5.1 | F |
| 10 mM CAPS pH 11 | 4 | 0 | 3.1 | 6.5 | D | 0.0 | 5.1 | F |

[a]Means followed by the same letter within each column are not significantly different according to Tukey HSD (p > 0.05).

IRDIG28682, IRDIG28686, IRDIG28688 showed the highest percent mortality and percent growth inhibition and were not significantly different from the positive control of Cry34/35. IRDIG28684 and IRDIG28642 showed significant mortality and growth inhibition compared to the controls. IRDIG28674, IRDIG28672, IRDIG28692, IRDIG28694, IRDIG28676 showed significant growth inhibition in comparison to the respective controls.

(Tables 6 and 7). There was a significant difference in percent practical mortality of IRDIG28686 at doses of 21, 42, 84, and 168 µg/cm². Significant growth inhibition was determined for IRDIG27642 at doses of 10.5, 42, 84, 168 µg/cm² and for IRDIG28686 at 21, 42, 84, and 168 µg/cm².

Table 7 shows the dose response of insecticidal IRDIG proteins against WCR in a 48 well bioassay format.

TABLE 7

|  |  |  | % Practical mortality | | | % Growth inhibition | | |
|---|---|---|---|---|---|---|---|---|
| Sample name | Conc. (ug/cm2) | Rep | Mean | Std Error | Tukey HSD (p > 0.05)[a] | Mean | Std Error | Tukey HSD (p > 0.05)[a] |
| 10 mM CAPS buffer pH 11 | 0 | 8 | 2.5 | 3.1 | E | 2.2 | 6.0 | FG |
| 20 mM Sodium citrate buffer | 0 | 8 | 6.9 | 3.1 | DE | 0.0 | 6.0 | G |

TABLE 7-continued

| | | | % Practical mortality | | | % Growth inhibition | | |
|---|---|---|---|---|---|---|---|---|
| Sample name | Conc. (ug/cm2) | Rep | Mean | Mean Std Error | Tukey HSD (p > 0.05)[a] | Mean | Mean Std Error | Tukey HSD (p > 0.05)[a] |
| pH 3.5 | | | | | | | | |
| Cry34/35Ab1 | 100 | 8 | 98.3 | 3.1 | A | 99.8 | 6.0 | A |
| IRDIG27642 | 2.625 | 4 | 0.0 | 4.4 | E | 9.6 | 8.4 | EFG |
| IRDIG27642 | 5.25 | 4 | 7.2 | 4.4 | DE | 31.2 | 8.4 | CDEFG |
| IRDIG27642 | 10.5 | 4 | 10.1 | 4.4 | DE | 40.3 | 8.4 | CDE |
| IRDIG27642 | 21 | 4 | 7.5 | 4.4 | DE | 38.3 | 8.4 | CDEF |
| IRDIG27642 | 42 | 4 | 9.2 | 4.4 | DE | 53.0 | 8.4 | BCD |
| IRDIG27642 | 84 | 4 | 7.6 | 4.4 | DE | 41.2 | 8.4 | CDE |
| IRDIG27642 | 168 | 4 | 21.8 | 4.4 | CDE | 57.6 | 8.4 | BCD |
| IRDIG28686 | 2.625 | 2 | 3.2 | 6.2 | DE | 4.9 | 11.9 | DEFG |
| IRDIG28686 | 5.25 | 4 | 10.1 | 4.4 | DE | 24.9 | 8.4 | CDEFG |
| IRDIG28686 | 10.5 | 4 | 17.2 | 4.4 | DE | 34.0 | 8.4 | CDEFG |
| IRDIG28686 | 21 | 4 | 25.4 | 4.4 | CD | 50.8 | 8.4 | BCDE |
| IRDIG28686 | 42 | 4 | 42.8 | 4.4 | BC | 65.5 | 8.4 | ABC |
| IRDIG28686 | 84 | 4 | 48.9 | 4.4 | B | 61.6 | 8.4 | BC |
| IRDIG28686 | 168 | 4 | 65.3 | 4.4 | B | 86.2 | 8.4 | AB |

[a]Means followed by the same letter within each column are not significantly different according to Tukey HSD (p > 0.05).

Table 8 shows the $LC_{50}$ and $GI_{50}$ of IRDIG27642 and IRDIG28686 insecticidal IRDIG proteins in 48-well bioassay format.

TABLE 8

| Protein | $LC_{50}$, µg/cm² (95% CI*) | $GI_{50}$, µg/cm² (95% CI*) |
|---|---|---|
| IRDIG28686 | 78.4 (58.0-116.6) | 22.6 (11.4-44.7) |
| IRDIG27642 | >168 | 74.2 (25.2-218.1) |

*CI = Confidence interval

Table 9 shows percent practical mortality and percent growth inhibition of WCR when exposed to 33 µg/cm² concentrations of IRDIG proteins.

TABLE 9

| | | % Practical mortality | | | % Growth inhibition | | |
|---|---|---|---|---|---|---|---|
| Sample | Conc (ug/cm²) | Mean | SE | Tukey HSD (Pr > 0.05) | Mean | SE | Tukey HSD (Pr > 0.05) |
| Cry34/35Ab1 | 100 | 100.0 | 5.3 | A | 100.0 | 6.4 | A |
| IRDIG28686 | 33 | 61.8 | 7.5 | B | 79.9 | 9.1 | AB |
| IRDIG28682 | 33 | 57.6 | 7.5 | BC | 78.8 | 9.1 | AB |
| IRDIG28684 | 33 | 53.0 | 7.5 | BCD | 76.4 | 9.1 | AB |
| IRDIG28688 | 33 | 45.8 | 7.5 | BCDE | 62.4 | 9.1 | ABC |
| IRDIG28674 | 33 | 25.0 | 7.5 | BCDEF | 57.3 | 9.1 | BC |
| IRDIG27642 | 33 | 23.7 | 7.5 | CDEF | 55.8 | 9.1 | BC |
| IRDIG28672 | 33 | 12.8 | 7.5 | EF | 30.9 | 9.1 | CD |
| IRDIG28692 | 33 | 19.3 | 7.5 | DEF | 29.9 | 9.1 | CD |
| IRDIG28694 | 33 | 23.5 | 7.5 | CDEF | 29.5 | 9.1 | CD |
| IRDIG28676 | 33 | 7.8 | 7.5 | F | 26.8 | 9.1 | CD |
| Na-citrate 20 mM pH 3.5 | 0 | 3.3 | 7.5 | F | 0.0 | 9.1 | D |
| 10 mM CAPS pH 11 | 0 | 3.1 | 7.5 | F | 0.0 | 9.1 | D |

IRDIG28686, IRDIG28682, IRDIG 28684, and IRDIG 28688 exhibited similar growth inhibition as the positive control. IRDIG28674 and IRDIG28646 showed a significant difference in growth inhibition when compared to controls. Percent mortality for IRDIG28686, IRDIG28682, IRDIG 28684, and IRDIG 28688 were significantly different than the controls.

Table 10 shows percent practical mortality and percent growth inhibition of WCR when exposed to 11 µg/cm² concentrations of IRDIG proteins.

TABLE 10

| | | % Practical mortality | | | % Growth inhibition | | |
|---|---|---|---|---|---|---|---|
| Sample | Conc (ug/cm²) | Mean | SE | Tukey HSD (Pr > 0.05) | Mean | SE | Tukey HSD (Pr > 0.05) |
| Cry34/35Ab1 | 100 | 100.0 | 4.2 | A | 100.0 | 8.2 | A |
| IRDIG28686 | 11 | 53.2 | 6.0 | B | 72.9 | 11.6 | AB |
| IRDIG28684 | 11 | 27.1 | 6.0 | BCD | 59.6 | 11.6 | ABC |
| IRDIG28682 | 11 | 33.6 | 6.0 | BC | 51.2 | 11.6 | ABCD |
| IRDIG28676 | 11 | 20.3 | 6.0 | CD | 43.3 | 11.6 | BCD |
| IRDIG28688 | 11 | 11.3 | 6.0 | CD | 34.2 | 11.6 | BCD |
| IRDIG27642 | 11 | 12.5 | 5.3 | CD | 33.0 | 10.4 | BCD |
| IRDIG28692 | 11 | 9.4 | 6.0 | CD | 29.0 | 11.6 | BCD |
| IRDIG28672 | 11 | 8.6 | 6.0 | CD | 28.1 | 11.6 | BCD |
| IRDIG28674 | 11 | 11.2 | 6.0 | CD | 21.3 | 11.6 | BCD |
| IRDIG28694 | 11 | 11.0 | 6.0 | CD | 13.9 | 11.6 | CD |
| Na-citrate 20 mM pH 3.5 | 0 | 3.3 | 6.0 | D | 0.0 | 11.6 | D |
| 10 mM CAPS pH 11 | 0 | 3.1 | 6.0 | D | 0.0 | 11.6 | D |

Percent practical mortality was significantly higher for IRDIG28686 and IRDIG28682 compared to the controls. Percent growth inhibition was significantly higher for IRDIG28686 and IRDIG 28684.

For Lepidoptera, bioassays were conducted in 128-well bioassay trays (C-D International, Pitman, N.J.). A 40 uL aliquot of protein sample was delivered onto the surface of multispecies lepidopteran diet (Southland Products, Lake Village, Ark.) in each well. The treated trays were air dried, and one individual larva (24 to 48 h after eclosion) was deposited on the treated diet surface. Each sample was tested with eight larvae per replication. There were two to three replications performed. The infested wells were then sealed with adhesive sheets of clear plastic vented to allow gas exchange (C-D International, Pitman, N.J.). Negative controls were untreated diet surface, water, 10 mM CAPS buffer, pH 10.5 and 9 ug/cm$^2$ BSA in CAPS buffer, the positive control was 0.03 ug/cm$^2$ Cry1A in CAPS buffer and 0.12 μg/cm$^2$ Cry1Fa in CAPS buffer.

Enriched insecticidal IRDIG proteins from inclusion bodies was tested on lepidopteran insects, methods similar to those described above were followed for *Helicoverpa zea* (corn earworm (CEW)), *Ostrinia nubilalis* (European corn borer (ECB)), *Spodoptera frugiperda* (fall armyworm (FAW)), and *Chrysodeixis includens* (soybean looper (SBL)). IRDIG27642 insecticidal toxin activity was not significantly different in mortality or growth inhibition from the negative controls.

The foregoing describes a method of applying an isolated insecticidal polypeptide and controlling a coleopteran pest population in accordance with the invention.

Example 6

Insecticidal Activity of Proteins on Cry3Bb-Resistant WCR

The insecticidal IRDIG proteins are bioassayed with larvae generated from a selected and a non-selected Cry3Bb WCR strains, as well as a non-diapausing WCR control line. The non-diapausing WCR control eggs (Crop Characteristics Inc., Farmington, Minn.), Cry3Bb selected WCR eggs (Meihls et al., 2008 and 2012) and Cry3Bb non-selected WCR eggs are processed similarly as described above in preparation for a 48-well WCR bioassay format. The Cry3Bb non-selected eggs are an unexposed lab population, originating from South Dakota.

Percent practical mortality (dead plus moribund insects) and growth inhibition are calculated. Control mortality should not exceed 20%. Bioassays are conducted under completely randomized design and replicated 3-4 times, with 16 *D. virgifera virgifera* larvae per replicate. Percent practical mortality and growth inhibition are analyzed with a one-way analysis of variance (ANOVA) and mean separations by using the Tukey-Kramer HSD test (P>0.05).

Example 7

Protein Processing by WCR Midgut Fluid and Corn Root Juice

Midgut Fluid Collection.

Approximately 150 third instar western corn rootworm (WCR) larvae were ordered from Crop Characteristics. The insects were shipped with corn roots. Under a light microscope, using a scalpel, both the posterior and anterior ends of the larvae were removed. Using forceps, the gut was pulled out and stored in the buffer (0.15 M NaCl filtered and sterile buffer containing 8.5% sucrose) and kept on ice.

Procedure for Protein Digestion by WCR Midgut Fluid.

Western corn rootworm (WCR) active protein (IRDIG) stability was analyzed in the presence of 12 μg WCR gut juice to determine potential cleavage (activation or inactivation) sites. Proteins expressed and purified from *Pseudomonas* were incubated with WCR gut juice or extract for 20 hr at 30° C. WCR concentrations and pH of 7.5 (50 mM Tris pH 7.5, 0.15 M KCl, 0.015 M CaCl$_2$ final concentration from 10x stock) were chosen based on protease activity testing.

Reactions were stopped with the addition of proteinase inhibitors. Thirty μl of reaction was then mixed 10 μl of LDS buffer (10 mM TCEP) and loaded onto a 4-12% PAGE gel using MES running buffer. Results indicate a significant amount of processing of WCR actives by WCR and maize root extract (MRE). Identical gels were blotted to allow identification of cleavage motifs by Edman N-terminal sequencing.

Procedure for Protein Digestion by Corn Root Juice 100 ug/cm$^2$ of Insecticidal IRDIG27642 protein is treated by WCR midgut fluid and corn root juice are tested against the WCR following the bioassay method of 48-well format, described in Example 5, Insecticidal activity of proteins.

Example 8

*Agrobacterium* Transformation

Standard cloning methods were used in the construction of binary plant transformation and expression plasmid. Restriction endonucleases and T4 DNA Ligase were obtained from NEB. Plasmid preparations were performed using the NucleoSpin® Plasmid Preparation kit or the NucleoBond® AX Xtra Midi kit (both from Macherey-Nagel), following the instructions of the manufacturers. DNA fragments were purified using the QIAquick PCR Purification Kit or the QIAEX II Gel Extraction Kit (both from Qiagen) after gel isolation.

DNA comprising a nucleotide sequence that encodes an insecticidal IRDIG protein was synthesized by a commercial vendor (e.g., DNA2.0, Menlo Park, Calif.) and was supplied as cloned fragments in plasmid vectors. Other DNA sequences encoding other insecticidal IRDIG proteins were obtained by standard molecular biology manipulation of constructs containing appropriate nucleotide sequences.

Full-length or modified coding sequences (CDS) for insecticidal IRDIG proteins were subcloned into a plant expression plasmid at appropriate sites. The resulting plant expression cassettes containing the appropriate coding region under the control of plant expression elements, (e.g., plant expressible promoters, 3' terminal transcription termination and polyadenylate addition determinants, and the like) were subcloned into a binary vector plasmid, utilizing, for example, Gateway® technology or standard restriction enzyme fragment cloning procedures. LR Clonase™ (Invitrogen) for example, may be used to recombine the full-length and modified gene plant expression cassettes into a binary plant transformation plasmid if the Gateway® technology is utilized. The binary plant transformation vector included a bacterial selectable marker gene that confers resistance to the antibiotic spectinomycin when the plasmid is present in *E. coli* and *Agrobacterium* cells. The binary vector plasmid also included a plant-expressible selectable marker gene that is functional in the desired host plants, namely, the aminoglycoside phosphotransferase gene of transposon Tn5 (aphII) which encodes resistance to the antibiotics kanamycin, neomycin and G418.

Electro-competent cells of *Agrobacterium tumefaciens* strain Z707S (a streptomycin-resistant derivative of Z707) were prepared and transformed using electroporation (Weigel and Glazebrook, 2002). After electroporation, 1 mL of YEP broth (gm/L: yeast extract, 10; peptone, 10; NaCl, 5) was added to the cuvette and the cell-YEP suspension was transferred to a 15 mL culture tube for incubation at 28° C. in a water bath with constant agitation for 4 hours. The cells were plated on YEP plus agar (25 gm/L) with spectinomycin (200 μg/mL) and streptomycin (250 μg/mL) and the plates were incubated for 2-4 days at 28° C. Well separated single colonies were selected and streaked onto fresh YEP+agar plates with spectinomycin and streptomycin, and incubated at 28° C. for 1-3 days.

The presence of the insecticidal toxin gene insert in the binary plant transformation vector was confirmed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before was extracted using Qiagen Spin Mini Preps, performed per manufacturer's instructions. Plasmid DNA from the binary vector used in the *Agrobacterium* electroporation transformation was included as a control. The PCR reaction was completed using Taq DNA polymerase from Invitrogen per manufacturer's instructions at 0.5× concentrations. PCR reactions were carried out in a MJ Research Peltier Thermal Cycler programmed with the following conditions: Step 1) 94° C. for 3 minutes; Step 2) 94° C. for 45 seconds; Step 3) 55° C. for 30 seconds; Step 4) 72° C. for 1 minute per kb of expected product length; Step 5) 29 times to Step 2; Step 6) 72° C. for 10 minutes. The reaction was maintained at 4° C. after cycling. The amplification products were analyzed by agarose gel electrophoresis (e.g., 0.7% to 1% agarose, w/v) and visualized by ethidium bromide staining. A colony was selected whose PCR product was identical to the plasmid control.

Another binary plant transformation vector containing the insecticidal toxin gene insert was confirmed by restriction digest fingerprint mapping of plasmid DNA prepared from candidate *Agrobacterium* isolates by standard molecular biology methods well known to those skilled in the art of *Agrobacterium* manipulation.

The foregoing discloses nucleic acid constructs comprising a polynucleotide that encodes an insecticidal toxin polypeptide in accordance with the invention.

Example 9

Production of Insecticidal Toxins in Dicot Plants

*Arabidopsis* Transformation

*Arabidopsis thaliana* Col-01 is transformed using the floral dip method (Weigel and Glazebrook, 2002).

The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold BioTechnology, St. Louis, Mo.), 10% (w/v) sucrose, 0.044 μM benzylaminopurine (10 μL/liter of 1 mg/mL stock in DMSO) and 300 μL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

*Arabidopsis* Growth and Selection.

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron™ growth chamber (Models CMP4030 or CMP3244; Controlled Environments Limited, Winnipeg, Manitoba, Canada) under long day conditions (16 hours light/8 hours dark) at a light intensity of 120-150 mol/$m^2$ sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a bar gene, transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron™ growth chamber under the above-mentioned growth conditions.

Those skilled in the art of dicot plant transformation will understand that other methods of selection of transformed plants are available when other plant expressible selectable marker genes (e.g., herbicide tolerance genes) are used.

Insect Bioassays of Transgenic *Arabidopsis*

Transgenic *Arabidopsis* lines expressing insecticidal toxin proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

The foregoing provides methods for making and using transgenic plants comprising insecticidal toxin polypeptides according to the invention.

Example 10

Production of Insecticidal IRDIG Proteins in Monocot Plants

*Agrobacterium*-Mediated Transformation of Maize.

Transgenic maize cells, tissues, and plants that produce one or more insecticidal IRDIG proteins through expression of a chimeric gene stably-integrated into the plant genome are produced following *Agrobacterium*-mediated transformation. Maize transformation methods employing binary transformation vectors are known in the art, as described, for example, in U.S. Pat. No. 8,304,604, which is herein incorporated by reference in its entirety. Transformed tissues are selected by their ability to grow on Haloxyfop-containing medium and are screened for protein production, as appropriate. Portions of such transformed tissue cultures are presented to insect larvae for bioassay, essentially as described in EXAMPLE 5.

Agrobacterium Culture Initiation.

Glycerol stocks of the project vectors in the host *Agrobacterium tumefaciens* strain DAt13192 (RecA minus ternary strain) are obtained from the DAS Recombinant Culture Collection (RCC). *Agrobacterium* cultures are streaked from glycerol stocks onto AB minimal medium and incubated at 20° C. in the dark for 3 days. *Agrobacterium* cultures are then streaked onto a plate of YEP medium and incubated at 20° C. in the dark for 1 day.

On the day of an experiment, a mixture of Inoculation medium and acetosyringone is prepared in a volume appropriate to the number of constructs in the experiment. Inoculation medium is pipetted into a sterile, disposable, 250 ml flask. A 1 M stock solution of acetosyringone in 100% dimethyl sulfoxide is added to the flask containing inoculation medium in a volume appropriate to make a final acetosyringone concentration of 200 µM.

For each construct, 1-2 loops of *Agrobacterium* from the YEP plate are suspended in 15 mL of the inoculation medium/acetosyringone mixture inside a sterile, disposable, 50 mL centrifuge tube and the optical density of the solution at 600 nm ($O.D._{600}$) is measured in a spectrophotometer. The suspension is then diluted down to 0.25-0.35 $O.D._{600}$ using additional Inoculation medium/acetosyringone mixture. The tube of *Agrobacterium* suspension is then placed horizontally on a platform shaker set at about 75 rpm at room temperature for between 1 and 4 hours before use.

Ear Sterilization and Embryo Isolation.

Ears from *Zea mays* cultivar B104 are produced in greenhouse facilities and harvested 10-12 days post pollination. Harvested ears are de-husked and surface-sterilized by immersion in a 20% solution of commercial bleach (Ultra Clorox® Germicidal Bleach, 6.15% sodium hypochlorite) and two drops of soap, for 20 minutes, followed by three rinses in sterile, deionized water inside a laminar flow hood. Immature zygotic embryos (1.8-2.2 mm long) are aseptically excised from each ear and distributed into one or more micro-centrifuge tubes containing 2.0 mL of *Agrobacterium* suspension into which 2 µl of 10% Break-Thru® 5233 surfactant has been added.

Agrobacterium Co-Cultivation.

Upon completion of the embryo isolation activity the tube of embryos is closed and placed on a rocker platform for 5 minutes. The contents of the tube are then poured out onto a plate of co-cultivation medium and the liquid *Agrobacterium* suspension is removed with a sterile, disposable, transfer pipette and the embryos are oriented with the scutellum facing up using a microscope. The plate is then closed, sealed with 3M Micropore tape, and placed in an incubator at 25° C. with 24 hours/day light at approximately 60 µmol $m^{-2}$ $s^{-1}$ photosynthetically active radiation (PAR).

Callus Selection and Regeneration of Transgenic Events.

Following the co-cultivation period, embryos are transferred to Resting medium. No more than 36 embryos are moved to each plate. The plates are incubated at 27° C. with 24 hours/day light at approximately 50 µmol $m^{-2}$ $s^{-1}$ PAR for 7-10 days. Callused embryos are then transferred onto Selection I medium. No more than 18 callused embryos are moved to each plate of Selection I. The plates are incubated at 27° C. with 24 hours/day light at approximately 50 µmol $m^{-2}$ $s^{-1}$ PAR for 7 days. Callused embryos are then transferred to Selection II medium. No more than 12 callused embryos are moved to each plate of Selection II. The plates are incubated at 27° C. with 24 hours/day light at approximately 50 µmol $m^{-2}$ $s^{-1}$ PAR for 14 days.

At this stage resistant calli are moved to Pre-Regeneration medium. No more than 9 calli are moved to each plate of Pre-Regeneration. The plates are held at 27° C. with 24 hours/day light at approximately 50 µmol $m^2$ $s^{-1}$ PAR for 7 days. Regenerating calli are then transferred to Regeneration medium in Phytatrays™ (Sigma-Aldrich). and incubated at 28° C. with 16 hours light/8 hours dark per day at approximately 150 µmol $m^{-2}$ $s^{-1}$ PAR for 7-14 days or until shoots develop. No more than 5 calli are placed in each Phytatray™. Small shoots with primary roots are then isolated and transferred to Shoot/Root medium. Rooted plantlets about 6 cm or taller are transplanted into soil and moved out to a growth chamber for hardening off.

Transformed plant shoots selected by their ability to grow on medium containing Haloxyfop are transplanted from Phytatrays™ to small pots filled with growing medium (ProMix BX; Premier Tech Horticulture), covered with cups or HUMI-DOMES (Arco Plastics), and then hardened-off in a Conviron growth chamber (27° C. day/24° C. night, 16-hour photoperiod, 50-70% RH, 200 µmol $m^{-2}s^{-1}$ PAR). In some instances, putative transgenic plantlets are analyzed for transgene relative copy number by quantitative real-time PCR assays using primers designed to detect the herbicide tolerance gene integrated into the maize genome. Further, RNA qPCR assays are used to detect the presence of the linker sequence in expressed dsRNAs of putative transformants. Selected transformed plantlets are then moved into a greenhouse for further growth and testing.

Transfer and Establishment of to Plants in the Greenhouse for Bioassay and Seed Production.

Plants are transplanted from Phytatrays™ to small pots (T.O. Plastics, 3.5" SVD, 700022C) filled with growing media (Premier Tech Horticulture, ProMix BX, 0581 P) and covered with Humidomes to acclimate the plants. They are placed in a Conviron growth chamber (28° C./24° C., 16-hour photoperiod, 50-70% RH, 200 µmol $m^2$ $s^{-1}$ PAR) until they reach the V3-V4 stage. This aids in acclimating the plants to soil and harsher temperatures. Plants are then moved to the greenhouse (Light Exposure Type: Photo or Assimilation; High Light Limit: 1200 µmol $m^{-2}$ $s^{-1}$ PAR; 16-hour day length; 27° C. day/24° C. night) and transplanted from the small pots to TINUS™ 350-4 Rootrainers® (Spencer-Lemaire Industries, Acheson, Alberta, Canada) prior to insect bioassay, at one plant per event per Rootrainer®. About 30 events are tested per construct. Approximately four days after transplanting to Rootrainers®, the V3-V4 stage plants are infested for bioassay, with about ready to hatch 150 western corn rootworm eggs (Crop Characteristics LLC, Farmington, Minn.) per plant. The bioassay is conducted for 2 weeks in the greenhouse and then, each event is graded following a modified method recommended by Oleson et al. (2005).

ROOT DAMAGE RATING (modified from Oleson et al, 2005)

0.00=No damage 0.01=Only a few minor feedings 0.02=Feeding scars evident—very light tunneling or channeling & no roots eaten off to within 4 cm of stalk (a root eaten to within 4 cm of the stalk is considered a "pruned root")

0.05=Severe scarring or when only the tips of several roots are injured on the entire root system 0.10=One root pruned 0.25=2-3 roots pruned or ¼ of roots pruned 0.50=4-5 roots pruned, considerable feeding damage on the outer portion of the root system; ½ of node pruned 0.75=6+ roots pruned, but with extensive feeding on outer portion of the root system; ¾ of node pruned 1.00=At least one full node of roots pruned, The inbred B104 and 7SH382 negative controls consistently provide 0.5 to 1.0 root ratings (high damage). $T_0$ events that provide 0.5 unit of root rating or less are saved and transplanted into 5 gallon pots for seed productions.

Plants of the $T_1$ generation are obtained by pollinating the silks of $T_0$ transgenic plants with pollen collected from plants of non-transgenic inbred line B104 or other appropriate pollen donors, and planting the resultant seeds. Reciprocal crosses are performed when possible. Selective $T_1$ events are tested for root protection against the western corn rootworm following the procedures used in $T_0$ event insect bioassay.

The foregoing provides methods for making and regenerating transgenic plants comprising insecticidal toxin polypeptides according to the invention.

Leaf Sampling for Western Blot Analyses.

The plants are sampled at the V-3 to V-5 stage. Two 6 mm diameter leaf samples are stored in a 96 well cluster tube rack at −80° C. until the day of analysis. Two Daisy™ steel BB's and 300 µl of extraction buffer (PBS solution containing 0.05% of Tween 20 and 5 ul/ml of Sigma protease inhibitors, catalog number 9599) is added to each tube. The samples are milled in a Kelco bead mill for 3 minutes, on maximum setting. Samples are centrifuged at 3,000×g for 5 minutes; 100 µl of the supernatant is transferred to an empty sample tube. Another 100 µl of extraction buffer is added to the plant sample and bead milled 3 additional minutes, centrifuged and 100 µl of this extract is combined with the first 100 µl. The combined supernatants are mixed and analyzed the same day as the extraction.

Western Blot (Qualitative Methods):

Conventional electrophoresis and blotting methods are used with Invitrogen™ devices and basic reagents. A Dow AgroSciences rabbit anti-IRDIG27642 antibody is the primary antibody for the detection of IRDIG27642 in leaf tissue. All proteins are detected with a CY-3 fluorescence detection system.

Example 11

Bioassay of Transgenic Maize

Bioactivity of the insecticidal toxins produced in plant cells is demonstrated by conventional bioassay methods (see, for example Huang et al., 2006). In one assay of efficacy, various plant tissues or tissue pieces derived from a plant producing an insecticidal toxin are fed to target insects in a controlled feeding environment. In another bioactivity assay, protein extracts are prepared from various plant tissues derived from the plant producing the insecticidal toxin and the extracted proteins are incorporated into artificial diet bioassays. The results of each feeding assay are compared to similarly conducted bioassays that employ appropriate control tissues from host plants that do not produce an insecticidal toxin, or to other control samples.

Example 12

Transgenic Glycine max Comprising an Insecticidal IRDIG Protein

Ten to 20 transgenic $T_0$ Glycine max plants harboring expression vectors for nucleic acids comprising an insecticidal IRDIG protein are generated by Agrobacterium-mediated transformation. Mature soybean (Glycine max) seeds are sterilized overnight with chlorine gas for sixteen hours. Following sterilization with chlorine gas, the seeds are placed in an open container in a Laminar™ flow hood to dispel the chlorine gas. Next, the sterilized seeds are imbibed with sterile $H_2O$ for sixteen hours in the dark using a black box at 24° C.

Preparation of split-seed soybeans. The split soybean seed comprising a portion of an embryonic axis protocol required preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation. The split soybean seeds comprising a partial portion of the embryonic axis are then immersed for about 30 minutes in a solution of Agrobacterium tumefaciens (e.g., strain EHA 101 or EHA 105) containing binary plasmid comprising an insecticidal IRDIG protein. The Agrobacterium tumefaciens solution is diluted to a final concentration of $\lambda$=0.6 $OD_{650}$ before immersing the cotyledons comprising the embryo axis.

Co-cultivation. Following inoculation, the split soybean seed is allowed to co-cultivate with the Agrobacterium tumefaciens strain for 5 days on co-cultivation medium (Wang, Kan. Agrobacterium Protocols. 2. 1. New Jersey: Humana Press, 2006. Print.) in a Petri dish covered with a piece of filter paper.

Shoot induction. After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (Liberty®).

Shoot elongation. After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2EDTA$, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a Conviron™ growth chamber at 24° C. with an 18 h photoperiod at a light intensity of 80-90 mol/m² sec.

Rooting. Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L $Na_2EDTA$, 20 g/L sucrose and 0.59 g/L MES, 50 mg/L asparagine, 100 mg/L L-pyroglutamic acid 7 g/L Noble agar, pH 5.6) in phyta trays.

Cultivation. Following culture in a Conviron™ growth chamber at 24° C., 18 h photoperiod, for 1-2 weeks, the shoots which have developed roots are transferred to a soil mix in a covered sundae cup and placed in a Conviron™ growth chamber (models CMP4030 and CMP3244, Controlled Environments Limited, Winnipeg, Manitoba, Canada) under long day conditions (16 hours light/8 hours dark) at a light intensity of 120-150 mol/$m^2$ sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

Development and morphological characteristics of transgenic lines are compared with nontransformed plants. Plant root, shoot, foliage and reproduction characteristics are compared. There are no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of IRDIG proteins when cultured in vitro and in soil in the glasshouse.

The foregoing provides methods for making and selecting transgenic dicot plants (soybeans) comprising insecticidal toxin polypeptides according to the invention.

Example 13

Transformation of Additional Crop Species

Cotton is transformed with insecticidal IRDIG proteins (with or without a chloroplast transit peptide) to provide control of insects by utilizing a method known to those of skill in the art, for example, substantially the same techniques previously described in EXAMPLE 14 of U.S. Pat. No. 7,838,733, or Example 12 of PCT International Patent Publication No. WO 2007/053482.

BIBLIOGRAPHY

Beltz, G. A., Jacobs, K. A., Eickbush, T. H., Cherbas, P. T., Kafatos, F. C. (1983). Isolation of multigene families and determination of homologies by filter hybridization methods. In Wu, R., Grossman, L., Moldave, K. (eds.) Methods of Enzymology, Vol. 100 Academic Press, New York pp. 266-285.

Crickmore, N., Zeigler, D. R., Feitelson, J., Schnepf, E., Van Rie, J., Lereclus, D., Baum, J., and Dean, D. H. (1998). Revision of the Nomenclature for the *Bacillus thuringiensis* Pesticidal Crystal Proteins. *Microbiology and Molecular Biology Reviews* 62: 807-813; http://www.ncbi.nlm.nih.gov/pubmed/9729610.

Gassmann, A. J., Petzold-Maxwell, J. L., Clifton, E. H., Dunbar, M. W., Hoffmann, A. M., Ingber, D. A., Keweshan, R. S. (2014). Field-evolved resistance by western corn rootworm to multiple *Bacillus thuringiensis* toxins in transgenic maize. Proceedings of the National Academy of Sciences of the United States of America 111, 5141-5146.

Gassmann, A. J., Petzold-Maxwell, J. L., Keweshan, R. S., Dunbar, M. W. (2011). Field-evolved resistance to Bt maize by western corn rootworm. PLoS One 6, e22629.

Huang, F., Rogers, L. B., Rhett, G. H. (2006). Comparative susceptibility of European corn borer, southwestern corn borer, and sugarcane borer (Lepidoptera: Crambidae) to Cry1Ab protein in a commercial *Bacillus thuringiensis* corn hybrid. J. Econ. Entomol. 99:194-202.

Meihls, L. N., Hiadon, M. L., Siegfried, B. P., Miller, N. J., Sappinaton, T. W., Ellersieck, M. R., Spencer, T. A., Hibbard, B. E. (2008). Increased survival of western corn rootworm on transgenic corn within three generations of on-plant greenhouse selection. Proc Natl Acad Sci USA. 105(49):19177-82.

Meihls, L. N., Hiadon, M. L., Ellersieck, M. R., Tabashnik, B. E., Hibbard, B. E. (2012). Greenhouse-selected resistance to Cry3Bb1-producing corn in three western corn rootworm populations. PLoSOne. 7(12):e51055.

Narva, K. E., Siegfried, B. D., Storer, N. P. (2013). Transgenic Approaches to Western Corn Rootworm Control. Advances in Biochemical Engineering/Biotechnology 136, 135-162.

Oleson, J. D., Park, Y. L., Nowatzki, T. M., Tollefson, J. J. (2005). Node-injury scale to evaluate root injury by corn rootworms (Coleoptera: Chrysomelidae). J. Econ. Entomol. 98: 1-8.

Sambrook, J., Fritsch, E. F., Maniatis, T. (1989) *Molecular Cloning: A Laboratory Manual* (2nd ed., Cold Spring Harbor Laboratory Press, Plainview, N.Y.)

Tijssen, P. (1993) Laboratory Techniques in Biochemistry and Molecular Biology Hybridization with Nucleic Acid Probes, Part I, Chapter 2. P. C. van der Vliet (ed.), (Elsevier, N.Y.)

Wang, Kan. *Agrobacterium Protocols.* 2. 1. New Jersey: Humana Press, 2006. Print Weigel, D., Glazebrook, J. (eds.) (2002) *Arabidopsis*: A Laboratory Manual. Cold Spring Harbor Press, Cold Spring Harbor, N.Y., 354 pages.

What is claimed is:

1. A nucleic acid construct comprising, a nucleic acid sequence encoding an insecticidal IRDIG protein comprising a sequence having at least 99% sequence identity with any one of SEQ ID NOs: 2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, and 122, and a heterologous regulatory element.

2. A nucleic acid construct comprising a nucleic acid sequence of claim 1 encoding an insecticidal IRDIG protein comprising any one of SEQ ID NOs: 2, 4, 6, 8, 10, 12, 14, 16, 18, 20, 22, 24, 26, 28, 30, 32, 34, 36, 38, 40, 42, 44, 46, 71, 73, 75, 82, 84, 86, 88, 90, 92, 94, 96, 98, 100, 102, 104, 106, 108, 110, 112, 114, 116, 118, 120, and 122.

3. A plant or plant part comprising the construct of claim 1.

4. The plant part of claim 3 wherein the plant part is a seed.

5. A plant or plant part comprising the construct of claim 2.

6. The plant part of claim 5 wherein the plant part is a seed.

7. A plant or plant part comprising an insecticidal IRDIG protein encoded by the construct of claim 1.

8. The plant part of claim 7 wherein the plant part is a seed.

9. A plant or plant part comprising an insecticidal IRDIG protein encoded by the construct of claim 2.

10. The plant or plant part of claim 7, wherein the insecticidal IRDIG protein has insecticidal activity against an insect selected from the group consisting of the order Coleoptera and Western Corn Rootworm.

11. The seed of claim 8 wherein the insecticidal IRDIG protein has insecticidal activity against an Coleoptera or Western Corn Rootworm insects.

12. A method for producing a coleopteran-tolerant plant comprising breeding a non-transgenic plant with a transgenic plant comprising the construct of claim 1, stably incorporated into the genome of the plant, and selecting one or more progeny plants by analyzing for at least a portion of the construct in the one or more selected progeny plants.

13. A method for producing a coleopteran-tolerant plant comprising breeding a non-transgenic plant with a transgenic plant comprising the construct of claim 2, stably incorporated into the genome of the plant, and selecting one or more progeny plants by analyzing for at least a portion of the construct in the selected one or more progeny plants.

* * * * *

SEQUENCE LISTING

```
<160> NUMBER OF SEQ ID NOS: 132

<210> SEQ ID NO 1
<211> LENGTH: 570
<212> TYPE: DNA
<213> ORGANISM: Bacillus thuringiensis

<400> SEQUENCE: 1
atgtatatga ataatacatt attggaatta ctttcaaaaa taaaaaaaga attctttggt     60
ttgaatcatc aaaaaagaac gttagatgaa tttattaatc tattagatat agatccatct    120
```

```
gatcgtgaat tattaaaacg ccatttgtat cttttggata atagtataga acatattatg    180
aattatatac attctcttaa ccaagaaatc ttagtattag atcccactat ttttgcagca    240
gtatctggaa cgattattat caataataaa aattatacat ttgtagaagt gcaatatagc    300
caaagtgatc aatatggacc aaaaagaggg attaaattta caggtggagg aaatgaatat    360
ttaattgatc ccaatccaca tgaaaatgga caatatcaaa aaacgccag acaattttat     420 agtgctttag catatggtat acaagggaag tctataacag atggacaaaa tgggcatcct    480
tgggtacaaa ataattggcc cacaggcaat caagatcgga ttaatgcact aggagaaaga    540
tatacattac aatacaaagg tagagcttaa                                     570

<210> SEQ ID NO 2
<211> LENGTH: 189
<212> TYPE: PRT
<213> ORGANISM: Bacillus thuringiensis

<400> SEQUENCE: 2

Met Tyr Met Asn Asn Thr Leu Leu Glu Leu Leu Ser Lys Ile Lys Lys
1               5                   10                  15

Glu Phe Phe Gly Leu Asn His Gln Lys Arg Thr Leu Asp Glu Phe Ile
            20                  25                  30

Asn Leu Leu Asp Ile Asp Pro Ser Asp Arg Glu Leu Leu Lys Arg His
        35                  40                  45

Leu Tyr Leu Leu Asp Asn Ser Ile Glu His Ile Met Asn Tyr Ile His
    50                  55                  60

Ser Leu Asn Gln Glu Ile Leu Val Leu Asp Pro Thr Ile Phe Ala Ala
65                  70                  75                  80

Val Ser Gly Thr Ile Ile Ile Asn Asn Lys Asn Tyr Thr Phe Val Glu
                85                  90                  95

Val Gln Tyr Ser Gln Ser Asp Gln Tyr Gly Pro Lys Arg Gly Ile Lys
            100                 105                 110

Phe Thr Gly Gly Gly Asn Glu Tyr Leu Ile Asp Pro Asn Pro His Glu
        115                 120                 125

Asn Gly Gln Tyr Gln Lys Asn Ala Arg Gln Phe Tyr Ser Ala Leu Ala
    130                 135                 140

Tyr Gly Ile Gln Gly Lys Ser Ile Thr Asp Gly Gln Asn Gly His Pro
145                 150                 155                 160

Trp Val Gln Asn Asn Trp Pro Thr Gly Asn Gln Asp Arg Ile Asn Ala
                165                 170                 175

Leu Gly Glu Arg Tyr Thr Leu Gln Tyr Lys Gly Arg Ala
            180                 185

<210> SEQ ID NO 3
<211> LENGTH: 564
<212> TYPE: DNA
<213> ORGANISM: Bacillus thuringiensis

<400> SEQUENCE: 3
atgaataaca cattattgga attactttca aaaataaaaa aagaattctt tggtttgaat     60
catcaaaaaa gaacgttaga tgaatttatt aatctattag atatagaccc atctgatcgt    120
gaattattaa aacgccattt gtatcttttt gataatagta tagaacatat tatgaattat    180
atacattctc ttaaccaaga aatcttagta ttagatccca ctattttgc agcagtatct    240 ggaacgatta ttatcaataa taaaaattat acctttgtag aagtacaata tagccaaagt    300
gatcaatatg gaccaaaaag agggattaaa tttacaggtg gaggaaatga atatttaatt    360
```

```
gatcccaatc cacatgaaaa tggacaatat caaaaaaacg ctagacaatt ttatagtgct    420
ttagcatatg gtatacaagg gaagtctata acagatggaa aaaatgggca tccttgggta    480
caaaataatt ggcccacagt caatcaagat cggattaatg cactaggaga aagatataca    540
ttacaataca aaggtagggc ttaa                                            564
```

<210> SEQ ID NO 4
<211> LENGTH: 187
<212> TYPE: PRT
<213> ORGANISM: Bacillus thuringiensis

<400> SEQUENCE: 4

```
Met Asn Asn Thr Leu Leu Glu Leu Leu Ser Lys Ile Lys Lys Glu Phe
1               5                   10                  15

Phe Gly Leu Asn His Gln Lys Arg Thr Leu Asp Glu Phe Ile Asn Leu
            20                  25                  30

Leu Asp Ile Asp Pro Ser Asp Arg Glu Leu Leu Lys Arg His Leu Tyr
        35                  40                  45

Leu Phe Asp Asn Ser Ile Glu His Ile Met Asn Tyr Ile His Ser Leu
    50                  55                  60

Asn Gln Glu Ile Leu Val Leu Asp Pro Thr Ile Phe Ala Ala Val Ser
65                  70                  75                  80

Gly Thr Ile Ile Ile Asn Asn Lys Asn Tyr Thr Phe Val Glu Val Gln
                85                  90                  95

Tyr Ser Gln Ser Asp Gln Tyr Gly Pro Lys Arg Gly Ile Lys Phe Thr
            100                 105                 110

Gly Gly Gly Asn Glu Tyr Leu Ile Asp Pro Asn Pro His Glu Asn Gly
        115                 120                 125

Gln Tyr Gln Lys Asn Ala Arg Gln Phe Tyr Ser Ala Leu Ala Tyr Gly
    130                 135                 140

Ile Gln Gly Lys Ser Ile Thr Asp Gly Gln Asn Gly His Pro Trp Val
145                 150                 155                 160

Gln Asn Asn Trp Pro Thr Val Asn Gln Asp Arg Ile Asn Ala Leu Gly
                165                 170                 175

Glu Arg Tyr Thr Leu Gln Tyr Lys Gly Arg Ala
            180                 185
```

<210> SEQ ID NO 5
<211> LENGTH: 564
<212> TYPE: DNA
<213> ORGANISM: Bacillus thuringiensis

<400> SEQUENCE: 5

```
atgaataata cattattgga attactttca aaaataaaaa agaattcttt tggtttgaat     60
catcaaaaaa gaacattaga tgaatttatt aatctattag atatagaccc atctgatcgt    120
gaattattaa aacgccattt gtatcttttt gataatagta tagaacatat tatgaattat    180
atacattctc ttaaccaaga aatcttagta ttagatccca ctattttgc agcagtatct    240 ggaacgatta ttatcaataa taaaaattat acatttgtag aagtgcaata tagccaaagt    300
gatcaatatg gaccaaaaag agggattaaa tttacaggtg gaggaaatga atatttaatt    360
gatcccaatc cacatgaaaa tggacaatat caaaaaaacg ccagacaatt ttatagtgct    420
ttagcatatg gtatacaagg gaagtctata acagatggac aaaatgggca tccttgggta    480
ccaaataatt ggcccacagg caatcaagat cggattaatg cactaggaga aagatataca    540
```
ttacaataca aaggtagagc ttaa                                              564

<210> SEQ ID NO 6
<211> LENGTH: 187
<212> TYPE: PRT
<213> ORGANISM: Bacillus thuringiensis

<400> SEQUENCE: 6

Met Asn Asn Thr Leu Leu Glu Leu Leu Ser Lys Ile Lys Lys Glu Phe
1               5                   10                  15

Phe Gly Leu Asn His Gln Lys Arg Thr Leu Asp Glu Phe Ile Asn Leu
            20                  25                  30

Leu Asp Ile Asp Pro Ser Asp Arg Glu Leu Leu Lys Arg His Leu Tyr
        35                  40                  45

Leu Phe Asp Asn Ser Ile Glu His Ile Met Asn Tyr Ile His Ser Leu
    50                  55                  60

Asn Gln Glu Ile Leu Val Leu Asp Pro Thr Ile Phe Ala Ala Val Ser
65                  70                  75                  80

Gly Thr Ile Ile Ile Asn Asn Lys Asn Tyr Thr Phe Val Glu Val Gln
                85                  90                  95

Tyr Ser Gln Ser Asp Gln Tyr Gly Pro Lys Arg Gly Ile Lys Phe Thr
            100                 105                 110

Gly Gly Gly Asn Glu Tyr Leu Ile Asp Pro Asn Pro His Glu Asn Gly
        115                 120                 125

Gln Tyr Gln Lys Asn Ala Arg Gln Phe Tyr Ser Ala Leu Ala Tyr Gly
    130                 135                 140

Ile Gln Gly Lys Ser Ile Thr Asp Gly Gln Asn Gly His Pro Trp Val
145                 150                 155                 160

Pro Asn Asn Trp Pro Thr Gly Asn Gln Asp Arg Ile Asn Ala Leu Gly
                165                 170                 175

Glu Arg Tyr Thr Leu Gln Tyr Lys Gly Arg Ala
            180                 185

<210> SEQ ID NO 7
<211> LENGTH: 564
<212> TYPE: DNA
<213> ORGANISM: Bacillus thuringiensis

<400> SEQUENCE: 7
atgaataata cattattgga attactttca aaaataaaaa agaattctt tggtttgaat     60 catcaaaaaa gaacgttaga tgaatttatt aatctattag atatagatcc atctgatcgt    120
gaattattaa aacgccattt gtatcttttt gataatagta tagagcatat tatgaattat    180
atacattctc ttaaccaaga aatcttagta ttagatccca ctattttgc agcagtatct    240 ggaacgatta ttatcaataa taaaaattat acatttgtag aagtgcaata tagccaaagt    300
gatcaatatg gaccaaaaag aggaattaaa tttacaggtg gaggaaatga atatttaatt    360
gatcccaatc cacatgaaaa tggacaatat caaaaaaacg ccagacaatt ttatagtgct    420
ttagcatatg gtatacaagg gaagtctata acagatggac aaaatgggca tccttgggta    480
caaaataatt ggcccacagg caatcaagat cggattaatg cactaggaga agatataca    540 ttacaataca aaggtagagc ttaa                                          564

<210> SEQ ID NO 8
<211> LENGTH: 187
<212> TYPE: PRT
<213> ORGANISM: Bacillus thuringiensis

<400> SEQUENCE: 8

Met Asn Asn Thr Leu Leu Glu Leu Leu Ser Lys Ile Lys Lys Glu Phe
1               5                   10                  15

Phe Gly Leu Asn His Gln Lys Arg Thr Leu Asp Glu Phe Ile Asn Leu
            20                  25                  30

Leu Asp Ile Asp Pro Ser Asp Arg Glu Leu Leu Lys Arg His Leu Tyr
        35                  40                  45

Leu Phe Asp Asn Ser Ile Glu His Ile Met Asn Tyr Ile His Ser Leu
50                  55                  60

Asn Gln Glu Ile Leu Val Leu Asp Pro Thr Ile Phe Ala Ala Val Ser
65                  70                  75                  80

Gly Thr Ile Ile Ile Asn Asn Lys Asn Tyr Thr Phe Val Glu Val Gln
                85                  90                  95

Tyr Ser Gln Ser Asp Gln Tyr Gly Pro Lys Arg Gly Ile Lys Phe Thr
            100                 105                 110

Gly Gly Gly Asn Glu Tyr Leu Ile Asp Pro Asn Pro His Glu Asn Gly
        115                 120                 125

Gln Tyr Gln Lys Asn Ala Arg Gln Phe Tyr Ser Ala Leu Ala Tyr Gly
    130                 135                 140

Ile Gln Gly Lys Ser Ile Thr Asp Gly Gln Asn Gly His Pro Trp Val
145                 150                 155                 160

Gln Asn Asn Trp Pro Thr Gly Asn Gln Asn Asp Arg Ile Asn Ala Leu Gly
                165                 170                 175

Glu Arg Tyr Thr Leu Gln Tyr Lys Gly Arg Ala
            180                 185

<210> SEQ ID NO 9
<211> LENGTH: 333
<212> TYPE: DNA
<213> ORGANISM: Bacillus thuringiensis

<400> SEQUENCE: 9
atggcaacag ttagcggaaa aataataata aatactatta atatacatt cgcagaagtt      60 caatatagtg gaaatgatga agtggtaga cctaaaagag ggattgagtt taaaccagga     120
ggaaatcgat atattatttc tcctaatcca catttaaata taaatataa tacttcaaat     180 ggtccaatac aattttataa tgctttagca ttaaatctta gttataaagg agatgatgaa     240
cagtgggtaa aagggaattg gccaaaaaca aatctaagtg gtcttaattc gcttggacaa     300
aaatatattt taaaatatga cagtagtaat taa                                 333

<210> SEQ ID NO 10
<211> LENGTH: 110
<212> TYPE: PRT
<213> ORGANISM: Bacillus thuringiensis

<400> SEQUENCE: 10

Met Ala Thr Val Ser Gly Lys Ile Ile Ile Asn Thr Ile Lys Tyr Thr
1               5                   10                  15

Phe Ala Glu Val Gln Tyr Ser Gly Asn Asp Glu Ser Gly Arg Pro Lys
            20                  25                  30

Arg Gly Ile Glu Phe Lys Pro Gly Gly Asn Arg Tyr Ile Ile Ser Pro
        35                  40                  45

Asn Pro His Leu Asn Asn Lys Tyr Asn Thr Ser Asn Gly Pro Ile Gln
50                  55                  60

```
Phe Tyr Asn Ala Leu Ala Leu Asn Leu Ser Tyr Lys Gly Asp Asp Glu
 65                  70                  75                  80

Gln Trp Val Lys Gly Asn Trp Pro Lys Thr Asn Leu Ser Gly Leu Asn
                 85                  90                  95

Ser Leu Gly Gln Lys Tyr Ile Leu Lys Tyr Asp Ser Ser Asn
            100                 105                 110

<210> SEQ ID NO 11
<211> LENGTH: 555
<212> TYPE: DNA
<213> ORGANISM: Bacillus thuringiensis

<400> SEQUENCE: 11
atggataatc attttttaga tttaatctca aaagttaaaa ctaatttatt tgttctaaaa      60
aaacaaaaaa atactctttc agaatttcta gatttattaa atgtagattt atcagatcaa     120
tctttaattc aaaaatatct ccatattttt gaaaacagtc tattcaatat agaaaatcat     180
gttgatattc ttaaaaatga actatcaaca ttagatccag ctattttgat agcagttagt     240
ggatctatcc caataaataa tgtaaaatat acatttgctg aagttcagta cagtggaaat     300
gatgacagtg aaaacctaa agaggaatc gaatttaaat caggaggaaa ccgatacgta      360
atatctccta atccacatttt aaataatcga tataacggtg gtggacaacg agatttttat    420
aatgctttag cattaaaagt tagcgatatc ggtgatgatg aacattggga aaaaaacaac     480
tggccaacaa agaatttaac gcgtcttagt gcacttggtc aaaaatatga tttacattat     540
gatggtagag cttaa                                                      555

<210> SEQ ID NO 12
<211> LENGTH: 184
<212> TYPE: PRT
<213> ORGANISM: Bacillus thuringiensis

<400> SEQUENCE: 12

Met Asp Asn His Phe Leu Asp Leu Ile Ser Lys Val Lys Thr Asn Leu
 1               5                  10                  15

Phe Val Leu Lys Lys Gln Lys Asn Thr Leu Ser Glu Phe Leu Asp Leu
                20                  25                  30

Leu Asn Val Asp Leu Ser Asp Gln Ser Leu Ile Gln Lys Tyr Leu His
            35                  40                  45

Ile Phe Glu Asn Ser Leu Phe Asn Ile Glu Asn His Val Asp Ile Leu
 50                  55                  60

Lys Asn Glu Leu Ser Thr Leu Asp Pro Ala Ile Leu Ile Ala Val Ser
 65                  70                  75                  80

Gly Ser Ile Pro Ile Asn Asn Val Lys Tyr Thr Phe Ala Glu Val Gln
                 85                  90                  95

Tyr Ser Gly Asn Asp Asp Ser Gly Lys Pro Lys Arg Gly Ile Glu Phe
            100                 105                 110

Lys Ser Gly Gly Asn Arg Tyr Val Ile Ser Pro Asn Pro His Leu Asn
        115                 120                 125

Asn Arg Tyr Asn Gly Gly Gln Arg Asp Phe Tyr Asn Ala Leu Ala
130                 135                 140

Leu Lys Val Ser Asp Ile Gly Asp Asp Glu His Trp Glu Lys Asn Asn
145                 150                 155                 160

Trp Pro Thr Lys Asn Leu Thr Arg Leu Ser Ala Leu Gly Gln Lys Tyr
                165                 170                 175

Asp Leu His Tyr Asp Gly Arg Ala
            180
```

<210> SEQ ID NO 13
<211> LENGTH: 555
<212> TYPE: DNA
<213> ORGANISM: Bacillus thuringiensis

<400> SEQUENCE: 13

```
atgaataacc agttattaga tttactgtca aaaactcaaa ctaatttatt tgttctaaaa      60
gaacagaaaa atactttttc tgaatttatc gatttattaa aattagattc atcagatcga     120
tctttactcc aaaatatat ccatattttt gaaaatagct tattcaatat tgaaaaccat     180
attgatactt taaaaaatga attgtccta ttggatccag ctattttgc aacagttagt     240
ggatctattc aaataaacaa ggttaaatat acatttgctg aagttcagta cagtggaaat     300
gatgaaagtg gaaaacctaa agaggaatt gaatttaaat ccggtggaaa tcgatatgta     360
atctctccta atccacattt aaataataga tataacaatg gtggacaacg agatttttat     420
aatgctttag cattaaaagt tagcgatata ggtgatgatg aaaaatggga aaaaaatgaa     480
tggccaacaa aaaatctaac acatcttagt gcgcttggtc aaaaatatga tttacattat     540
gatggcagag cttaa                                                      555
```

<210> SEQ ID NO 14
<211> LENGTH: 184
<212> TYPE: PRT
<213> ORGANISM: Bacillus thuringiensis

<400> SEQUENCE: 14

```
Met Asn Asn Gln Leu Leu Asp Leu Leu Ser Lys Thr Gln Thr Asn Leu
1               5                   10                  15

Phe Val Leu Lys Glu Gln Lys Asn Thr Phe Ser Glu Phe Ile Asp Leu
            20                  25                  30

Leu Lys Leu Asp Ser Ser Asp Arg Ser Leu Leu Gln Lys Tyr Ile His
        35                  40                  45

Ile Phe Glu Asn Ser Leu Phe Asn Ile Glu Asn His Ile Asp Thr Leu
    50                  55                  60

Lys Asn Glu Leu Ser Leu Leu Asp Pro Ala Ile Phe Ala Thr Val Ser
65                  70                  75                  80

Gly Ser Ile Gln Ile Asn Lys Val Lys Tyr Thr Phe Ala Glu Val Gln
                85                  90                  95

Tyr Ser Gly Asn Asp Glu Ser Gly Lys Pro Lys Arg Gly Ile Glu Phe
            100                 105                 110

Lys Ser Gly Gly Asn Arg Tyr Val Ile Ser Pro Asn Pro His Leu Asn
        115                 120                 125

Asn Arg Tyr Asn Asn Gly Gly Gln Arg Asp Phe Tyr Asn Ala Leu Ala
    130                 135                 140

Leu Lys Val Ser Asp Ile Gly Asp Asp Glu Lys Trp Glu Lys Asn Glu
145                 150                 155                 160

Trp Pro Thr Lys Asn Leu Thr His Leu Ser Ala Leu Gly Gln Lys Tyr
                165                 170                 175

Asp Leu His Tyr Asp Gly Arg Ala
            180
```

<210> SEQ ID NO 15
<211> LENGTH: 555
<212> TYPE: DNA
<213> ORGANISM: Bacillus thuringiensis

<400> SEQUENCE: 15

```
atgaataatc atttattaga tttactttca aaagtccaaa ctaatttatt cgtcctaaaa      60
gaacacaaaa atattctttc agaatttcta gatttattaa atatagattc atcagataaa     120
tctttaattc aaaatcattt tcaaattttt agaaatactt tgttgaatat agaaaatcat     180
atggattccc taaaaaatga aatatcagta ataaatccag ctgttttgc aacagttagt     240
ggatctatta aataaacaa aatcaactat acatttgctg aagttaagta tagtgaaaat     300
gatgcaagtg aaaaacctaa aagaggaatt gaatttaaac ctggcggaaa tcgatatgta     360
atatctccta atccacattt gaataatcaa tacaacaata gtggacaacg acaatttat     420
agtgctttag cattaaatat tagctacaga ggtgatgatg aacattggga aaaaataat     480
tggccaacaa aaactcaaga tcgtattact gcacttggcc aaaaatatac tttaacatat     540
gatggtaaag cttaa                                                      555
```

<210> SEQ ID NO 16
<211> LENGTH: 184
<212> TYPE: PRT
<213> ORGANISM: Bacillus thuringiensis

<400> SEQUENCE: 16

```
Met Asn Asn His Leu Leu Asp Leu Leu Ser Lys Val Gln Thr Asn Leu
1               5                   10                  15
Phe Val Leu Lys Glu His Lys Asn Ile Leu Ser Glu Phe Leu Asp Leu
            20                  25                  30
Leu Asn Ile Asp Ser Ser Asp Lys Ser Leu Ile Gln Asn His Phe Gln
        35                  40                  45
Ile Phe Arg Asn Thr Leu Leu Asn Ile Glu Asn His Met Asp Ser Leu
    50                  55                  60
Lys Asn Glu Ile Ser Val Ile Asn Pro Ala Val Phe Ala Thr Val Ser
65                  70                  75                  80
Gly Ser Ile Lys Ile Asn Lys Ile Asn Tyr Thr Phe Ala Glu Val Lys
                85                  90                  95
Tyr Ser Glu Asn Asp Ala Ser Gly Lys Pro Lys Arg Gly Ile Glu Phe
            100                 105                 110
Lys Pro Gly Gly Asn Arg Tyr Val Ile Ser Pro Asn Pro His Leu Asn
        115                 120                 125
Asn Gln Tyr Asn Asn Ser Gly Gln Arg Gln Phe Tyr Ser Ala Leu Ala
    130                 135                 140
Leu Asn Ile Ser Tyr Arg Gly Asp Asp Glu His Trp Glu Lys Asn Asn
145                 150                 155                 160
Trp Pro Thr Lys Thr Gln Asp Arg Ile Thr Ala Leu Gly Gln Lys Tyr
                165                 170                 175
Thr Leu Thr Tyr Asp Gly Lys Ala
            180
```

<210> SEQ ID NO 17
<211> LENGTH: 558
<212> TYPE: DNA
<213> ORGANISM: Bacillus thuringiensis

<400> SEQUENCE: 17

```
atggataatc atttattaga gttactttta aaagttcaaa acaatctatt tgttctaaaa      60
gaacaaaaaa atactctttc agaattccta gacttattaa atatagattc atccaacaaa     120
```

| | | |
|---|---|---|
| actttaatcg aaaaatactt ttatattttt gaaaacagtt tattaaatat agagaattat | 180 | |
| attgattctc tcaaaagtga aatattagta ttagatccaa ctattttagc aacagtaagt | 240 | |
| gggaatatta cagtaaataa gatcaaatat acatttgcag aaatccaata tagcggaaat | 300 | |
| gatgaaagtg gacgtcctaa aagaggaatt gaatttaaac aaggaggaaa tcgatacgta | 360 | |
| atatctccta atccacattt aaatactcga tataatacta gtggaggacc tcgagatttt | 420 | |
| tataatgctt tagcattaaa tcttagctat agaggtgacg atgaacattg ggaaaaaaat | 480 | |
| aattggccaa caaaaaatca agaccgtctt aatgcacttg gagaaagata tactttaaaa | 540 | |
| tatgatggta gagcttaa | 558 | |

<210> SEQ ID NO 18
<211> LENGTH: 185
<212> TYPE: PRT
<213> ORGANISM: Bacillus thuringiensis

<400> SEQUENCE: 18

Met Asp Asn His Leu Leu Glu Leu Leu Leu Lys Val Gln Asn Asn Leu
1               5                   10                  15

Phe Val Leu Lys Glu Gln Lys Asn Thr Leu Ser Glu Phe Leu Asp Leu
            20                  25                  30

Leu Asn Ile Asp Ser Ser Asn Lys Thr Leu Ile Glu Lys Tyr Phe Tyr
        35                  40                  45

Ile Phe Glu Asn Ser Leu Leu Asn Ile Glu Asn Tyr Ile Asp Ser Leu
    50                  55                  60

Lys Ser Glu Ile Leu Val Leu Asp Pro Thr Ile Leu Ala Thr Val Ser
65                  70                  75                  80

Gly Asn Ile Thr Val Asn Lys Ile Lys Tyr Thr Phe Ala Glu Ile Gln
                85                  90                  95

Tyr Ser Gly Asn Asp Glu Ser Gly Arg Pro Lys Arg Gly Ile Glu Phe
            100                 105                 110

Lys Gln Gly Gly Asn Arg Tyr Val Ile Ser Pro Asn Pro His Leu Asn
        115                 120                 125

Thr Arg Tyr Asn Thr Ser Gly Gly Pro Arg Asp Phe Tyr Asn Ala Leu
    130                 135                 140

Ala Leu Asn Leu Ser Tyr Arg Gly Asp Asp Glu His Trp Glu Lys Asn
145                 150                 155                 160

Asn Trp Pro Thr Lys Asn Gln Asp Arg Leu Asn Ala Leu Gly Glu Arg
                165                 170                 175

Tyr Thr Leu Lys Tyr Asp Gly Arg Ala
            180                 185

<210> SEQ ID NO 19
<211> LENGTH: 558
<212> TYPE: DNA
<213> ORGANISM: Bacillus thuringiensis

<400> SEQUENCE: 19

| | | |
|---|---|---|
| atggataatc atttattaga gttactttta aaagttcaaa acaatttatt tgttctaaaa | 60 | |
| gaacaaaaaa atactctttc agaattccta gacttattaa atatagattc atccaacaaa | 120 | |
| actttaatcg aaaaatactt ttatattttt gaaaacagtt tattaaatat agagaattat | 180 | |
| attgattctc tcaaaagtga aatattagta ttagatccaa ctattttagc aacagtaagt | 240 | |
| gggaatatta cagtaaataa gatcaaatat acatttgcag aaatccaata tagcggaaat | 300 | |
| gatgaaagtg gacgtcctaa aagaggaatt gaatttaaac aaggaggaaa tcgatacgta | 360 | |

```
atatctccta atccacattt aaatactcga tataatacta gtggaggacc tcgagatttt      420
tataatgctt tagcattaaa tcttagctat agaggtgacg atgaacattg ggaaaaaaat      480
aattggccaa caaaaaatca agaccgtctt aatgcacttg gagaaagata tactttaaaa      540
tatgatggta gagcttaa                                                   558
```

<210> SEQ ID NO 20
<211> LENGTH: 185
<212> TYPE: PRT
<213> ORGANISM: Bacillus thuringiensis

<400> SEQUENCE: 20

```
Met Asp Asn His Leu Leu Glu Leu Leu Leu Lys Val Gln Asn Asn Leu
1               5                   10                  15

Phe Val Leu Lys Glu Gln Lys Asn Thr Leu Ser Glu Phe Leu Asp Leu
            20                  25                  30

Leu Asn Ile Asp Ser Ser Asn Lys Thr Leu Ile Glu Lys Tyr Phe Tyr
        35                  40                  45

Ile Phe Glu Asn Ser Leu Leu Asn Ile Glu Asn Tyr Ile Asp Ser Leu
    50                  55                  60

Lys Ser Glu Ile Leu Val Leu Asp Pro Thr Ile Leu Ala Thr Val Ser
65                  70                  75                  80

Gly Asn Ile Thr Val Asn Lys Ile Lys Tyr Thr Phe Ala Glu Ile Gln
                85                  90                  95

Tyr Ser Gly Asn Asp Glu Ser Gly Arg Pro Lys Arg Gly Ile Glu Phe
            100                 105                 110

Lys Gln Gly Gly Asn Arg Tyr Val Ile Ser Pro Asn Pro His Leu Asn
        115                 120                 125

Thr Arg Tyr Asn Thr Ser Gly Gly Pro Arg Asp Phe Tyr Asn Ala Leu
    130                 135                 140

Ala Leu Asn Leu Ser Tyr Arg Gly Asp Asp Glu His Trp Glu Lys Asn
145                 150                 155                 160

Asn Trp Pro Thr Lys Asn Gln Asp Arg Leu Asn Ala Leu Gly Glu Arg
                165                 170                 175

Tyr Thr Leu Lys Tyr Asp Gly Arg Ala
            180                 185
```

<210> SEQ ID NO 21
<211> LENGTH: 576
<212> TYPE: DNA
<213> ORGANISM: Bacillus thuringiensis

<400> SEQUENCE: 21

```
atgcagagga gtaaaatata tatgaataac cagttattag atttactgtc aaaaactcaa       60
actaatttat ttgttctaaa agaacagaaa atactttttt ctgaatttat cgatttatta      120
aaattagatt catcagatcg atctttactc caaaaatata tccatatttt tgaaaatagc      180
ttattcaata ttgaaaacca tattgatact ttaaaaaatg aattgtcctt attggatcca      240 gctattttttg caacagttag tggatctatt caaataaaca aggttaaaata tacatttgct      300 gaagttcagt acagtggaaa tgatgaaagt ggaaaaccta aagaggaat tgaatttaaa       360 tccggtggaa atcgatatgt aatctctcct aatccacatt taaataatag atataacaat      420
ggtggacaac gagatttta taatgcttta gcattaaaag ttagcgatat aggtgatgat      480
gaaaaatggg aaaaaaatga atggccaaca aaaaatctaa cacatcttag tgcgcttggt      540
```
caaaaatatg atttacatta tgatggcaga gcttaa                                     576

<210> SEQ ID NO 22
<211> LENGTH: 191
<212> TYPE: PRT
<213> ORGANISM: Bacillus thuringiensis

<400> SEQUENCE: 22

Met Gln Arg Ser Lys Ile Tyr Met Asn Asn Gln Leu Leu Asp Leu Leu
1               5                   10                  15

Ser Lys Thr Gln Thr Asn Leu Phe Val Leu Lys Glu Gln Lys Asn Thr
            20                  25                  30

Phe Ser Glu Phe Ile Asp Leu Leu Lys Leu Asp Ser Ser Asp Arg Ser
        35                  40                  45

Leu Leu Gln Lys Tyr Ile His Ile Phe Glu Asn Ser Leu Phe Asn Ile
    50                  55                  60

Glu Asn His Ile Asp Thr Leu Lys Asn Glu Leu Ser Leu Leu Asp Pro
65                  70                  75                  80

Ala Ile Phe Ala Thr Val Ser Gly Ser Ile Gln Ile Asn Lys Val Lys
                85                  90                  95

Tyr Thr Phe Ala Glu Val Gln Tyr Ser Gly Asn Asp Glu Ser Gly Lys
            100                 105                 110

Pro Lys Arg Gly Ile Glu Phe Lys Ser Gly Gly Asn Arg Tyr Val Ile
        115                 120                 125

Ser Pro Asn Pro His Leu Asn Asn Arg Tyr Asn Asn Gly Gly Gln Arg
    130                 135                 140

Asp Phe Tyr Asn Ala Leu Ala Leu Lys Val Ser Asp Ile Gly Asp Asp
145                 150                 155                 160

Glu Lys Trp Glu Lys Asn Glu Trp Pro Thr Lys Asn Leu Thr His Leu
                165                 170                 175

Ser Ala Leu Gly Gln Lys Tyr Asp Leu His Tyr Asp Gly Arg Ala
            180                 185                 190

<210> SEQ ID NO 23
<211> LENGTH: 366
<212> TYPE: DNA
<213> ORGANISM: Bacillus thuringiensis

<400> SEQUENCE: 23
atgaagaaaa gattttctgc cgtatcgttg tctctgattt ttgctcttgc tgtcattgta    60
tttcctttct ccgcctcgaa tgtagaagct aagggtgtaa gcggcacgat caaaatcaat   120
aacgaaacct ataaatatat cgaagaatcg ttcggaaaaa accggggcat tacattcaat   180
ccaggtaatc acacgtatac aatatctcca aatccacaca taatcctaa atataataaa   240 aaacaagttc agttctatgc cgagattgca aatggcgtta agcccaggt ggaaagatcc    300 gggtggaaaa actcctttac cggcattcaa gcgttagggg aaacctatac attaagcccg   360
cgttaa                                                              366

<210> SEQ ID NO 24
<211> LENGTH: 121
<212> TYPE: PRT
<213> ORGANISM: Bacillus thuringiensis

<400> SEQUENCE: 24

Met Lys Lys Arg Phe Ser Ala Val Ser Leu Ser Leu Ile Phe Ala Leu
1               5                   10                  15

```
Ala Val Ile Val Phe Pro Phe Ser Ala Ser Asn Val Glu Ala Lys Gly
            20                  25                  30

Val Ser Gly Thr Ile Lys Ile Asn Asn Glu Thr Tyr Lys Tyr Ile Glu
        35                  40                  45

Glu Ser Phe Gly Lys Asn Arg Gly Ile Thr Phe Asn Pro Gly Asn His
50                  55                  60

Thr Tyr Thr Ile Ser Pro Asn Pro His Asn Asn Pro Lys Tyr Asn Lys
65                  70                  75                  80

Lys Gln Val Gln Phe Tyr Ala Glu Ile Ala Asn Gly Val Lys Ala Gln
                85                  90                  95

Val Glu Arg Ser Gly Trp Lys Asn Ser Phe Thr Gly Ile Gln Ala Leu
            100                 105                 110

Gly Glu Thr Tyr Thr Leu Ser Pro Arg
            115                 120

<210> SEQ ID NO 25
<211> LENGTH: 387
<212> TYPE: DNA
<213> ORGANISM: Bacillus thuringiensis

<400> SEQUENCE: 25
atgaaagaag gagtgtttaa attgaaaaaa ggatttcttg ccgtatcatt gtcactgttt      60
ttggccattg cttaatcgt gtttcctttc tccggcacta atgtagatgc taaaggggta     120
agtggctcaa tcacgatcaa caaagagacc tataaatata tcgaagaatc tttcggaaaa     180
aatcgaggga ttacattcaa tccaggccag catacttaca aataaccccc gaatcctcac     240
gacaatccca aatacaacaa aaaacaagag cagttttatg aggaaatcgc aaaaggcgtt     300
aaaactcttg tagaaaaatc aggctggaaa gatacgctca gcaacattac agctctgggt     360
gaaacctata cattagctcc acgctaa                                          387

<210> SEQ ID NO 26
<211> LENGTH: 128
<212> TYPE: PRT
<213> ORGANISM: Bacillus thuringiensis

<400> SEQUENCE: 26

Met Lys Glu Gly Val Phe Lys Leu Lys Lys Gly Phe Leu Ala Val Ser
1               5                   10                  15

Leu Ser Leu Phe Leu Ala Ile Ala Leu Ile Val Phe Pro Phe Ser Gly
            20                  25                  30

Thr Asn Val Asp Ala Lys Gly Val Ser Gly Ser Ile Thr Ile Asn Lys
        35                  40                  45

Glu Thr Tyr Lys Tyr Ile Glu Glu Ser Phe Gly Lys Asn Arg Gly Ile
50                  55                  60

Thr Phe Asn Pro Gly Gln His Thr Tyr Lys Ile Thr Pro Asn Pro His
65                  70                  75                  80

Asp Asn Pro Lys Tyr Asn Lys Lys Gln Glu Gln Phe Tyr Glu Glu Ile
                85                  90                  95

Ala Lys Gly Val Lys Thr Leu Val Glu Lys Ser Gly Trp Lys Asp Thr
            100                 105                 110

Leu Ser Asn Ile Thr Ala Leu Gly Glu Thr Tyr Thr Leu Ala Pro Arg
            115                 120                 125

<210> SEQ ID NO 27
<211> LENGTH: 537
<212> TYPE: DNA
```

<213> ORGANISM: Bacillus thuringiensis

<400> SEQUENCE: 27

| atggataata | atttattata | tttaatttca | aaaatccaaa | ccaatttatt | tgttttaaaa | 60 |
| aaacaaaaac | atttaactta | tgaattctta | gaattattag | atatcaattc | atcagaacga | 120 |
| tctttacttg | aaaattattt | ttatatttt | gaaaacagtt | tatttaatat | tgatgatgat | 180 |
| attaattctc | ttataaatga | aatattagaa | ttagatcctt | ctattttgc | agtagttagt | 240 |
| ggcaaagaaa | aaattaataa | tattaattat | agatatgaag | aaattagatt | tggcggaact | 300 |
| gatagaggac | tcaaatatac | agcagatggt | tattcacttt | caactgctgt | ttcatataaa | 360 |
| ataagtcctg | atccacataa | taatagtgat | tataataata | gtccaccaag | attttattct | 420 |
| gctatgtcag | atagaattga | agaataggt | acttctgcta | aatggactcc | aggaaattgg | 480 |
| ccaagaacca | taaatgttaa | ggtatctaaa | gaaaattata | ctttaactaa | acaataa | 537 |

<210> SEQ ID NO 28
<211> LENGTH: 178
<212> TYPE: PRT
<213> ORGANISM: Bacillus thuringiensis

<400> SEQUENCE: 28

Met Asp Asn Asn Leu Leu Tyr Leu Ile Ser Lys Ile Gln Thr Asn Leu
1               5                   10                  15

Phe Val Leu Lys Lys Gln Lys His Leu Thr Tyr Glu Phe Leu Glu Leu
            20                  25                  30

Leu Asp Ile Asn Ser Ser Glu Arg Ser Leu Leu Glu Asn Tyr Phe Tyr
        35                  40                  45

Ile Phe Glu Asn Ser Leu Phe Asn Ile Asp Asp Ile Asn Ser Leu
    50                  55                  60

Ile Asn Glu Ile Leu Glu Leu Asp Pro Ser Ile Phe Ala Val Val Ser
65                  70                  75                  80

Gly Lys Glu Lys Ile Asn Asn Ile Asn Tyr Arg Tyr Glu Glu Ile Arg
                85                  90                  95

Phe Gly Gly Thr Asp Arg Gly Leu Lys Tyr Thr Ala Asp Gly Tyr Ser
            100                 105                 110

Leu Ser Thr Ala Val Ser Tyr Lys Ile Ser Pro Asp Pro His Asn Asn
        115                 120                 125

Ser Asp Tyr Asn Asn Ser Pro Pro Arg Phe Tyr Ser Ala Met Ser Asp
    130                 135                 140

Arg Ile Glu Arg Ile Gly Thr Ser Ala Lys Trp Thr Pro Gly Asn Trp
145                 150                 155                 160

Pro Arg Thr Ile Asn Val Lys Val Ser Lys Glu Asn Tyr Thr Leu Thr
                165                 170                 175

Lys Gln

<210> SEQ ID NO 29
<211> LENGTH: 570
<212> TYPE: DNA
<213> ORGANISM: Bacillus thuringiensis

<400> SEQUENCE: 29

| atgtatatga | ataatacatt | attggaatta | ctttcaaaaa | taaaaaaaga | attctttggt | 60 |
| ttgaatcatc | aaaaaagaac | gttagatgaa | tttattaatc | tattagatat | agatccatct | 120 |
| gatcgtgaat | tattaaaacg | ccatttgtat | cttttttgata | atagtataga | acatattatg | 180 |

```
aattatatac attctcttaa ccaagaaatc ttagtattag atcccactat ttttgcagca    240
gtatctggaa cgattattat caataataaa aattatacat tgtagaagt gcaatatagc    300 caaagtgatc aatatggacc aaaaagaggg attaaattta caggtggagg aaatgaatat   360
ttaattgatc ccaatccaca tgaaaatgga caatatcaaa aaaacgccag acaatttat    420 agtgctttag catatggtat acaagggaag tctataacag atggacaaaa tgggcatcct   480
tgggtacaaa ataattggcc cacaggcaat caagatcgga ttaatgcact aggagaaaga   540
tatacattac aatacaaagg gagagcttaa                                    570
```

<210> SEQ ID NO 30
<211> LENGTH: 189
<212> TYPE: PRT
<213> ORGANISM: Bacillus thuringiensis

<400> SEQUENCE: 30

```
Met Tyr Met Asn Asn Thr Leu Leu Glu Leu Leu Ser Lys Ile Lys Lys
1               5                   10                  15

Glu Phe Phe Gly Leu Asn His Gln Lys Arg Thr Leu Asp Glu Phe Ile
                20                  25                  30

Asn Leu Leu Asp Ile Asp Pro Ser Asp Arg Glu Leu Leu Lys Arg His
            35                  40                  45

Leu Tyr Leu Phe Asp Asn Ser Ile Glu His Ile Met Asn Tyr Ile His
        50                  55                  60

Ser Leu Asn Gln Glu Ile Leu Val Leu Asp Pro Thr Ile Phe Ala Ala
65                  70                  75                  80

Val Ser Gly Thr Ile Ile Ile Asn Asn Lys Asn Tyr Thr Phe Val Glu
                85                  90                  95

Val Gln Tyr Ser Gln Ser Asp Gln Tyr Gly Pro Lys Arg Gly Ile Lys
                100                 105                 110

Phe Thr Gly Gly Gly Asn Glu Tyr Leu Ile Asp Pro Asn Pro His Glu
            115                 120                 125

Asn Gly Gln Tyr Gln Lys Asn Ala Arg Gln Phe Tyr Ser Ala Leu Ala
        130                 135                 140

Tyr Gly Ile Gln Gly Lys Ser Ile Thr Asp Gly Gln Asn Gly His Pro
145                 150                 155                 160

Trp Val Gln Asn Asn Trp Pro Thr Gly Asn Gln Asp Arg Ile Asn Ala
                165                 170                 175

Leu Gly Glu Arg Tyr Thr Leu Gln Tyr Lys Gly Arg Ala
            180                 185
```

<210> SEQ ID NO 31
<211> LENGTH: 639
<212> TYPE: DNA
<213> ORGANISM: Bacillus thuringiensis

<400> SEQUENCE: 31

```
atgcaatctt ttttttgtttt tccagcattg tttaagattc taaatcaact agcaccacag    60
gtaaggagta tgtatatgaa taatacatta ttgaaattac tttcaaaaat aaaaaaagaa   120
ttctttggtt tgaatcatca aaaaagaacg ttagatgaat ttattaatct attagatata   180
gatccatctg atcgtgaatt attaaaacgc catttgtatc ttttggataa tagtatagaa   240
catattatga attatataca ttctcttaac caagaaatct tagtattgga tcccactatt   300
tttgcagcag tatctggaac gattattatc aataataaaa attatacatt gtagaagtg    360 caatatagcc aaagtgatca atatggacca aaaagaggga ttaaatttac aggtggagga   420
```

```
aatgaatatt taattgatcc caatccacat gaaaatggac aatatcaaaa aaacgccaga    480
caattttata gtgctttagc atatggtata caagggaagt ctataacaga tggacaaaat    540
gggcatcctt gggtacaaaa taattggccc acaggcaatc aagatcggat taatgcacta    600
ggagaaagat atacattaca atacaaaggt agagcttaa                          639
```

<210> SEQ ID NO 32
<211> LENGTH: 212
<212> TYPE: PRT
<213> ORGANISM: Bacillus thuringiensis

<400> SEQUENCE: 32

```
Met Gln Ser Phe Phe Val Phe Pro Ala Leu Phe Lys Ile Leu Asn Gln
1               5                   10                  15

Leu Ala Pro Gln Val Arg Ser Met Tyr Met Asn Asn Thr Leu Leu Lys
            20                  25                  30

Leu Leu Ser Lys Ile Lys Lys Glu Phe Phe Gly Leu Asn His Gln Lys
        35                  40                  45

Arg Thr Leu Asp Glu Phe Ile Asn Leu Leu Asp Ile Asp Pro Ser Asp
    50                  55                  60

Arg Glu Leu Leu Lys Arg His Leu Tyr Leu Leu Asp Asn Ser Ile Glu
65                  70                  75                  80

His Ile Met Asn Tyr Ile His Ser Leu Asn Gln Glu Ile Leu Val Leu
                85                  90                  95

Asp Pro Thr Ile Phe Ala Ala Val Ser Gly Thr Ile Ile Ile Asn Asn
            100                 105                 110

Lys Asn Tyr Thr Phe Val Glu Val Gln Tyr Ser Gln Ser Asp Gln Tyr
        115                 120                 125

Gly Pro Lys Arg Gly Ile Lys Phe Thr Gly Gly Asn Glu Tyr Leu
    130                 135                 140

Ile Asp Pro Asn Pro His Glu Asn Gly Gln Tyr Gln Lys Asn Ala Arg
145                 150                 155                 160

Gln Phe Tyr Ser Ala Leu Ala Tyr Gly Ile Gln Gly Lys Ser Ile Thr
                165                 170                 175

Asp Gly Gln Asn Gly His Pro Trp Val Gln Asn Asn Trp Pro Thr Gly
            180                 185                 190

Asn Gln Asp Arg Ile Asn Ala Leu Gly Glu Arg Tyr Thr Leu Gln Tyr
        195                 200                 205

Lys Gly Arg Ala
    210
```

<210> SEQ ID NO 33
<211> LENGTH: 570
<212> TYPE: DNA
<213> ORGANISM: Bacillus thuringiensis

<400> SEQUENCE: 33

```
atgtatatga ataatacatt attgaaatta ctttcaaaaa taaaaaaaga attctttggt     60
ttgaatcatc aaaaaagaac gttagatgaa tttattaatc tattagatat agatccatct    120
gatcgtgaat tattaaaacg ccatttgtat cttttggata atagtataga acatattatg    180
aattatatac attctcttaa ccaagaaatc ttagtattgg atcccactat ttttgcagca    240
gtatctggaa cgattattat caataataaa aattatacat tgtagaagt gcaatatagc     300 caaagtgatc aatatggacc aaaaagaggg attaaattta caggtggagg aaatgaatat    360
```

```
ttaattgatc ccaatccaca tgaaaatgga caatatcaaa aaaacgccag acaatttat      420 agtgctttag catatggtat acaagggaag tctataacag atggacaaaa tgggcatcct     480
tgggtacaaa ataattggcc cacaggcaat caagatcgga ttaatgcact aggagaaaga    540
tatacattac aatacaaagg tagagcttaa                                     570
```

<210> SEQ ID NO 34
<211> LENGTH: 189
<212> TYPE: PRT
<213> ORGANISM: Bacillus thuringiensis

<400> SEQUENCE: 34

```
Met Tyr Met Asn Asn Thr Leu Leu Lys Leu Leu Ser Lys Ile Lys Lys
1               5                   10                  15

Glu Phe Phe Gly Leu Asn His Gln Lys Arg Thr Leu Asp Glu Phe Ile
            20                  25                  30

Asn Leu Leu Asp Ile Asp Pro Ser Asp Arg Glu Leu Leu Lys Arg His
        35                  40                  45

Leu Tyr Leu Leu Asp Asn Ser Ile Glu His Ile Met Asn Tyr Ile His
    50                  55                  60

Ser Leu Asn Gln Glu Ile Leu Val Leu Asp Pro Thr Ile Phe Ala Ala
65                  70                  75                  80

Val Ser Gly Thr Ile Ile Ile Asn Asn Lys Asn Tyr Thr Phe Val Glu
                85                  90                  95

Val Gln Tyr Ser Gln Ser Asp Gln Tyr Gly Pro Lys Arg Gly Ile Lys
            100                 105                 110

Phe Thr Gly Gly Gly Asn Glu Tyr Leu Ile Asp Pro Asn Pro His Glu
        115                 120                 125

Asn Gly Gln Tyr Gln Lys Asn Ala Arg Gln Phe Tyr Ser Ala Leu Ala
    130                 135                 140

Tyr Gly Ile Gln Gly Lys Ser Ile Thr Asp Gly Gln Asn Gly His Pro
145                 150                 155                 160

Trp Val Gln Asn Asn Trp Pro Thr Gly Asn Gln Asp Arg Ile Asn Ala
                165                 170                 175

Leu Gly Glu Arg Tyr Thr Leu Gln Tyr Lys Gly Arg Ala
            180                 185
```

<210> SEQ ID NO 35
<211> LENGTH: 564
<212> TYPE: DNA
<213> ORGANISM: Bacillus thuringiensis

<400> SEQUENCE: 35

```
atgaataata cattattgga attactttca aaaataaaaa aagaattctt tggtttgaat      60
catcaaaaaa gaacgttaga tgaatttatt aatctattag atatagatcc atctgatcgt    120
gaattattaa aacgccattt gtatcttttg gataatagta tagaacatat tatgaattat    180
atacattctc ttaaccaaga aatcttagta ttagatccca ctattttgc agcagtatct    240 ggaacgatta ttatcaataa taaaaattat acatttgtag aagtgcaata tagccaaagt    300
gatcaatatg gaccaaaaag agggattaaa tttacaggtg gaggaaatga atatttaatt    360
gatcccaatc cacatgaaaa tggacaatat caaaaaaacg ccagacaatt ttatagtgct    420
ttagcatatg gtatacaagg gaagtctata acagatggac aaaatgggca tccttgggta    480
caaaataatt ggcccacagg caatcaagat cggattaatg cactaggaga aagatataca    540
ttacaataca aggtagagc ttaa                                             564
```

<210> SEQ ID NO 36
<211> LENGTH: 187
<212> TYPE: PRT
<213> ORGANISM: Bacillus thuringiensis

<400> SEQUENCE: 36

Met Asn Asn Thr Leu Leu Glu Leu Leu Ser Lys Ile Lys Lys Glu Phe
1               5                   10                  15

Phe Gly Leu Asn His Gln Lys Arg Thr Leu Asp Glu Phe Ile Asn Leu
            20                  25                  30

Leu Asp Ile Asp Pro Ser Asp Arg Glu Leu Leu Lys Arg His Leu Tyr
        35                  40                  45

Leu Leu Asp Asn Ser Ile Glu His Ile Met Asn Tyr Ile His Ser Leu
    50                  55                  60

Asn Gln Glu Ile Leu Val Leu Asp Pro Thr Ile Phe Ala Ala Val Ser
65                  70                  75                  80

Gly Thr Ile Ile Ile Asn Asn Lys Asn Tyr Thr Phe Val Glu Val Gln
                85                  90                  95

Tyr Ser Gln Ser Asp Gln Tyr Gly Pro Lys Arg Gly Ile Lys Phe Thr
            100                 105                 110

Gly Gly Gly Asn Glu Tyr Leu Ile Asp Pro Asn Pro His Glu Asn Gly
        115                 120                 125

Gln Tyr Gln Lys Asn Ala Arg Gln Phe Tyr Ser Ala Leu Ala Tyr Gly
    130                 135                 140

Ile Gln Gly Lys Ser Ile Thr Asp Gly Gln Asn Gly His Pro Trp Val
145                 150                 155                 160

Gln Asn Asn Trp Pro Thr Gly Asn Gln Asp Arg Ile Asn Ala Leu Gly
                165                 170                 175

Glu Arg Tyr Thr Leu Gln Tyr Lys Gly Arg Ala
            180                 185

<210> SEQ ID NO 37
<211> LENGTH: 366
<212> TYPE: DNA
<213> ORGANISM: Bacillus thuringiensis

<400> SEQUENCE: 37
atgaaaaaag gatttcttgc cgtatcattg tctttgtttt tggcccttgc tttaatcgtg    60
cttcctttct ccggcgctaa tgtagaagct aaaggggtaa gtggctcaat cacgatcaag   120
aaagaaacat ataatatat cgaagaatct ttcggaaaaa accgagggat tacattcaat   180
ccaggccaac atacgtacaa aataactccg aatcctcacg acaatcccaa gtataacaaa   240
aaacaagagc agttttatga ggaaatcgca aaagccgtta aagtcttgt agaaaaatca   300 ggctggaaag acaccttcag caacattaca gctctgggtg aaacctatac attagctcca   360
cgctaa                                                              366

<210> SEQ ID NO 38
<211> LENGTH: 121
<212> TYPE: PRT
<213> ORGANISM: Bacillus thuringiensis

<400> SEQUENCE: 38

Met Lys Lys Gly Phe Leu Ala Val Ser Leu Ser Leu Phe Leu Ala Leu
1               5                   10                  15

Ala Leu Ile Val Leu Pro Phe Ser Gly Ala Asn Val Glu Ala Lys Gly

-continued

```
                 20                  25                  30
Val Ser Gly Ser Ile Thr Ile Lys Lys Glu Thr Tyr Lys Tyr Ile Glu
             35                  40                  45

Glu Ser Phe Gly Lys Asn Arg Gly Ile Thr Phe Asn Pro Gly Gln His
         50                  55                  60

Thr Tyr Lys Ile Thr Pro Asn Pro His Asp Asn Pro Lys Tyr Asn Lys
 65                  70                  75                  80

Lys Gln Glu Gln Phe Tyr Glu Glu Ile Ala Lys Ala Val Lys Ser Leu
                 85                  90                  95

Val Glu Lys Ser Gly Trp Lys Asp Thr Phe Ser Asn Ile Thr Ala Leu
             100                 105                 110

Gly Glu Thr Tyr Thr Leu Ala Pro Arg
             115                 120
```

<210> SEQ ID NO 39
<211> LENGTH: 492
<212> TYPE: DNA
<213> ORGANISM: Bacillus thuringiensis

<400> SEQUENCE: 39

| | | |
|---|---|---|
| atggggcagc accaacacgt cattcgcaca acaaaaaaaa gtaaatttaa ggtattaatc | 60 |
| gcgcaaaatg gaatatataa aataaggagg tggccacctc tcagtttgaa agaaggagtg | 120 |
| tttaaattga aaaaggatt tcttgccgta tcattgtccc tgttttggc cattgcttta | 180 |
| atcgtgcttc ctttctccgg cactaatgta gatgctaaag gggtaagtgg ctcaatcacg | 240 |
| atcaacaaag aaacctataa atatatcgaa gaatctttcg gaaaaaatcg agggattaca | 300 |
| ttcaatccag gccagcatac gtacaaaata accccgaatc ctcacgacaa tcccaaatac | 360 |
| aacaaaaaac aagagcagtt ttatgaggaa atcgcaaaag gcgttaaaac tcttgtagaa | 420 |
| aaatcaggct ggaaagatac gctcagcaac attacagctc tgggtgaaac ctatacatta | 480 |
| gctccacgct aa | 492 |

<210> SEQ ID NO 40
<211> LENGTH: 163
<212> TYPE: PRT
<213> ORGANISM: Bacillus thuringiensis

<400> SEQUENCE: 40

```
Met Gly Gln His Gln His Val Ile Arg Thr Thr Lys Lys Ser Lys Phe
 1               5                  10                  15

Lys Val Leu Ile Ala Gln Asn Gly Ile Tyr Lys Ile Arg Arg Trp Pro
             20                  25                  30

Pro Leu Ser Leu Lys Glu Gly Val Phe Lys Leu Lys Lys Gly Phe Leu
             35                  40                  45

Ala Val Ser Leu Ser Leu Phe Leu Ala Ile Ala Leu Ile Val Leu Pro
         50                  55                  60

Phe Ser Gly Thr Asn Val Asp Ala Lys Gly Val Ser Gly Ser Ile Thr
 65                  70                  75                  80

Ile Asn Lys Glu Thr Tyr Lys Tyr Ile Glu Glu Ser Phe Gly Lys Asn
                 85                  90                  95

Arg Gly Ile Thr Phe Asn Pro Gly Gln His Thr Tyr Lys Ile Thr Pro
             100                 105                 110

Asn Pro His Asp Asn Pro Lys Tyr Asn Lys Lys Gln Glu Gln Phe Tyr
             115                 120                 125

Glu Glu Ile Ala Lys Gly Val Lys Thr Leu Val Glu Lys Ser Gly Trp
```

```
                130               135               140
Lys Asp Thr Leu Ser Asn Ile Thr Ala Leu Gly Glu Thr Tyr Thr Leu
145                 150               155               160

Ala Pro Arg

<210> SEQ ID NO 41
<211> LENGTH: 285
<212> TYPE: DNA
<213> ORGANISM: Bacillus thuringiensis

<400> SEQUENCE: 41
atggtgcaat atagccaaag tgatcaatat ggaccaaaaa gagggattaa atttacaggt      60
ggaggaaatg aatatttaat tgatcccaat ccacatgaaa atggacaata tcaaaaaaac    120
gccagacaat tttatagtgc tttagcatat ggtatacaag gaagtctat aacagatgga     180 caaaatgggc atccttgggt acaaaataat tggcctacag gcaatcaaga tcggattaat    240
gcactaggag aaagatatac attacaatac aaaggtagag cttaa                    285

<210> SEQ ID NO 42
<211> LENGTH: 94
<212> TYPE: PRT
<213> ORGANISM: Bacillus thuringiensis

<400> SEQUENCE: 42

Met Val Gln Tyr Ser Gln Ser Asp Gln Tyr Gly Pro Lys Arg Gly Ile
1               5                   10                  15

Lys Phe Thr Gly Gly Gly Asn Glu Tyr Leu Ile Asp Pro Asn Pro His
            20                  25                  30

Glu Asn Gly Gln Tyr Gln Lys Asn Ala Arg Gln Phe Tyr Ser Ala Leu
        35                  40                  45

Ala Tyr Gly Ile Gln Gly Lys Ser Ile Thr Asp Gly Gln Asn Gly His
    50                  55                  60

Pro Trp Val Gln Asn Asn Trp Pro Thr Gly Asn Gln Asp Arg Ile Asn
65                  70                  75                  80

Ala Leu Gly Glu Arg Tyr Thr Leu Gln Tyr Lys Gly Arg Ala
                85                  90

<210> SEQ ID NO 43
<211> LENGTH: 285
<212> TYPE: DNA
<213> ORGANISM: Bacillus thuringiensis

<400> SEQUENCE: 43
atggtgcaat atagccaaag tgatccatat ggactgaaaa gagggattaa atttacaggt      60
ggaggaaatg aatatgtaat tgcgcctaat ccagatgaaa atggaaaata caaaaaaaat    120
acgagacaat tttataatga tttagcatat ggtatacaag gaagtctat aacagatgga     180 caaaatgggc atccttgggt acaaaataat tggcccacag gcaatcaaga tcggattaat    240
gcactaggag aaagatatac attacaatac aaaggtagag cttaa                    285

<210> SEQ ID NO 44
<211> LENGTH: 94
<212> TYPE: PRT
<213> ORGANISM: Bacillus thuringiensis

<400> SEQUENCE: 44

Met Val Gln Tyr Ser Gln Ser Asp Pro Tyr Gly Leu Lys Arg Gly Ile
1               5                   10                  15
```

Lys Phe Thr Gly Gly Gly Asn Glu Tyr Val Ile Ala Pro Asn Pro Asp
                20                  25                  30

Glu Asn Gly Lys Tyr Lys Lys Asn Thr Arg Gln Phe Tyr Asn Asp Leu
             35                  40                  45

Ala Tyr Gly Ile Gln Gly Lys Ser Ile Thr Asp Gly Gln Asn Gly His
 50                  55                  60

Pro Trp Val Gln Asn Asn Trp Pro Thr Gly Asn Gln Asp Arg Ile Asn
 65                  70                  75                  80

Ala Leu Gly Glu Arg Tyr Thr Leu Gln Tyr Lys Gly Arg Ala
                 85                  90

<210> SEQ ID NO 45
<211> LENGTH: 561
<212> TYPE: DNA
<213> ORGANISM: Bacillus thuringiensis

<400> SEQUENCE: 45
atgaataatc cattgttaaa attactttca aacatacaaa aagaattatt tggcttgaat      60
catcaaagaa aaacattaga tacatttatt aatttattag atatagatgt atccgatcgt     120
gctttattaa aaagatattt tagtcttttt gataatagtt tagaacatat taccactcat     180
attgattctc ttaaaaaaga aatattagta ttagatcctg atattttttgc tgcagtatct     240 ggaacaatta ttataaataa tgcaatttat gcatttacag aagtgcatta tagtcaaagt     300
gatgaatatg ggcctaaaag aggtattaaa tttacaagag gaaatgaata tttaattgat     360
ccaaatccac atgaaaatgg tcaatatcaa aaaagtgcaa gccaattttta tagcgcttta     420 gcatatggtg tacaaggtaa atcaataaca gatggacaag acggacatcc ttggaaaaaa     480
aatgattggc ccacaaaaaa cctagatcgc attaatgtgc tcggagaaag atatacttta     540
ctctatcaac atagagatta a                                                561

<210> SEQ ID NO 46
<211> LENGTH: 186
<212> TYPE: PRT
<213> ORGANISM: Bacillus thuringiensis

<400> SEQUENCE: 46

Met Asn Asn Pro Leu Leu Lys Leu Leu Ser Asn Ile Gln Lys Glu Leu
1               5                   10                  15

Phe Gly Leu Asn His Gln Arg Lys Thr Leu Asp Thr Phe Ile Asn Leu
                20                  25                  30

Leu Asp Ile Asp Val Ser Asp Arg Ala Leu Leu Lys Arg Tyr Phe Ser
             35                  40                  45

Leu Phe Asp Asn Ser Leu Glu His Ile Thr Thr His Ile Asp Ser Leu
 50                  55                  60

Lys Lys Glu Ile Leu Val Leu Asp Pro Asp Ile Phe Ala Ala Val Ser
 65                  70                  75                  80

Gly Thr Ile Ile Ile Asn Asn Ala Ile Tyr Ala Phe Thr Glu Val His
                 85                  90                  95

Tyr Ser Gln Ser Asp Glu Tyr Gly Pro Lys Arg Gly Ile Lys Phe Thr
                100                 105                 110

Arg Gly Asn Glu Tyr Leu Ile Asp Pro Asn Pro His Glu Asn Gly Gln
            115                 120                 125

Tyr Gln Lys Ser Ala Ser Gln Phe Tyr Ser Ala Leu Ala Tyr Gly Val
        130                 135                 140

Gln Gly Lys Ser Ile Thr Asp Gly Gln Asp Gly His Pro Trp Lys Lys
145                 150                 155                 160

Asn Asp Trp Pro Thr Lys Asn Leu Asp Arg Ile Asn Val Leu Gly Glu
                165                 170                 175

Arg Tyr Thr Leu Leu Tyr Gln His Arg Asp
            180                 185

<210> SEQ ID NO 47
<211> LENGTH: 44
<212> TYPE: DNA
<213> ORGANISM: Artificial Sequence
<220> FEATURE:
<223> OTHER INFORMATION: synthesized primer oligonucleotide

<400> SEQUENCE: 47
gtgtactagt atggataatc atttttttaga tttaatctca aaag                44

<210> SEQ ID NO 48
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 48
tctcctcgag ttaagctcta ccatcataat gtaaatcata ttttgac            48

<210> SEQ ID NO 49
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 49
gtgtactagt atgaataacc agttattaga tttactgtca aaaactc              47

<210> SEQ ID NO 50
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 50
tctcctcgag ttaagctctg ccatcataat gtaaatcata ttttgac            48

<210> SEQ ID NO 51
<211> LENGTH: 45
<212> TYPE: DNA
<213> ORGANISM: Artificial Sequence
<220> FEATURE:
<223> OTHER INFORMATION: synthesized primer oligonucleotide

<400> SEQUENCE: 51
gtgtactagt atggcaacag ttagcggaaa ataataata aatac                45

<210> SEQ ID NO 52
<211> LENGTH: 53
<212> TYPE: DNA
<213> ORGANISM: Artificial Sequence
<220> FEATURE:
<223> OTHER INFORMATION: synthesized primer oligonucleotide

<400> SEQUENCE: 52

```
tctcctcgag ttaattacta ctgtcatatt ttaaaatata tttttgtcca agc        53
```

<210> SEQ ID NO 53
<211> LENGTH: 63
<212> TYPE: DNA
<213> ORGANISM: Artificial Sequence
<220> FEATURE:
<223> OTHER INFORMATION: synthesized primer oligonucleotide

<400> SEQUENCE: 53

```
gtgtactagt atgaataata cattattgga attactttca aaaataaaaa aagaattctt    60
tgg                                                                  63
```

<210> SEQ ID NO 54
<211> LENGTH: 48
<212> TYPE: DNA
<213> ORGANISM: Artificial Sequence
<220> FEATURE:
<223> OTHER INFORMATION: synthesized primer oligonucleotide

<400> SEQUENCE: 54

```
tctcctcgag ttaagctcta cctttgtatt gtaatgtata tctttctc             48
```

<210> SEQ ID NO 55
<211> LENGTH: 63
<212> TYPE: DNA
<213> ORGANISM: Artificial Sequence
<220> FEATURE:
<223> OTHER INFORMATION: synthesized primer oligonucleotide

<400> SEQUENCE: 55

```
gtgtactagt atgaataata cattattgga attactttca aaaataaaaa aagaattctt    60
tgg                                                                  63
```

<210> SEQ ID NO 56
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 56

```
tctcctcgag ttaagctcta cctttgtatt gtaatgtata tctttctcc            49
```

<210> SEQ ID NO 57
<211> LENGTH: 63
<212> TYPE: DNA
<213> ORGANISM: Artificial Sequence
<220> FEATURE:
<223> OTHER INFORMATION: synthesized primer oligonucleotide

<400> SEQUENCE: 57

```
gtgtactagt atgaataaca cattattgga attactttca aaaataaaaa aagaattctt    60
tgg                                                                  63
```

<210> SEQ ID NO 58
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 58

```
tctcctcgag ttaagcccta cctttgtatt gtaatgtata tctttctcc            49
```

<210> SEQ ID NO 59
<211> LENGTH: 69
<212> TYPE: DNA
<213> ORGANISM: Artificial Sequence
<220> FEATURE:
<223> OTHER INFORMATION: synthesized primer oligonucleotide

<400> SEQUENCE: 59
gtgtactagt atgtatatga ataatacatt attggaatta ctttcaaaaa taaaaaaga    60 attctttgg                                                           69

<210> SEQ ID NO 60
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 60
tctcctcgag ttaagctcta cctttgtatt gtaatgtata tctttctcc               49

<210> SEQ ID NO 61
<211> LENGTH: 37
<212> TYPE: DNA
<213> ORGANISM: Artificial Sequence
<220> FEATURE:
<223> OTHER INFORMATION: synthesized primer oligonucleotide

<400> SEQUENCE: 61
gtgtactagt atgaagaaaa gattttctgc cgtatcg                            37

<210> SEQ ID NO 62
<211> LENGTH: 36
<212> TYPE: DNA
<213> ORGANISM: Artificial Sequence
<220> FEATURE:
<223> OTHER INFORMATION: synthesized primer oligonucleotide

<400> SEQUENCE: 62
tctcctcgag ttaacgcggg cttaatgtat aggttt                             36

<210> SEQ ID NO 63
<211> LENGTH: 52
<212> TYPE: DNA
<213> ORGANISM: Artificial Sequence
<220> FEATURE:
<223> OTHER INFORMATION: synthesized primer oligonucleotide

<400> SEQUENCE: 63
gtgtactagt atggataata atttattata tttaatttca aaaatccaaa cc           52

<210> SEQ ID NO 64
<211> LENGTH: 52
<212> TYPE: DNA
<213> ORGANISM: Artificial Sequence
<220> FEATURE:
<223> OTHER INFORMATION: synthesized primer oligonucleotide

<400> SEQUENCE: 64
tctcctcgag ttattgttta gttaaagtat aattttcttt agatacctta ac           52

<210> SEQ ID NO 65
<211> LENGTH: 42
<212> TYPE: DNA

```
<213> ORGANISM: Artificial Sequence
<220> FEATURE:
<223> OTHER INFORMATION: synthesized primer oligonucleotide

<400> SEQUENCE: 65
gtgttctaga atgaaagaag gagtgtttaa attgaaaaaa gg                         42

<210> SEQ ID NO 66
<211> LENGTH: 39
<212> TYPE: DNA
<213> ORGANISM: Artificial Sequence
<220> FEATURE:
<223> OTHER INFORMATION: synthesized primer oligonucleotide

<400> SEQUENCE: 66
tctcctcgag ttagcgtgga gctaatgtat aggtttcac                             39

<210> SEQ ID NO 67
<211> LENGTH: 52
<212> TYPE: DNA
<213> ORGANISM: Artificial Sequence
<220> FEATURE:
<223> OTHER INFORMATION: synthesized primer oligonucleotide

<400> SEQUENCE: 67
gtgttctaga atggataatc atttattaga gttactttta aaagttcaaa ac              52

<210> SEQ ID NO 68
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 68
gtcactgcag ttaagctcta ccatcatatt ttaaagtata tctttctcc                  49

<210> SEQ ID NO 69
<211> LENGTH: 555
<212> TYPE: DNA
<213> ORGANISM: Artificial Sequence
<220> FEATURE:
<223> OTHER INFORMATION: Maize optimized

<400> SEQUENCE: 69
atgaataatc acctgcttga cctgctgtcc aaggtgcaga ccaacctgtt cgtgctgaag      60
gagcacaaaa atatcctgag cgagttcctg gacctattaa atatcgactc ctccgacaag     120
agcctgatcc agaaccactt tcagatattc cggaacaccc tgctgaacat cgagaaccac     180
atggactccc tgaagaatga aatttccgta ataaacccag cggtgttcgc gaccgtgagc     240
ggcagcatta aaataaacaa aatcaactat acattcgccg aggtgaagta cagcgagaac     300
gacgcctccg gcaagcctaa gaggggcatc gagttcaaac cgggtggcaa cagatacgtg     360
atcagcccga acccgcacct gaataatcaa tacaacaact ccggacagag gcagttctac     420
tccgcactgg cattaaacat ctcatacaga ggcgacgacg agcactggga gaaaaataat     480
tggccgacca agacccaaga taggatcacc gcgctgggcc aaaaatatac cctgacctac     540
gacggcaagg cctga                                                     555

<210> SEQ ID NO 70
<211> LENGTH: 555
<212> TYPE: DNA
<213> ORGANISM: Artificial Sequence
```

<220> FEATURE:
<223> OTHER INFORMATION: Maize optimized

<400> SEQUENCE: 70

```
atgaacaacc acctgcttga cctgctgtcc aaggtgcaga ccaacctgtt cgtgctgaag      60
gagcacaaga acatcctgag cgagttcctg gacctgctga atatcgactc ctccgacaag     120
agcctgatcc agaaccactt tcagatattc cggaacaccc tgctgaacat cgagaaccac     180
atggactccc tgaagaacga gatttccgtg atcaacccag cggtgttcgc gaccgtgagc     240
ggcagcatca agatcaacaa gatcaactac accttcgccg aggtgaagta cagcgagaac     300
gacgcctccg gcaagcctaa gaggggcatc gagttcaaac cgggtggcaa cagatacgtg     360
atcagcccga acccgcacct gaacaaccag tacaacaact ccggacagag gcagttctac     420
tccgcactgg cgctgaacat ctcatacaga ggcgacgacg agcactggga agaacaac      480
tggccgacca agacccaaga taggatcacc gcgctgggcc agaagtacac cctgacctac     540
gacggcaagg cctga                                                     555
```

<210> SEQ ID NO 71
<211> LENGTH: 184
<212> TYPE: PRT
<213> ORGANISM: Artificial Sequence
<220> FEATURE:
<223> OTHER INFORMATION: translated from synthesized maize optimized coding region

<400> SEQUENCE: 71

```
Met Asn Asn His Leu Leu Asp Leu Leu Ser Lys Val Gln Thr Asn Leu
1               5                   10                  15

Phe Val Leu Lys Glu His Lys Asn Ile Leu Ser Glu Phe Leu Asp Leu
            20                  25                  30

Leu Asn Ile Asp Ser Ser Asp Lys Ser Leu Ile Gln Asn His Phe Gln
        35                  40                  45

Ile Phe Arg Asn Thr Leu Leu Asn Ile Glu Asn His Met Asp Ser Leu
    50                  55                  60

Lys Asn Glu Ile Ser Val Ile Asn Pro Ala Val Phe Ala Thr Val Ser
65                  70                  75                  80

Gly Ser Ile Lys Ile Asn Lys Ile Asn Tyr Thr Phe Ala Glu Val Lys
                85                  90                  95

Tyr Ser Glu Asn Asp Ala Ser Gly Lys Pro Lys Arg Gly Ile Glu Phe
            100                 105                 110

Lys Pro Gly Gly Asn Arg Tyr Val Ile Ser Pro Asn Pro His Leu Asn
        115                 120                 125

Asn Gln Tyr Asn Asn Ser Gly Gln Arg Gln Phe Tyr Ser Ala Leu Ala
    130                 135                 140

Leu Asn Ile Ser Tyr Arg Gly Asp Asp Glu His Trp Glu Lys Asn Asn
145                 150                 155                 160

Trp Pro Thr Lys Thr Gln Asp Arg Ile Thr Ala Leu Gly Gln Lys Tyr
                165                 170                 175

Thr Leu Thr Tyr Asp Gly Lys Ala
            180
```

<210> SEQ ID NO 72
<211> LENGTH: 753
<212> TYPE: DNA
<213> ORGANISM: Artificial Sequence
<220> FEATURE:
<223> OTHER INFORMATION: Maize optimized

<400> SEQUENCE: 72

```
atggctcaat ctagcagaat ctgccacggt gtgcagaacc catgtgtgat catttccaat      60
ctctccaaat ccaaccagaa caaatctcct ttctcagtca gcctcaagac tcaccagcag     120
cagcgtcgtg cttaccagat atctagctgg ggattgaaga agtcaaacaa cgggtccgtg     180
attcgtccgg ttaaggcaat gaacaaccac ctgcttgacc tgctgtccaa ggtgcagacc     240
aacctgttcg tgctgaagga gcacaagaac atcctgagcg agttcctgga cctgctgaat     300
atcgactcct ccgacaagag cctgatccag aaccactttc agatattccg gaacaccctg     360
ctgaacatcg agaaccacat ggactccctg aagaacgaga tttccgtgat caacccagcg     420
gtgttcgcga ccgtgagcgg cagcatcaag atcaacaaga tcaactacac cttcgccgag     480
gtgaagtaca gcgagaacga cgcctccggc aagcctaaga ggggcatcga gttcaaaccg     540
ggtggcaaca gatacgtgat cagcccgaac ccgcacctga caaccagta caacaactcc     600
ggacagaggc agttctactc cgcactggcg ctgaacatct catacagagg cgacgacgag     660
cactgggaga agaacaactg gccgaccaag acccaagata ggatcaccgc gctgggccag     720
aagtacaccc tgacctacga cggcaaggcc tga                                  753
```

<210> SEQ ID NO 73
<211> LENGTH: 250
<212> TYPE: PRT
<213> ORGANISM: Artificial Sequence
<220> FEATURE:
<223> OTHER INFORMATION: translated from synthesized maize optimized
      coding region

<400> SEQUENCE: 73

```
Met Ala Gln Ser Ser Arg Ile Cys His Gly Val Gln Asn Pro Cys Val
1               5                   10                  15

Ile Ile Ser Asn Leu Ser Lys Ser Asn Gln Asn Lys Ser Pro Phe Ser
            20                  25                  30

Val Ser Leu Lys Thr His Gln Gln Gln Arg Arg Ala Tyr Gln Ile Ser
        35                  40                  45

Ser Trp Gly Leu Lys Lys Ser Asn Asn Gly Ser Val Ile Arg Pro Val
    50                  55                  60

Lys Ala Met Asn Asn His Leu Leu Asp Leu Leu Ser Lys Val Gln Thr
65                  70                  75                  80

Asn Leu Phe Val Leu Lys Glu His Lys Asn Ile Leu Ser Glu Phe Leu
                85                  90                  95

Asp Leu Leu Asn Ile Asp Ser Ser Asp Lys Ser Leu Ile Gln Asn His
            100                 105                 110

Phe Gln Ile Phe Arg Asn Thr Leu Leu Asn Ile Glu Asn His Met Asp
        115                 120                 125

Ser Leu Lys Asn Glu Ile Ser Val Ile Asn Pro Ala Val Phe Ala Thr
    130                 135                 140

Val Ser Gly Ser Ile Lys Ile Asn Lys Ile Asn Tyr Thr Phe Ala Glu
145                 150                 155                 160

Val Lys Tyr Ser Glu Asn Asp Ala Ser Gly Lys Pro Lys Arg Gly Ile
                165                 170                 175

Glu Phe Lys Pro Gly Gly Asn Arg Tyr Val Ile Ser Pro Asn Pro His
            180                 185                 190

Leu Asn Asn Gln Tyr Asn Asn Ser Gly Gln Arg Gln Phe Tyr Ser Ala
        195                 200                 205
```

Leu Ala Leu Asn Ile Ser Tyr Arg Gly Asp Asp Glu His Trp Glu Lys
        210                 215                 220

Asn Asn Trp Pro Thr Lys Thr Gln Asp Arg Ile Thr Ala Leu Gly Gln
225                 230                 235                 240

Lys Tyr Thr Leu Thr Tyr Asp Gly Lys Ala
                245                 250

<210> SEQ ID NO 74
<211> LENGTH: 768
<212> TYPE: DNA
<213> ORGANISM: Artificial Sequence
<220> FEATURE:
<223> OTHER INFORMATION: Maize optimized

<400> SEQUENCE: 74
atgttggctc gccaaggagg atcactgaga gcctctcagt gtaacgctgg cctcgcgaga      60
cgcgtggagg tgggagcgtt ggttgttccg agacccataa gcgtcaacga cgtggttccc     120
catgtctatt cggctcctct gagcgtcgcg aggaggtcgt gctccaagtc atccatccgc     180
tcgactcgca gacttcagac aaccgtctgc tccatgaata atcacctgct tgacctgctg     240
tccaaggtgc agaccaacct gttcgtgctg aaggagcaca aaatatcct gagcgagttc      300 ctggacctat taaatatcga ctcctccgac aagagcctga tccagaacca ctttcagata     360
ttccggaaca ccctgctgaa catcgagaac cacatggact ccctgaagaa tgaaatttcc     420
gtaataaacc cagcggtgtt cgcgaccgtg agcggcagca ttaaaataaa caaaatcaac     480
tatacattcg ccgaggtgaa gtacagcgag aacgacgcct ccggcaagcc taagaggggc     540
atcgagttca aaccgggtgg caacagatac gtgatcagcc cgaacccgca cctgaataat     600
caatacaaca actccggaca gaggcagttc tactccgcac tggcattaaa catctcatac     660
agaggcgacg acgagcactg ggagaaaaat aattggccga ccaagaccca agataggatc     720
accgcgctgg gccaaaaata taccctgacc tacgacggca aggcctga               768

<210> SEQ ID NO 75
<211> LENGTH: 255
<212> TYPE: PRT
<213> ORGANISM: Artificial Sequence
<220> FEATURE:
<223> OTHER INFORMATION: translated from synthesized maize optimized
      coding region

<400> SEQUENCE: 75

Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
            20                  25                  30

Ile Ser Val Asn Asp Val Val Pro His Val Tyr Ser Ala Pro Leu Ser
        35                  40                  45

Val Ala Arg Arg Ser Cys Ser Lys Ser Ser Ile Arg Ser Thr Arg Arg
    50                  55                  60

Leu Gln Thr Thr Val Cys Ser Met Asn Asn His Leu Leu Asp Leu Leu
65                  70                  75                  80

Ser Lys Val Gln Thr Asn Leu Phe Val Leu Lys Glu His Lys Asn Ile
                85                  90                  95

Leu Ser Glu Phe Leu Asp Leu Leu Asn Ile Asp Ser Ser Asp Lys Ser
            100                 105                 110

Leu Ile Gln Asn His Phe Gln Ile Phe Arg Asn Thr Leu Leu Asn Ile
        115                 120                 125

Glu Asn His Met Asp Ser Leu Lys Asn Glu Ile Ser Val Ile Asn Pro
    130                 135                 140

Ala Val Phe Ala Thr Val Ser Gly Ser Ile Lys Ile Asn Lys Ile Asn
145                 150                 155                 160

Tyr Thr Phe Ala Glu Val Lys Tyr Ser Glu Asn Asp Ala Ser Gly Lys
                165                 170                 175

Pro Lys Arg Gly Ile Glu Phe Lys Pro Gly Gly Asn Arg Tyr Val Ile
            180                 185                 190

Ser Pro Asn Pro His Leu Asn Asn Gln Tyr Asn Asn Ser Gly Gln Arg
        195                 200                 205

Gln Phe Tyr Ser Ala Leu Ala Leu Asn Ile Ser Tyr Arg Gly Asp Asp
    210                 215                 220

Glu His Trp Glu Lys Asn Asn Trp Pro Thr Lys Thr Gln Asp Arg Ile
225                 230                 235                 240

Thr Ala Leu Gly Gln Lys Tyr Thr Leu Thr Tyr Asp Gly Lys Ala
                245                 250                 255

<210> SEQ ID NO 76
<211> LENGTH: 753
<212> TYPE: DNA
<213> ORGANISM: Artificial Sequence
<220> FEATURE:
<223> OTHER INFORMATION: Maize optimized

<400> SEQUENCE: 76

```
atggctcaat ctagcagaat ctgccacggt gtgcagaacc catgtgtgat catttccaat      60
ctctccaaat ccaaccagaa caaatctcct ttctcagtca gcctcaagac tcaccagcag     120
cagcgtcgtg cttaccagat atctagctgg ggattgaaga agtcaaacaa cgggtccgtg     180
attcgtccgg ttaaggcaat gaataatcac ctgcttgacc tgctgtccaa ggtgcagacc     240
aacctgttcg tgctgaagga gcacaaaaat atcctgagcg agttcctgga cctattaaat     300
atcgactcct ccgacaagag cctgatccag aaccactttc agatattccg gaacaccctg     360
ctgaacatcg agaaccacat ggactccctg aagaatgaaa tttccgtaat aaacccagcg     420
gtgttcgcga ccgtgagcgg cagcattaaa ataaacaaaa tcaactatac attcgccgag     480
gtgaagtaca gcgagaacga cgcctccggc aagcctaaga ggggcatcga gttcaaaccg     540
ggtggcaaca gatacgtgat cagcccgaac ccgcacctga ataatcaata caacaactcc     600
ggacagaggc agttctactc cgcactggca ttaaacatct catacagagg cgacgacgag     660
cactgggaga aaaataattg gccgaccaag acccaagata ggatcaccgc gctgggccaa     720
aaatatcccc tgacctacga cggcaaggcc tga                                   753
```

<210> SEQ ID NO 77
<211> LENGTH: 32
<212> TYPE: DNA
<213> ORGANISM: Artificial Sequence
<220> FEATURE:
<223> OTHER INFORMATION: synthesized primer oligonucleotide

<400> SEQUENCE: 77

```
ggatccgtcg tagtaccagt atgaccaagt tg                                     32
```

<210> SEQ ID NO 78
<211> LENGTH: 37
<212> TYPE: DNA
<213> ORGANISM: Artificial Sequence
<220> FEATURE:

```
<223> OTHER INFORMATION: synthesized primer oligonucleotide

<400> SEQUENCE: 78
ggtaccccaa aataatatct ttcttgaatt gtttctc 37

<210> SEQ ID NO 79
<211> LENGTH: 41
<212> TYPE: DNA
<213> ORGANISM: Artificial Sequence
<220> FEATURE:
<223> OTHER INFORMATION: synthesized primer oligonucleotide
<400> SEQUENCE: 79
actagtagga gtaaaaacac atatgaataa tcatttatta g 41

<210> SEQ ID NO 80
<211> LENGTH: 48
<212> TYPE: DNA
<213> ORGANISM: Artificial Sequence
<220> FEATURE:
<223> OTHER INFORMATION: synthesized primer oligonucleotide
<400> SEQUENCE: 80
ctcgagttat taagctttac catcatatgt taaagtatat ttttggcc 48

<210> SEQ ID NO 81
<211> LENGTH: 324
<212> TYPE: DNA
<213> ORGANISM: Bacillus thuringiensis
<400> SEQUENCE: 81
acagttagtg gatctattaa aataaacaaa atcaactata catttgctga agttaagtat 60
agtgaaaatg atgcaagtgg aaaacctaaa agaggaattg aatttaaacc tggcggaaat 120
cgatatgtaa tatctcctaa tccacatttg aataatcaat acaacaatag tggacaacga 180
caattttata gtgctttagc attaaatatt agctacagag gtgatgatga acattgggaa 240
aaaaataatt ggccaacaaa aactcaagat cgtattactg cacttggcca aaaatatact 300
ttaacatatg atggtaaagc ttaa 324

<210> SEQ ID NO 82
<211> LENGTH: 107
<212> TYPE: PRT
<213> ORGANISM: Bacillus thuringiensis

<400> SEQUENCE: 82

Thr Val Ser Gly Ser Ile Lys Ile Asn Lys Ile Asn Tyr Thr Phe Ala
1               5                   10                  15

Glu Val Lys Tyr Ser Glu Asn Asp Ala Ser Gly Lys Pro Lys Arg Gly
            20                  25                  30

Ile Glu Phe Lys Pro Gly Gly Asn Arg Tyr Val Ile Ser Pro Asn Pro
        35                  40                  45

His Leu Asn Asn Gln Tyr Asn Asn Ser Gly Gln Arg Gln Phe Tyr Ser
    50                  55                  60

Ala Leu Ala Leu Asn Ile Ser Tyr Arg Gly Asp Asp Glu His Trp Glu
65                  70                  75                  80

Lys Asn Asn Trp Pro Thr Lys Thr Gln Asp Arg Ile Thr Ala Leu Gly
                85                  90                  95

Gln Lys Tyr Thr Leu Thr Tyr Asp Gly Lys Ala
            100                 105
```

<210> SEQ ID NO 83
<211> LENGTH: 324
<212> TYPE: DNA
<213> ORGANISM: Bacillus thuringiensis

<400> SEQUENCE: 83

```
acagttagtg gatctattca aataaacaag gttaaatata catttgctga agttcagtac     60
agtggaaatg atgaaagtgg aaaacctaaa agaggaattg aatttaaatc cggtggaaat    120
cgatatgtaa tctctcctaa tccacattta ataatagat ataacaatgg tggacaacga    180
gatttttata atgctttagc attaaaagtt agcgatatag gtgatgatga aaatgggaa    240
aaaaatgaat ggccaacaaa aaatctaaca catcttagtg cgcttggtca aaaatatgat    300
ttacattatg atggcagagc ttaa                                           324
```

<210> SEQ ID NO 84
<211> LENGTH: 107
<212> TYPE: PRT
<213> ORGANISM: Bacillus thuringiensis

<400> SEQUENCE: 84

Thr Val Ser Gly Ser Ile Gln Ile Asn Lys Val Lys Tyr Thr Phe Ala
1               5                   10                  15

Glu Val Gln Tyr Ser Gly Asn Asp Glu Ser Gly Lys Pro Lys Arg Gly
            20                  25                  30

Ile Glu Phe Lys Ser Gly Gly Asn Arg Tyr Val Ile Ser Pro Asn Pro
        35                  40                  45

His Leu Asn Asn Arg Tyr Asn Gly Gly Gln Arg Asp Phe Tyr Asn
    50                  55                  60

Ala Leu Ala Leu Lys Val Ser Asp Ile Gly Asp Asp Glu Lys Trp Glu
65                  70                  75                  80

Lys Asn Glu Trp Pro Thr Lys Asn Leu Thr His Leu Ser Ala Leu Gly
                85                  90                  95

Gln Lys Tyr Asp Leu His Tyr Asp Gly Arg Ala
            100                 105

<210> SEQ ID NO 85
<211> LENGTH: 324
<212> TYPE: DNA
<213> ORGANISM: Bacillus thuringiensis

<400> SEQUENCE: 85

```
gcagttagtg gatctatccc aataaataat gtaaaatata catttgctga agttcagtac     60
agtggaaatg atgacagtgg aaaacctaaa agaggaatcg aatttaaatc aggaggaaac    120
cgatacgtaa tatctcctaa tccacattta ataatcgat ataacggtgg tggacaacga    180
gatttttata atgctttagc attaaaagtt agcgatatcg gtgatgatga acattgggaa    240
aaaaacaact ggccaacaaa gaatttaacg cgtcttagtg cacttggtca aaaatatgat    300
ttacattatg atggtagagc ttaa                                           324
```

<210> SEQ ID NO 86
<211> LENGTH: 107
<212> TYPE: PRT
<213> ORGANISM: Bacillus thuringiensis

<400> SEQUENCE: 86

Ala Val Ser Gly Ser Ile Pro Ile Asn Asn Val Lys Tyr Thr Phe Ala
1               5                   10                  15

Glu Val Gln Tyr Ser Gly Asn Asp Asp Ser Gly Lys Pro Lys Arg Gly
            20                  25                  30

Ile Glu Phe Lys Ser Gly Gly Asn Arg Tyr Val Ile Ser Pro Asn Pro
        35                  40                  45

His Leu Asn Asn Arg Tyr Asn Gly Gly Gly Arg Asp Phe Tyr Asn
 50                  55                  60

Ala Leu Ala Leu Lys Val Ser Asp Ile Gly Asp Glu His Trp Glu
65                  70                  75                  80

Lys Asn Asn Trp Pro Thr Lys Asn Leu Thr Arg Leu Ser Ala Leu Gly
                85                  90                  95

Gln Lys Tyr Asp Leu His Tyr Asp Gly Arg Ala
            100                 105

<210> SEQ ID NO 87
<211> LENGTH: 327
<212> TYPE: DNA
<213> ORGANISM: Bacillus thuringiensis

<400> SEQUENCE: 87
acagtaagtg ggaatattac agtaaataag atcaaatata catttgcaga atccaatat      60 agcggaaatg atgaaagtgg acgtcctaaa agaggaattg aatttaaaca aggaggaaat   120
cgatacgtaa tatctcctaa tccacattta aatactcgat ataatactag tggaggacct   180
cgagattttt ataatgcttt agcattaaat cttagctata gaggtgacga tgaacattgg   240 gaaaaaata attggccaac aaaaaatcaa gaccgtctta atgcacttgg agaaagatat   300
actttaaaat atgatggtag agcttaa                                        327

<210> SEQ ID NO 88
<211> LENGTH: 108
<212> TYPE: PRT
<213> ORGANISM: Bacillus thuringiensis

<400> SEQUENCE: 88

Thr Val Ser Gly Asn Ile Thr Val Asn Lys Ile Lys Tyr Thr Phe Ala
1               5                   10                  15

Glu Ile Gln Tyr Ser Gly Asn Asp Glu Ser Gly Arg Pro Lys Arg Gly
            20                  25                  30

Ile Glu Phe Lys Gln Gly Gly Asn Arg Tyr Val Ile Ser Pro Asn Pro
        35                  40                  45

His Leu Asn Thr Arg Tyr Asn Thr Ser Gly Pro Arg Asp Phe Tyr
 50                  55                  60

Asn Ala Leu Ala Leu Asn Leu Ser Tyr Arg Gly Asp Asp Glu His Trp
65                  70                  75                  80

Glu Lys Asn Asn Trp Pro Thr Lys Asn Gln Asp Arg Leu Asn Ala Leu
                85                  90                  95

Gly Glu Arg Tyr Thr Leu Lys Tyr Asp Gly Arg Ala
            100                 105

<210> SEQ ID NO 89
<211> LENGTH: 324
<212> TYPE: DNA
<213> ORGANISM: Bacillus thuringiensis

<400> SEQUENCE: 89
acagttagtg gatctattca aataaacaag gttaaatata catttgctga agttcagtac      60
agtggaaatg atgaaagtgg aaaacctaaa agaggaattg aatttaaatc cggtggaaat    120

```
cgatatgtaa tctctcctaa tccacattta aataatagat ataacaatgg tggacaacga    180
gatttttata atgctttagc attaaaagtt agcgatatag gtgatgatga aaaatgggaa    240
aaaaatgaat ggccaacaaa aaatctaaca catcttagtg cgcttggtca aaaatatgat    300
ttacattatg atggcagagc ttaa                                          324
```

<210> SEQ ID NO 90
<211> LENGTH: 107
<212> TYPE: PRT
<213> ORGANISM: Bacillus thuringiensis

<400> SEQUENCE: 90

```
Thr Val Ser Gly Ser Ile Gln Ile Asn Lys Val Lys Tyr Thr Phe Ala
1               5                   10                  15

Glu Val Gln Tyr Ser Gly Asn Asp Glu Ser Gly Lys Pro Lys Arg Gly
                20                  25                  30

Ile Glu Phe Lys Ser Gly Gly Asn Arg Tyr Val Ile Ser Pro Asn Pro
            35                  40                  45

His Leu Asn Asn Arg Tyr Asn Asn Gly Gly Gln Arg Asp Phe Tyr Asn
        50                  55                  60

Ala Leu Ala Leu Lys Val Ser Asp Ile Gly Asp Asp Glu Lys Trp Glu
65                  70                  75                  80

Lys Asn Glu Trp Pro Thr Lys Asn Leu Thr His Leu Ser Ala Leu Gly
                85                  90                  95

Gln Lys Tyr Asp Leu His Tyr Asp Gly Arg Ala
            100                 105
```

<210> SEQ ID NO 91
<211> LENGTH: 327
<212> TYPE: DNA
<213> ORGANISM: Bacillus thuringiensis

<400> SEQUENCE: 91

```
acagttagcg gaaaataat aataaatact attaaatata cattcgcaga agttcaatat     60
agtggaaatg atgaaagtgg tagacctaaa gagggattg agtttaaacc aggaggaaat    120
cgatatatta tttctcctaa tccacattta aataataaat ataatacttc aaatggtcca    180
atacaatttt ataatgcttt agcattaaat cttagttata aaggagatga tgaacagtgg    240
gtaaagggga attggccaaa aacaaatcta agtggtctta ttcgcttgg acaaaaatat    300 attttaaaat atgacagtag taattaa                                       327
```

<210> SEQ ID NO 92
<211> LENGTH: 108
<212> TYPE: PRT
<213> ORGANISM: Bacillus thuringiensis

<400> SEQUENCE: 92

```
Thr Val Ser Gly Lys Ile Ile Asn Thr Ile Lys Tyr Thr Phe Ala
1               5                   10                  15

Glu Val Gln Tyr Ser Gly Asn Asp Glu Ser Gly Arg Pro Lys Arg Gly
                20                  25                  30

Ile Glu Phe Lys Pro Gly Gly Asn Arg Tyr Ile Ile Ser Pro Asn Pro
            35                  40                  45

His Leu Asn Asn Lys Tyr Asn Thr Ser Asn Gly Pro Ile Gln Phe Tyr
        50                  55                  60

Asn Ala Leu Ala Leu Asn Leu Ser Tyr Lys Gly Asp Asp Glu Gln Trp
```

```
                65                  70                  75                  80
Val Lys Gly Asn Trp Pro Lys Thr Asn Leu Ser Gly Leu Asn Ser Leu
                    85                  90                  95

Gly Gln Lys Tyr Ile Leu Lys Tyr Asp Ser Ser Asn
            100                 105
```

<210> SEQ ID NO 93
<211> LENGTH: 333
<212> TYPE: DNA
<213> ORGANISM: Bacillus thuringiensis

<400> SEQUENCE: 93

```
gcagtatctg gaacgattat tatcaataat aaaaattata catttgtaga agtgcaatat      60
agccaaagtg atcaatatgg accaaaaaga ggaattaaat ttacaggtgg aggaaatgaa     120
tatttaattg atcccaatcc acatgaaaat ggacaatatc aaaaaaacgc cagacaattt     180
tatagtgctt tagcatatgg tatacaaggg aagtctataa cagatggaca aaatgggcat     240
ccttgggtac aaataattg gcccacaggc aatcaagatc ggattaatgc actaggagaa      300
agatatacat tacaatacaa aggtagagct taa                                  333
```

<210> SEQ ID NO 94
<211> LENGTH: 110
<212> TYPE: PRT
<213> ORGANISM: Bacillus thuringiensis

<400> SEQUENCE: 94

```
Ala Val Ser Gly Thr Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
                20                  25                  30

Lys Phe Thr Gly Gly Gly Asn Glu Tyr Leu Ile Asp Pro Asn Pro His
            35                  40                  45

Glu Asn Gly Gln Tyr Gln Lys Asn Ala Arg Gln Phe Tyr Ser Ala Leu
        50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Gly Asn Gln Asp Arg Ile Asn
                85                  90                  95

Ala Leu Gly Glu Arg Tyr Thr Leu Gln Tyr Lys Gly Arg Ala
            100                 105                 110
```

<210> SEQ ID NO 95
<211> LENGTH: 333
<212> TYPE: DNA
<213> ORGANISM: Bacillus thuringiensis

<400> SEQUENCE: 95

```
gcagtatctg gaacgattat tatcaataat aaaaattata catttgtaga agtgcaatat      60
agccaaagtg atcaatatgg accaaaaaga gggattaaat ttacaggtgg aggaaatgaa     120
tatttaattg atcccaatcc acatgaaaat ggacaatatc aaaaaaacgc cagacaattt     180
tatagtgctt tagcatatgg tatacaaggg aagtctataa cagatggaca aaatgggcat     240
ccttgggtac caataattg gcccacaggc aatcaagatc ggattaatgc actaggagaa      300
agatatacat tacaatacaa aggtagagct taa                                  333
```

<210> SEQ ID NO 96

<211> LENGTH: 110
<212> TYPE: PRT
<213> ORGANISM: Bacillus thuringiensis

<400> SEQUENCE: 96

```
Ala Val Ser Gly Thr Ile Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
            20                  25                  30

Lys Phe Thr Gly Gly Gly Asn Glu Tyr Leu Ile Asp Pro Asn Pro His
        35                  40                  45

Glu Asn Gly Gln Tyr Gln Lys Asn Ala Arg Gln Phe Tyr Ser Ala Leu
    50                  55                  60

Ala Tyr Gly Ile Gln Gly Lys Ser Ile Thr Asp Gly Gln Asn Gly His
65                  70                  75                  80

Pro Trp Val Pro Asn Asn Trp Pro Thr Gly Asn Gln Asp Arg Ile Asn
                85                  90                  95

Ala Leu Gly Glu Arg Tyr Thr Leu Gln Tyr Lys Gly Arg Ala
            100                 105                 110
```

<210> SEQ ID NO 97
<211> LENGTH: 333
<212> TYPE: DNA
<213> ORGANISM: Bacillus thuringiensis

<400> SEQUENCE: 97

```
gcagtatctg gaacgattat tatcaataat aaaaattata cctttgtaga agtacaatat      60
agccaaagtg atcaatatgg accaaaaaga gggattaaat ttacaggtgg aggaaatgaa     120
tatttaattg atcccaatcc acatgaaaat ggacaatatc aaaaaaacgc tagacaattt     180
tatagtgctt tagcatatgg tatacaaggg aagtctataa cagatggaca aaatgggcat     240
ccttgggtac aaaataattg gcccacagtc aatcaagatc ggattaatgc actaggagaa     300
agatatacat tacaatacaa aggtagggct taa                                  333
```

<210> SEQ ID NO 98
<211> LENGTH: 110
<212> TYPE: PRT
<213> ORGANISM: Bacillus thuringiensis

<400> SEQUENCE: 98

```
Ala Val Ser Gly Thr Ile Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
            20                  25                  30

Lys Phe Thr Gly Gly Gly Asn Glu Tyr Leu Ile Asp Pro Asn Pro His
        35                  40                  45

Glu Asn Gly Gln Tyr Gln Lys Asn Ala Arg Gln Phe Tyr Ser Ala Leu
    50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Val Asn Gln Asp Arg Ile Asn
                85                  90                  95

Ala Leu Gly Glu Arg Tyr Thr Leu Gln Tyr Lys Gly Arg Ala
            100                 105                 110
```

<210> SEQ ID NO 99
<211> LENGTH: 333

```
<212> TYPE: DNA
<213> ORGANISM: Bacillus thuringiensis

<400> SEQUENCE: 99
gcagtatctg gaacgattat tatcaataat aaaaattata catttgtaga agtgcaatat      60
agccaaagtg atcaatatgg accaaaaaga gggattaaat ttacaggtgg aggaaatgaa     120
tatttaattg atcccaatcc acatgaaaat ggacaatatc aaaaaaacgc cagacaattt     180
tatagtgctt tagcatatgg tatacaaggg aagtctataa cagatggaca aaatgggcat     240
ccttgggtac aaaataattg gcccacaggc aatcaagatc ggattaatgc actaggagaa     300
agatatacat acaatacaa aggtagagct taa                                    333

<210> SEQ ID NO 100
<211> LENGTH: 110
<212> TYPE: PRT
<213> ORGANISM: Bacillus thuringiensis

<400> SEQUENCE: 100

Ala Val Ser Gly Thr Ile Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
            20                  25                  30

Lys Phe Thr Gly Gly Gly Asn Glu Tyr Leu Ile Asp Pro Asn Pro His
        35                  40                  45

Glu Asn Gly Gln Tyr Gln Lys Asn Ala Arg Gln Phe Tyr Ser Ala Leu
    50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Gly Asn Gln Asp Arg Ile Asn
                85                  90                  95

Ala Leu Gly Glu Arg Tyr Thr Leu Gln Tyr Lys Gly Arg Ala
            100                 105                 110

<210> SEQ ID NO 101
<211> LENGTH: 348
<212> TYPE: DNA
<213> ORGANISM: Bacillus thuringiensis

<400> SEQUENCE: 101
gccgtatcgt tgtctctgat ttttgctctt gctgtcattg tatttccttt ctccgcctcg      60
aatgtagaag ctaagggtgt aagcggcacg atcaaaatca ataacgaaac ctataaatat     120
atcgaagaat cgttcggaaa aaaccggggc attacattca atccaggtaa tcacacgtat     180
acaatatctc caaatccaca caataatcct aaatataata aaaaacaagt tcagttctat     240
gccgagattg caaatggcgt taaagcccag gtggaaagat ccgggtggaa aaactccttt     300
accggcattc aagcgttagg ggaaacctat acattaagcc cgcgttaa                  348

<210> SEQ ID NO 102
<211> LENGTH: 115
<212> TYPE: PRT
<213> ORGANISM: Bacillus thuringiensis

<400> SEQUENCE: 102

Ala Val Ser Leu Ser Leu Ile Phe Ala Leu Ala Val Ile Val Phe Pro
1               5                   10                  15

Phe Ser Ala Ser Asn Val Glu Ala Lys Gly Val Ser Gly Thr Ile Lys
            20                  25                  30
```

```
Ile Asn Asn Glu Thr Tyr Lys Tyr Ile Glu Glu Ser Phe Gly Lys Asn
            35                  40                  45

Arg Gly Ile Thr Phe Asn Pro Gly Asn His Thr Tyr Thr Ile Ser Pro
 50                  55                  60

Asn Pro His Asn Pro Lys Tyr Asn Lys Gln Val Gln Phe Tyr
 65                  70                  75                  80

Ala Glu Ile Ala Asn Gly Val Lys Ala Gln Val Glu Arg Ser Gly Trp
                85                  90                  95

Lys Asn Ser Phe Thr Gly Ile Gln Ala Leu Gly Glu Thr Tyr Thr Leu
            100                 105                 110

Ser Pro Arg
        115

<210> SEQ ID NO 103
<211> LENGTH: 306
<212> TYPE: DNA
<213> ORGANISM: Bacillus thuringiensis

<400> SEQUENCE: 103
gtagttagtg gcaaagaaaa aattaataat attaattata gatatgaaga aattagattt      60
ggcggaactg atagaggact caaatataca gcagatggtt attcactttc aactgctgtt     120
tcatataaaa taagtcctga tccacataat aatagtgatt ataataatag tccaccaaga     180
ttttattctg ctatgtcaga tagaattgaa agaataggta cttctgctaa atggactcca     240
ggaaattggc caagaaccat aaatgttaag gtatctaaag aaaattatac tttaactaaa     300
caataa                                                                306

<210> SEQ ID NO 104
<211> LENGTH: 101
<212> TYPE: PRT
<213> ORGANISM: Bacillus thuringiensis

<400> SEQUENCE: 104

Val Val Ser Gly Lys Glu Lys Ile Asn Asn Ile Asn Tyr Arg Tyr Glu
 1               5                  10                  15

Glu Ile Arg Phe Gly Gly Thr Asp Arg Gly Leu Lys Tyr Thr Ala Asp
                20                  25                  30

Gly Tyr Ser Leu Ser Thr Ala Val Ser Tyr Lys Ile Ser Pro Asp Pro
            35                  40                  45

His Asn Asn Ser Asp Tyr Asn Asn Ser Pro Pro Arg Phe Tyr Ser Ala
 50                  55                  60

Met Ser Asp Arg Ile Glu Arg Ile Gly Thr Ser Ala Lys Trp Thr Pro
 65                  70                  75                  80

Gly Asn Trp Pro Arg Thr Ile Asn Val Lys Val Ser Lys Glu Asn Tyr
                85                  90                  95

Thr Leu Thr Lys Gln
            100

<210> SEQ ID NO 105
<211> LENGTH: 273
<212> TYPE: DNA
<213> ORGANISM: Bacillus thuringiensis

<400> SEQUENCE: 105
ggggtaagtg gctcaatcac gatcaacaaa gagacctata atatatcga agaatctttc       60 ggaaaaaatc gagggattac attcaatcca ggccagcata cttacaaaat aaccccgaat     120
```

```
cctcacgaca atcccaaata caacaaaaaa caagagcagt tttatgagga aatcgcaaaa    180
ggcgttaaaa ctcttgtaga aaaatcaggc tggaaagata cgctcagcaa cattacagct    240
ctgggtgaaa cctatacatt agctccacgc taa                                 273
```

<210> SEQ ID NO 106
<211> LENGTH: 90
<212> TYPE: PRT
<213> ORGANISM: Bacillus thuringiensis

<400> SEQUENCE: 106

```
Gly Val Ser Gly Ser Ile Thr Ile Asn Lys Glu Thr Tyr Lys Tyr Ile
1               5                   10                  15

Glu Glu Ser Phe Gly Lys Asn Arg Gly Ile Thr Phe Asn Pro Gly Gln
            20                  25                  30

His Thr Tyr Lys Ile Thr Pro Asn Pro His Asp Asn Pro Lys Tyr Asn
        35                  40                  45

Lys Lys Gln Glu Gln Phe Tyr Glu Glu Ile Ala Lys Gly Val Lys Thr
    50                  55                  60

Leu Val Glu Lys Ser Gly Trp Lys Asp Thr Leu Ser Asn Ile Thr Ala
65                  70                  75                  80

Leu Gly Glu Thr Tyr Thr Leu Ala Pro Arg
                85                  90
```

<210> SEQ ID NO 107
<211> LENGTH: 333
<212> TYPE: DNA
<213> ORGANISM: Bacillus thuringiensis

<400> SEQUENCE: 107

```
gcagtatctg gaacgattat tatcaataat aaaaattata catttgtaga agtgcaatat    60
agccaaagtg atcaatatgg accaaaaaga gggattaaat ttacaggtgg aggaaatgaa    120
tatttaattg atcccaatcc acatgaaaat ggacaatatc aaaaaaacgc cagacaattt    180
tatagtgctt tagcatatgg tatacaaggg aagtctataa cagatggaca aaatgggcat    240
ccttgggtac aaaataattg gcccacaggc aatcaagatc ggattaatgc actaggagaa    300
agatatacat tacaatacaa agggagagct taa                                 333
```

<210> SEQ ID NO 108
<211> LENGTH: 110
<212> TYPE: PRT
<213> ORGANISM: Bacillus thuringiensis

<400> SEQUENCE: 108

```
Ala Val Ser Gly Thr Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
            20                  25                  30

Lys Phe Thr Gly Gly Gly Asn Glu Tyr Leu Ile Asp Pro Asn Pro His
        35                  40                  45

Glu Asn Gly Gln Tyr Gln Lys Asn Ala Arg Gln Phe Tyr Ser Ala Leu
    50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Gly Asn Gln Asp Arg Ile Asn
                85                  90                  95
```

Ala Leu Gly Glu Arg Tyr Thr Leu Gln Tyr Lys Gly Arg Ala
            100                 105                 110

<210> SEQ ID NO 109
<211> LENGTH: 330
<212> TYPE: DNA
<213> ORGANISM: Bacillus thuringiensis

<400> SEQUENCE: 109
gcagtatctg gaacaattat tataaataat gcaatttatg catttacaga agtgcattat       60
agtcaaagtg atgaatatgg gcctaaaaga ggtattaaat ttacaagagg aaatgaatat     120
ttaattgatc caaatccaca tgaaaatggt caatatcaaa aaagtgcaag ccaattttat     180
agcgctttag catatggtgt acaaggtaaa tcaataacag atggacaaga cggacatcct     240
tggaaaaaaa atgattggcc cacaaaaaac ctagatcgca ttaatgtgct cggagaaaga     300
tatactttac tctatcaaca tagagattaa                                     330

<210> SEQ ID NO 110
<211> LENGTH: 109
<212> TYPE: PRT
<213> ORGANISM: Bacillus thuringiensis

<400> SEQUENCE: 110

Ala Val Ser Gly Thr Ile Ile Ile Asn Asn Ala Ile Tyr Ala Phe Thr
1               5                   10                  15

Glu Val His Tyr Ser Gln Ser Asp Glu Tyr Gly Pro Lys Arg Gly Ile
            20                  25                  30

Lys Phe Thr Arg Gly Asn Glu Tyr Leu Ile Asp Pro Asn Pro His Glu
        35                  40                  45

Asn Gly Gln Tyr Gln Lys Ser Ala Ser Gln Phe Tyr Ser Ala Leu Ala
    50                  55                  60

Tyr Gly Val Gln Gly Lys Ser Ile Thr Asp Gly Gln Asp Gly His Pro
65                  70                  75                  80

Trp Lys Lys Asn Asp Trp Pro Thr Lys Asn Leu Asp Arg Ile Asn Val
                85                  90                  95

Leu Gly Glu Arg Tyr Thr Leu Leu Tyr Gln His Arg Asp
            100                 105

<210> SEQ ID NO 111
<211> LENGTH: 333
<212> TYPE: DNA
<213> ORGANISM: Bacillus thuringiensis

<400> SEQUENCE: 111
gcagtatctg gaacgattat tatcaataat aaaaattata catttgtaga agtgcaatat       60
agccaaagtg atcaatatgg accaaaaaga gggattaaat ttacaggtgg aggaaatgaa     120
tatttaattg atcccaatcc acatgaaaat ggacaatatc aaaaaaacgc cagacaattt     180
tatagtgctt tagcatatgg tatacaaggg aagtctataa cagatggaca aaatgggcat     240
ccttgggtac aaaataattg gcccacaggc aatcaagatc ggattaatgc actaggagaa     300
agatatacat tacaatacaa aggtagagct taa                                 333

<210> SEQ ID NO 112
<211> LENGTH: 110
<212> TYPE: PRT
<213> ORGANISM: Bacillus thuringiensis

<400> SEQUENCE: 112

Ala Val Ser Gly Thr Ile Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
                20                  25                  30

Lys Phe Thr Gly Gly Gly Asn Glu Tyr Leu Ile Asp Pro Asn Pro His
            35                  40                  45

Glu Asn Gly Gln Tyr Gln Lys Asn Ala Arg Gln Phe Tyr Ser Ala Leu
        50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Gly Asn Gln Asp Arg Ile Asn
                85                  90                  95

Ala Leu Gly Glu Arg Tyr Thr Leu Gln Tyr Lys Gly Arg Ala
            100                 105                 110

<210> SEQ ID NO 113
<211> LENGTH: 333
<212> TYPE: DNA
<213> ORGANISM: Bacillus thuringiensis

<400> SEQUENCE: 113
gcagtatctg gaacgattat tatcaataat aaaaattata catttgtaga agtgcaatat       60
agccaaagtg atcaatatgg accaaaaaga gggattaaat ttacaggtgg aggaaatgaa      120
tatttaattg atcccaatcc acatgaaaat ggacaatatc aaaaaaacgc cagacaattt      180
tatagtgctt tagcatatgg tatacaaggg aagtctataa cagatggaca aaatgggcat      240
ccttgggtac aaaataattg gcccacaggc aatcaagatc ggattaatgc actaggagaa      300
agatatacat tacaatacaa aggtagagct taa                                   333

<210> SEQ ID NO 114
<211> LENGTH: 110
<212> TYPE: PRT
<213> ORGANISM: Bacillus thuringiensis

<400> SEQUENCE: 114

Ala Val Ser Gly Thr Ile Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
                20                  25                  30

Lys Phe Thr Gly Gly Gly Asn Glu Tyr Leu Ile Asp Pro Asn Pro His
            35                  40                  45

Glu Asn Gly Gln Tyr Gln Lys Asn Ala Arg Gln Phe Tyr Ser Ala Leu
        50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Gly Asn Gln Asp Arg Ile Asn
                85                  90                  95

Ala Leu Gly Glu Arg Tyr Thr Leu Gln Tyr Lys Gly Arg Ala
            100                 105                 110

<210> SEQ ID NO 115
<211> LENGTH: 333
<212> TYPE: DNA
<213> ORGANISM: Bacillus thuringiensis

<400> SEQUENCE: 115

```
gcagtatctg aacgattat tatcaataat aaaaattata catttgtaga agtgcaatat    60
agccaaagtg atcaatatgg accaaaaaga gggattaaat ttacaggtgg aggaaatgaa   120
tatttaattg atcccaatcc acatgaaaat ggacaatatc aaaaaaacgc cagacaattt   180
tatagtgctt tagcatatgg tatacaaggg aagtctataa cagatggaca aaatgggcat   240
ccttgggtac aaaataattg gcccacaggc aatcaagatc ggattaatgc actaggagaa   300
agatatacat acaatacaa aggtagagct taa                                 333
```

<210> SEQ ID NO 116
<211> LENGTH: 110
<212> TYPE: PRT
<213> ORGANISM: Bacillus thuringiensis

<400> SEQUENCE: 116

```
Ala Val Ser Gly Thr Ile Ile Asn Asn Lys Asn Tyr Thr Phe Val
1               5                   10                  15

Glu Val Gln Tyr Ser Gln Ser Asp Gln Tyr Gly Pro Lys Arg Gly Ile
            20                  25                  30

Lys Phe Thr Gly Gly Gly Asn Glu Tyr Leu Ile Asp Pro Asn Pro His
        35                  40                  45

Glu Asn Gly Gln Tyr Gln Lys Asn Ala Arg Gln Phe Tyr Ser Ala Leu
    50                  55                  60

Ala Tyr Gly Ile Gln Gly Lys Ser Ile Thr Asp Gly Gln Asn Gly His
65                  70                  75                  80

Pro Trp Val Gln Asn Asn Trp Pro Thr Gly Asn Gln Asp Arg Ile Asn
                85                  90                  95

Ala Leu Gly Glu Arg Tyr Thr Leu Gln Tyr Lys Gly Arg Ala
            100                 105                 110
```

<210> SEQ ID NO 117
<211> LENGTH: 348
<212> TYPE: DNA
<213> ORGANISM: Bacillus thuringiensis

<400> SEQUENCE: 117

```
gccgtatcat tgtctttgtt tttggcccctt gctttaatcg tgcttccttt ctccggcgct    60
aatgtagaag ctaaagggt aagtggctca atcacgatca agaaagaaac atataaatat    120
atcgaagaat ctttcggaaa aaaccgaggg attacattca atccaggcca acatacgtac   180
aaaataactc cgaatcctca cgacaatccc aagtataaca aaaaacaaga gcagttttat   240
gaggaaatcg caaaagccgt taaagtctt gtagaaaaat caggctggaa agacaccttc   300
agcaacatta cagctctggg tgaaacctat acattagctc cacgctaa               348
```

<210> SEQ ID NO 118
<211> LENGTH: 115
<212> TYPE: PRT
<213> ORGANISM: Bacillus thuringiensis

<400> SEQUENCE: 118

```
Ala Val Ser Leu Ser Leu Phe Leu Ala Leu Ala Leu Ile Val Leu Pro
1               5                   10                  15

Phe Ser Gly Ala Asn Val Glu Ala Lys Gly Val Ser Gly Ser Ile Thr
            20                  25                  30

Ile Lys Lys Glu Thr Tyr Lys Tyr Ile Glu Glu Ser Phe Gly Lys Asn
        35                  40                  45

Arg Gly Ile Thr Phe Asn Pro Gly Gln His Thr Tyr Lys Ile Thr Pro
```

```
                     50                  55                  60

Asn Pro His Asp Asn Pro Lys Tyr Asn Lys Lys Gln Glu Gln Phe Tyr
 65                  70                  75                  80

Glu Glu Ile Ala Lys Ala Val Lys Ser Leu Val Glu Lys Ser Gly Trp
                 85                  90                  95

Lys Asp Thr Phe Ser Asn Ile Thr Ala Leu Gly Glu Thr Tyr Thr Leu
                100                 105                 110

Ala Pro Arg
        115

<210> SEQ ID NO 119
<211> LENGTH: 348
<212> TYPE: DNA
<213> ORGANISM: Bacillus thuringiensis

<400> SEQUENCE: 119
gccgtatcat tgtccctgtt tttggccatt gctttaatcg tgcttccttt ctccggcact      60
aatgtagatg ctaaaggggt aagtggctca atcacgatca caaagaaac ctataaatat     120 atcgaagaat ctttcggaaa aaatcgaggg attacattca atccaggcca gcatacgtac    180
aaaataaccc cgaatcctca cgacaatccc aaatacaaca aaaaacaaga gcagttttat    240
gaggaaatcg caaaaggcgt taaaactctt gtagaaaaat caggctggaa agatacgctc    300
agcaacatta cagctctggg tgaaacctat acattagctc cacgctaa                 348

<210> SEQ ID NO 120
<211> LENGTH: 115
<212> TYPE: PRT
<213> ORGANISM: Bacillus thuringiensis

<400> SEQUENCE: 120

Ala Val Ser Leu Ser Leu Phe Leu Ala Ile Ala Leu Ile Val Leu Pro
  1               5                  10                  15

Phe Ser Gly Thr Asn Val Asp Ala Lys Gly Val Ser Gly Ser Ile Thr
                 20                  25                  30

Ile Asn Lys Glu Thr Tyr Lys Tyr Ile Glu Glu Ser Phe Gly Lys Asn
             35                  40                  45

Arg Gly Ile Thr Phe Asn Pro Gly Gln His Thr Tyr Lys Ile Thr Pro
         50                  55                  60

Asn Pro His Asp Asn Pro Lys Tyr Asn Lys Lys Gln Glu Gln Phe Tyr
 65                  70                  75                  80

Glu Glu Ile Ala Lys Gly Val Lys Thr Leu Val Glu Lys Ser Gly Trp
                 85                  90                  95

Lys Asp Thr Leu Ser Asn Ile Thr Ala Leu Gly Glu Thr Tyr Thr Leu
                100                 105                 110

Ala Pro Arg
        115

<210> SEQ ID NO 121
<211> LENGTH: 624
<212> TYPE: DNA
<213> ORGANISM: Bacillus thuringiensis

<400> SEQUENCE: 121
atgtctttct tgaactgttt ccctttaaaa tatcttatgt ggatgctcc tcactctatt      60 ttgaaaaagt ttagcttact ttcaaaaatt caaactaatt tatttgtttt aaagaacaa     120 aaaaatactt tttcagaatt tctaaattta ttaaatatag attcatcaga ccaatctcta    180
```

```
attcaaaaat atcttcaagt ttttgaaaac agcctatttta atatagagaa tcatgttgat      240
gttcttaaaa atgaaatatc agtattagat ccagatattt ttgcaacagt tagtgggtct      300
attacaataa ataatgtcaa atatacattt gctgaagttc aatacagtgg aaatgatgaa      360
agtggacgtc ctaaaagagg aattgaattt aaaccagggg gaaatcgata cgtaatatct      420
cctaatccac atttgaataa tcaatataac agcaatggac aacgacagtt ttatagtgct      480
ttagcatatg gtatacaaac caaatctata acgatggaa atactggaca ctcttgggag       540
aaaagcaatt ggccaacaat aaatcaagat cgtataaatg cacttggggt aagatatact      600
ttgaaatatg atggtagagc ttag                                             624
```

<210> SEQ ID NO 122
<211> LENGTH: 207
<212> TYPE: PRT
<213> ORGANISM: Bacillus thuringiensis

<400> SEQUENCE: 122

```
Met Ser Phe Leu Asn Cys Phe Pro Leu Lys Tyr Leu Met Leu Asp Ala
1               5                   10                  15
Pro His Ser Ile Leu Lys Lys Phe Ser Leu Leu Ser Lys Ile Gln Thr
            20                  25                  30
Asn Leu Phe Val Leu Lys Glu Gln Lys Asn Thr Phe Ser Glu Phe Leu
        35                  40                  45
Asn Leu Leu Asn Ile Asp Ser Ser Asp Gln Ser Leu Ile Gln Lys Tyr
    50                  55                  60
Leu Gln Val Phe Glu Asn Ser Leu Phe Asn Ile Glu Asn His Val Asp
65                  70                  75                  80
Val Leu Lys Asn Glu Ile Ser Val Leu Asp Pro Asp Ile Phe Ala Thr
                85                  90                  95
Val Ser Gly Ser Ile Thr Ile Asn Asn Val Lys Tyr Thr Phe Ala Glu
            100                 105                 110
Val Gln Tyr Ser Gly Asn Asp Glu Ser Gly Arg Pro Lys Arg Gly Ile
        115                 120                 125
Glu Phe Lys Pro Gly Gly Asn Arg Tyr Val Ile Ser Pro Asn Pro His
    130                 135                 140
Leu Asn Asn Gln Tyr Asn Ser Asn Gly Gln Arg Gln Phe Tyr Ser Ala
145                 150                 155                 160
Leu Ala Tyr Gly Ile Gln Thr Lys Ser Ile Asn Asp Gly Asn Thr Gly
                165                 170                 175
His Ser Trp Glu Lys Ser Asn Trp Pro Thr Ile Asn Gln Asp Arg Ile
            180                 185                 190
Asn Ala Leu Gly Val Arg Tyr Thr Leu Lys Tyr Asp Gly Arg Ala
        195                 200                 205
```

<210> SEQ ID NO 123
<211> LENGTH: 579
<212> TYPE: DNA
<213> ORGANISM: Bacillus thuringiensis

<400> SEQUENCE: 123

```
atggataatc atttattagg gttactttca aaaatccaaa acaatgtttt tgttctaaaa       60
gaacaaaaac gcagtgtttc agaatttta aatctattag atatagattc atctaatcaa      120
tttttaattc aacatatttt tcaaatgttt gaacacagct tatttaatat cgagaattat      180
gttgattctc ttacagatga aatatcaata ttaaaccctt ctagtttcat agcagttagt      240
```

```
ggaaatatat atgtaggtag acaacaagat aggtactcat ttgtagaaat tcagtatact    300
cagaatgata gttcgggaag acctaaaaga ggaatcacat ttacatcagg agcaattaag    360
tatgatatat cccctaatcc tcatttaagt aaagcatata ataataacgg acaacgagat    420
ttttataata gcttagcatt aaaagttcgt gattacgcca cagatcataa ttgggttaga    480
ggtggttggg attattctca gaaattaact tttaatttaa gtggatttag tggtagtgaa    540
ggtagtagat acaccttgac acctgtagct aaaacttaa                          579
```

<210> SEQ ID NO 124
<211> LENGTH: 192
<212> TYPE: PRT
<213> ORGANISM: Bacillus thuringiensis

<400> SEQUENCE: 124

```
Met Asp Asn His Leu Leu Gly Leu Leu Ser Lys Ile Gln Asn Asn Val
1               5                   10                  15

Phe Val Leu Lys Glu Gln Lys Arg Ser Val Ser Glu Phe Leu Asn Leu
            20                  25                  30

Leu Asp Ile Asp Ser Ser Asn Gln Phe Leu Ile Gln Gln Tyr Phe Gln
        35                  40                  45

Met Phe Glu His Ser Leu Phe Asn Ile Glu Asn Tyr Val Asp Ser Leu
    50                  55                  60

Thr Asp Glu Ile Ser Ile Leu Asn Pro Ser Ser Phe Ile Ala Val Ser
65                  70                  75                  80

Gly Asn Ile Tyr Val Gly Arg Gln Gln Asp Arg Tyr Ser Phe Val Glu
                85                  90                  95

Ile Gln Tyr Thr Gln Asn Asp Ser Ser Gly Arg Pro Lys Arg Gly Ile
            100                 105                 110

Thr Phe Thr Ser Gly Ala Ile Lys Tyr Asp Ile Ser Pro Asn Pro His
        115                 120                 125

Leu Ser Lys Ala Tyr Asn Asn Gly Gln Arg Asp Phe Tyr Asn Ser
    130                 135                 140

Leu Ala Leu Lys Val Arg Asp Tyr Ala Thr Asp His Asn Trp Val Arg
145                 150                 155                 160

Gly Gly Trp Asp Tyr Ser Gln Lys Leu Thr Phe Asn Leu Ser Gly Phe
                165                 170                 175

Ser Gly Ser Glu Gly Ser Arg Tyr Thr Leu Thr Pro Val Ala Lys Thr
            180                 185                 190
```

<210> SEQ ID NO 125
<211> LENGTH: 366
<212> TYPE: DNA
<213> ORGANISM: Bacillus thuringiensis

<400> SEQUENCE: 125

```
atgaaaaaag gatttcttgc cgtatcattg tccctgtttt tggccattgc tttaatcgtg     60
tttcctttct ccggcactaa tgtagatgct aaaggggtaa gtggctcaat cacgatcaac    120
aaagaaacat ataaatatat cgaagaatct ttcggaaaaa atcgagggat tacattcaac    180
ccaggtcaac atacgtacaa aataactccg aatcctcacg acaatcccaa atacaacaaa    240
aaacaagagc agttctatga ggaaatcgca aaaggcgtta aaactcttgt agaaaaatca    300
ggctggaaag atactctcag caacattaca gctctgggtg aaacctatac attagctcca    360
cgttaa                                                               366
```

<210> SEQ ID NO 126
<211> LENGTH: 121
<212> TYPE: PRT
<213> ORGANISM: Bacillus thuringiensis

<400> SEQUENCE: 126

Met Lys Lys Gly Phe Leu Ala Val Ser Leu Ser Leu Phe Leu Ala Ile
1               5                   10                  15

Ala Leu Ile Val Phe Pro Phe Ser Gly Thr Asn Val Asp Ala Lys Gly
            20                  25                  30

Val Ser Gly Ser Ile Thr Ile Asn Lys Glu Thr Tyr Lys Tyr Ile Glu
        35                  40                  45

Glu Ser Phe Gly Lys Asn Arg Gly Ile Thr Phe Asn Pro Gly Gln His
    50                  55                  60

Thr Tyr Lys Ile Thr Pro Asn Pro His Asp Asn Pro Lys Tyr Asn Lys
65                  70                  75                  80

Lys Gln Glu Gln Phe Tyr Glu Glu Ile Ala Lys Gly Val Lys Thr Leu
                85                  90                  95

Val Glu Lys Ser Gly Trp Lys Asp Thr Leu Ser Asn Ile Thr Ala Leu
            100                 105                 110

Gly Glu Thr Tyr Thr Leu Ala Pro Arg
        115                 120

<210> SEQ ID NO 127
<211> LENGTH: 56
<212> TYPE: DNA
<213> ORGANISM: Artificial Sequence
<220> FEATURE:
<223> OTHER INFORMATION: synthesized primer oligonucleotide

<400> SEQUENCE: 127
gtgtactagt aggaggtaac ttatgtcttt cttgaactgt ttcccttta aatatc        56

<210> SEQ ID NO 128
<211> LENGTH: 46
<212> TYPE: DNA
<213> ORGANISM: Artificial Sequence
<220> FEATURE:
<223> OTHER INFORMATION: synthesized primer oligonucleotide

<400> SEQUENCE: 128
tctcctcgag ctaagctcta ccatcatatt tcaaagtata tcttac                  46

<210> SEQ ID NO 129
<211> LENGTH: 47
<212> TYPE: DNA
<213> ORGANISM: Artificial Sequence
<220> FEATURE:
<223> OTHER INFORMATION: synthesized primer oligonucleotide

<400> SEQUENCE: 129
gtgtactagt atggataatc atttattagg gttactttca aaaatcc                 47

<210> SEQ ID NO 130
<211> LENGTH: 49
<212> TYPE: DNA
<213> ORGANISM: Artificial Sequence
<220> FEATURE:
<223> OTHER INFORMATION: synthesized primer oligonucleotide

<400> SEQUENCE: 130
tctcctcgag ttaagtttta gctacaggtg tcaaggtgta tctactacc               49

```
<210> SEQ ID NO 131
<211> LENGTH: 40
<212> TYPE: DNA
<213> ORGANISM: Artificial Sequence
<220> FEATURE:
<223> OTHER INFORMATION: synthesized primer oligonucleotide

<400> SEQUENCE: 131
gtgtactagt atgaaaaaag gatttcttgc cgtatcattg                           40

<210> SEQ ID NO 132
<211> LENGTH: 39
<212> TYPE: DNA
<213> ORGANISM: Artificial Sequence
<220> FEATURE:
<223> OTHER INFORMATION: synthesized primer oligonucleotide

<400> SEQUENCE: 132
tctcctcgag ttaacgtgga gctaatgtat aggtttcac                            39
```